United States Patent
Ahmed et al.

(10) Patent No.: US 11,787,834 B2
(45) Date of Patent: Oct. 17, 2023

(54) GLUCOCORTICOID RECEPTOR AGONISTS

(71) Applicant: Eli Lilly and Company, Indianapolis, IN (US)

(72) Inventors: Adel Ahmed Rashad Ahmed, Fishers, IN (US); Joshua Ryan Clayton, Fishers, IN (US); Jose Eduardo Lopez, Fishers, IN (US); William Thomas McMillen, Indianapolis, IN (US); Ryan Edward Stites, Indianapolis, IN (US); Takako Wilson, Indianapolis, IN (US); Jacqueline Mary Wurst, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 17/700,943

(22) Filed: Mar. 22, 2022

(65) Prior Publication Data
US 2022/0324904 A1    Oct. 13, 2022

Related U.S. Application Data

(60) Provisional application No. 63/164,613, filed on Mar. 23, 2021, provisional application No. 63/260,451, filed on Aug. 20, 2021.

(51) Int. Cl.
C07J 71/00    (2006.01)

(52) U.S. Cl.
CPC .................. *C07J 71/0031* (2013.01)

(58) Field of Classification Search
CPC .................................................. C07J 71/0031
See application file for complete search history.

(56) References Cited

U.S. PATENT DOCUMENTS 8,524,697 B2    9/2013    Anthes et al.

FOREIGN PATENT DOCUMENTS

| WO | WO2004071389 | * | 8/2004 |
|---|---|---|---|
| WO | 2006/138212 A1 | | 12/2006 |
| WO | 2009/069032 A2 | | 6/2009 |
| WO | 2009/085879 A2 | | 7/2009 |
| WO | 2009/108118 A1 | | 9/2009 |
| WO | 2017/132103 A2 | | 8/2017 |
| WO | 2017/210471 A1 | | 12/2017 |
| WO | 2018/089373 A2 | | 5/2018 |
| WO | 2019/106608 A1 | | 6/2019 |
| WO | 2019/106609 A1 | | 6/2019 |
| WO | 2021/216913 A1 | | 10/2021 |

OTHER PUBLICATIONS

Millan, D. S. et al., "Design and Synthesis of Long Acting Inhaled Corticosteroids for the Treatment of Asthma," Bioorganic & Medicinal Chemistry Letters, vol. 21, pp. 5826-5830 (2011).

* cited by examiner

Primary Examiner — Barbara P Badio
(74) Attorney, Agent, or Firm — Gabriel Magallanes

(57) ABSTRACT

The present invention provides a compound of Formula I:

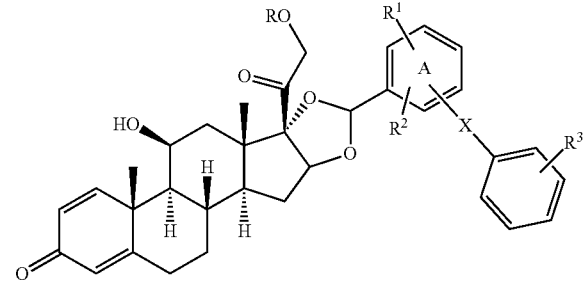

Formula I wherein R is H or

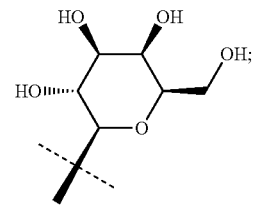

$R^1$ is H, halogen, C1-C3 alkyl, C3-C6 cycloalkyl, C1-C3 alkoxy, C2-C3 alkenyl, $OCF_3$,

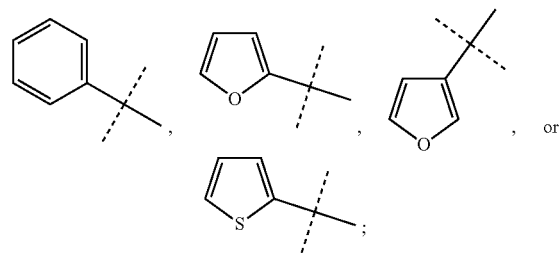

$R^2$ is H, halogen, C1-C3 alkyl, C1-C3 alkoxy, or C2-C4 alkenyl;
$R^3$ is $NH_2$, or $CH_2NH_2$; and
X is O, $OCH_2$, $OCH_2CH_2$, $OCH(CH_3)$, $CH_2O$, $SCH_2$, $CH_2S$, $CH_2$, $NHCH_2$, $CH_2NH$, $N(CH_3)CH_2$, $CH_2CH_2$, C≡C, or a bond, wherein X is connected to phenyl ring A at the ortho or the meta position, or a pharmaceutically acceptable salt thereof, wherein the compound of Formula I, or pharmaceutically acceptable salt thereof is useful for treating autoimmune and inflammatory diseases, such as atopic dermatitis and rheumatoid arthritis.

7 Claims, No Drawings

GLUCOCORTICOID RECEPTOR AGONISTS

The present disclosure provides compounds that are glucocorticoid receptor agonists and are useful for the treatment of autoimmune and inflammatory diseases, such as atopic dermatitis, inflammatory bowel disease, systemic lupus erythematosus, lupus nephritis, and rheumatoid arthritis, processes for preparing these compounds, pharmaceutical compositions comprising these compounds, and methods of using these compounds and compositions are also provided.

Atopic dermatitis is a chronic, pruritic relapsing and remitting inflammatory skin disease that occurs frequently in children, but also affects many adults. Current treatments of atopic dermatitis include light therapy, topical creams containing corticosteroids or calcineurin inhibitors, or a subcutaneous injectable biologic known as dupilumab. In spite of progress made in treating atopic dermatitis, there remains a significant need for new compounds to treat atopic dermatitis and other inflammatory and autoimmune diseases.

WO2017/210471 discloses certain glucocorticoid receptor agonists and immunoconjugates thereof useful for treating autoimmune or inflammatory diseases. WO2018/089373 discloses novel steroids, protein conjugates thereof, and methods for treating diseases, disorders, and conditions comprising administering the steroids and conjugates.

The present invention provides certain novel compounds which are glucocorticoid receptor agonists. The present invention further provides certain novel compounds which are prodrugs of glucocorticoid receptor agonists. In addition, the present invention provides certain novel compounds which are glucocorticoid receptor agonists useful in the treatment of autoimmune and inflammatory diseases such as atopic dermatitis, inflammatory bowel disease, rheumatoid arthritis, systemic lupus erythematosus, and lupus nephritis.

Accordingly, in one embodiment, the invention provides a compound of Formula I:

Formula I

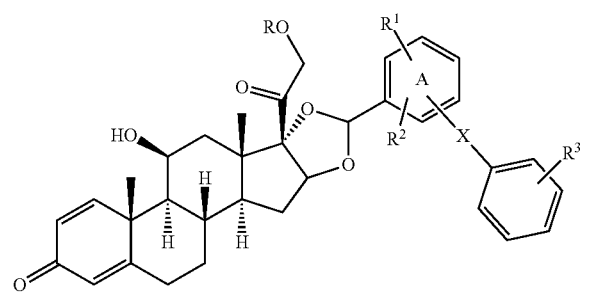

wherein R is H or

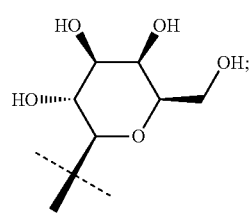

$R^1$ is H, halogen, CN, C1-C3 alkyl, C3-C6 cycloalkyl, C1-C3 alkoxy, C2-C3 alkenyl, $OCF_3$,

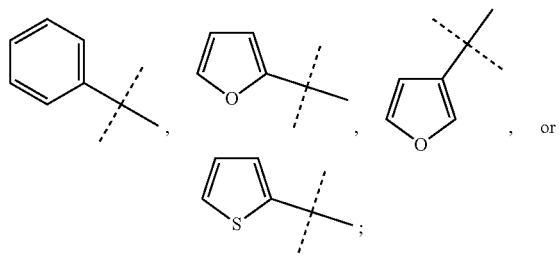

$R^2$ is H, halogen, C1-C3 alkyl, C1-C3 alkoxy, or C2-C3 alkenyl;
$R^3$ is $NH_2$, or $CH_2NH_2$; and
X is O, $OCH_2$, $OCH_2CH_2$, $CH_2O$, $SCH_2$, $CH_2S$, $CH_2$, $NHCH_2$, $CH_2NH$, $N(CH_3)CH_2$, $CH_2CH_2$, C≡C, or a bond, wherein X is connected to phenyl ring A at the ortho or the meta position, or a pharmaceutically acceptable salt thereof.

In one embodiment, the invention provides a compound of Formula Ia:

Formula Ia

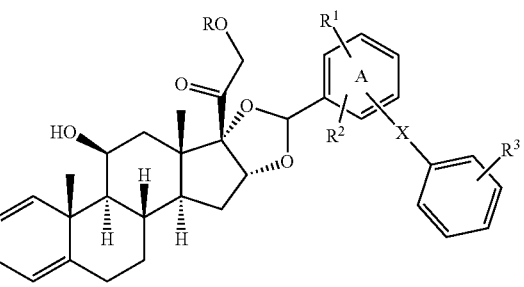

wherein R is H or

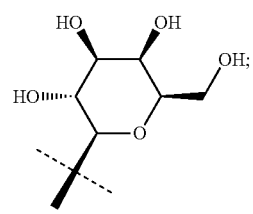

$R^1$ is H, halogen, C1-C3 alkyl, C3-C6 cycloalkyl, C1-C3 alkoxy, C2-C3 alkenyl, $OCF_3$,

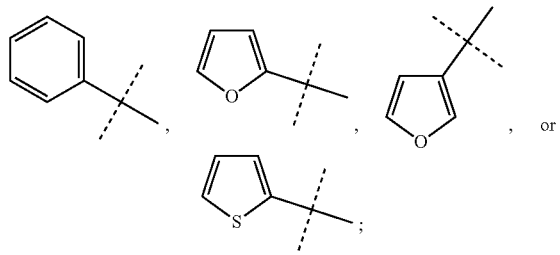

$R^2$ is H, halogen, C1-C3 alkyl, C1-C3 alkoxy, or C2-C4 alkenyl;
$R^3$ is $NH_2$, or $CH_2NH_2$; and X is O, OCH$_2$, OCH$_2$CH$_2$, OCH$_2$CC, OCH(CH$_3$), CH$_2$O, SCH$_2$, CH$_2$S, CH$_2$, NHCH$_2$, CH$_2$NH, N(CH$_3$)CH$_2$, CH$_2$CH$_2$, C≡C, or a bond, wherein X is connected to phenyl ring A at the ortho or the meta position, or a pharmaceutically acceptable salt thereof.

In one embodiment, the invention provides a compound of Formula Ib:

Formula Ib

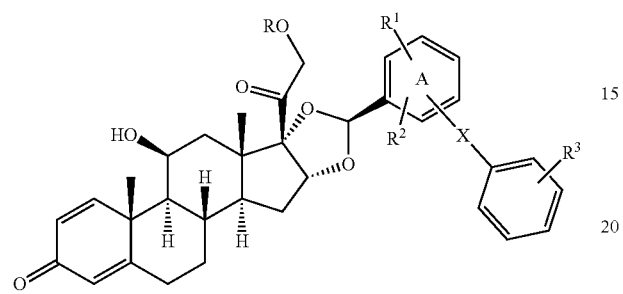

wherein R is H or

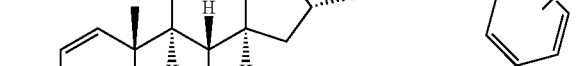

$R^1$ is H, halogen, C1-C3 alkyl, C3-C6 cycloalkyl, C1-C3 alkoxy, C2-C3 alkenyl, OCF$_3$,

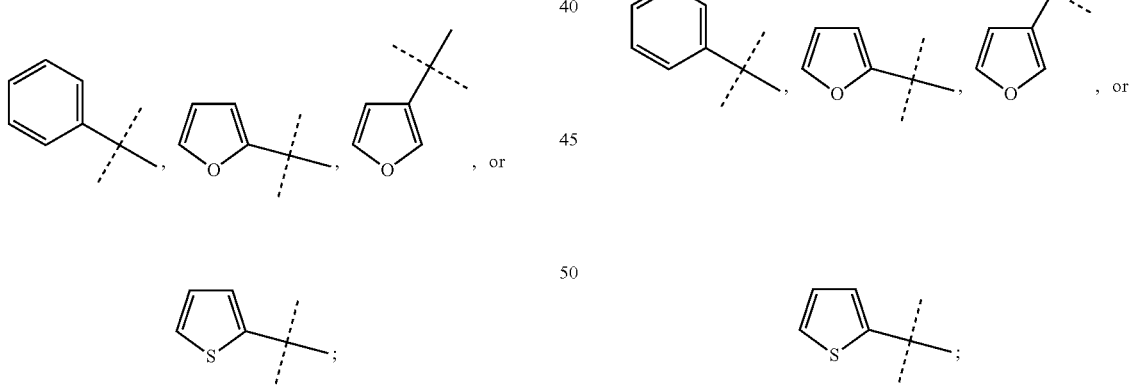

$R^2$ is H, halogen, C1-C3 alkyl, C1-C3 alkoxy, or C2-C4 alkenyl;

$R^3$ is NH$_2$, or CH$_2$NH$_2$; and

X is O, OCH$_2$, OCH$_2$CH$_2$, OCH(CH$_3$), CH$_2$O, SCH$_2$, CH$_2$S, CH$_2$, NHCH$_2$, CH$_2$NH, N(CH$_3$)CH$_2$, CH$_2$CH$_2$, C≡C, or a bond, wherein X is connected to phenyl ring A at the ortho or the meta position, or a pharmaceutically acceptable salt thereof.

In one embodiment, the invention provides a compound of Formula Ic:

Formula Ic $R^1$ is H, halogen, C1-C3 alkyl, C3-C6 cycloalkyl, C1-C3 alkoxy, C2-C3 alkenyl, OCF$_3$, $R^2$ is H, halogen, C1-C3 alkyl, C1-C3 alkoxy, or C2-C4 alkenyl;

$R^3$ is NH$_2$, or CH$_2$NH$_2$; and

X is O, OCH$_2$, OCH$_2$CH$_2$, OCH(CH$_3$), CH$_2$O, SCH$_2$, CH$_2$S, CH$_2$, NHCH$_2$, CH$_2$NH, N(CH$_3$)CH$_2$, CH$_2$CH$_2$, C≡C, or a bond, wherein X is connected to phenyl ring A at the ortho or the meta position, or a pharmaceutically acceptable salt thereof.

In an embodiment, the invention provides a compound of Formula Ib(i):

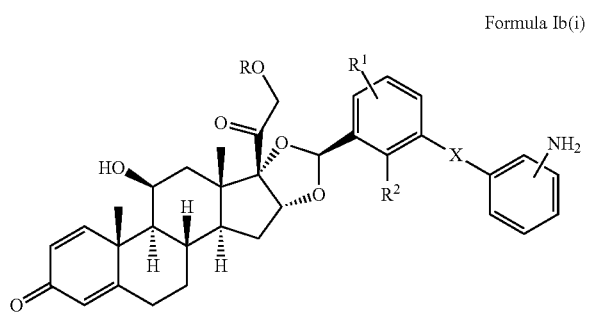

Formula Ib(i)

or a pharmaceutically acceptable salt thereof.

In an embodiment, the invention provides a compound of Formula Ic(i):

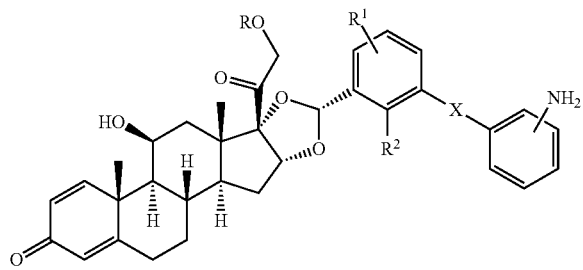

Formula Ic(i)

or a pharmaceutically acceptable salt thereof.

In an embodiment, the invention provides a compound of Formula Ib(ii):

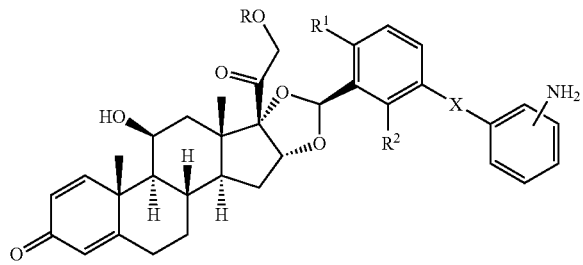

Formula Ib(ii)

or a pharmaceutically acceptable salt thereof.

In an embodiment, the invention provides a compound of Formula Ic(ii):

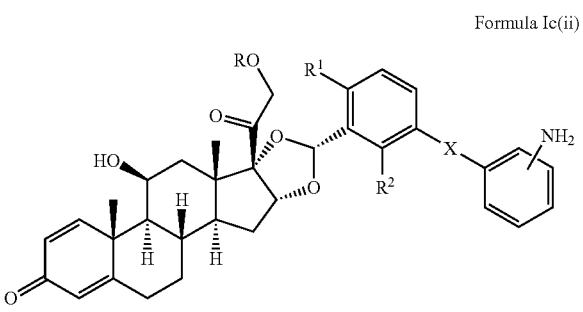

Formula Ic(ii)

or a pharmaceutically acceptable salt thereof.

In an embodiment, the invention provides a compound of Formula Ib(iii):

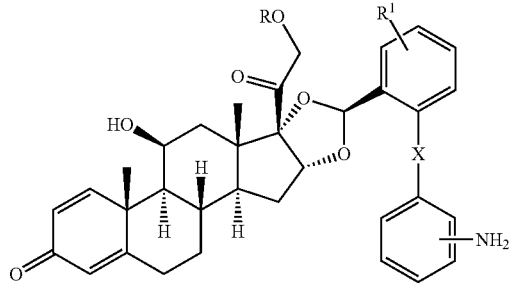

Formula Ib(iii)

or a pharmaceutically acceptable salt thereof.

In an embodiment, the invention provides a compound of Formula Ic(iii):

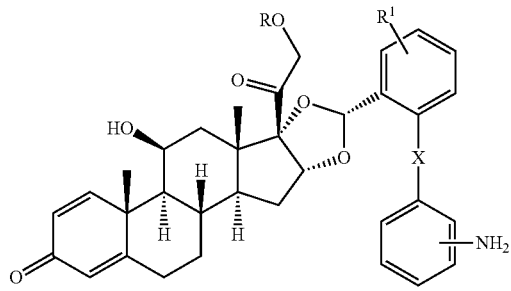

Formula Ic(iii)

or a pharmaceutically acceptable salt thereof.

In one embodiment, the invention provides a compound of Formula II:

Formula II

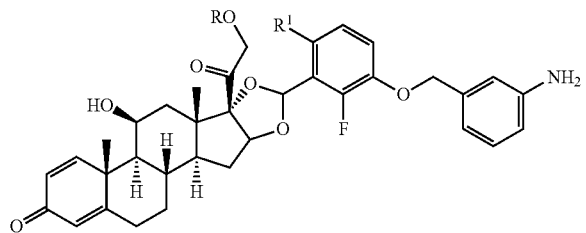

wherein R is H or

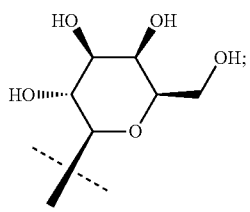

and
$R^1$ is —$CH_3$ or —$OCH_3$,
or a pharmaceutically acceptable salt thereof.

In a particular embodiment, the invention provides a compound of Formula IIa:

Formula IIa

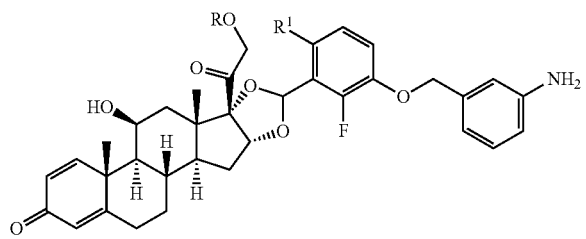

wherein R is H or

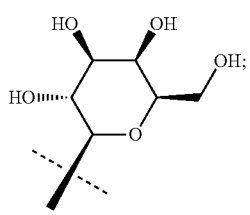

and
$R^1$ is —$CH_3$ or —$OCH_3$,
or a pharmaceutically acceptable salt thereof.

In a particular embodiment, the invention provides a compound of Formula IIb:

Formula IIb

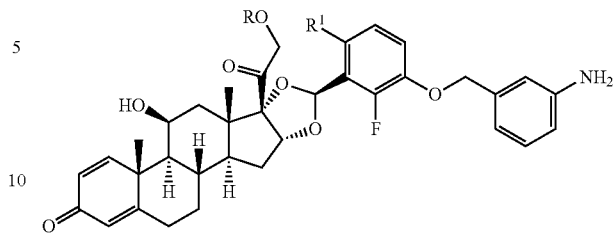

wherein R is H or

and
$R^1$ is —$CH_3$ or —$OCH_3$, or a pharmaceutically acceptable salt thereof.

In a particular embodiment, the invention provides a compound of Formula IIc:

Formula IIc

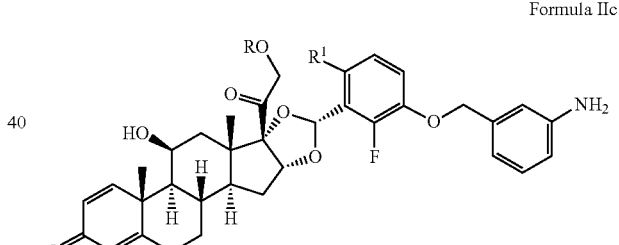

wherein R is H or

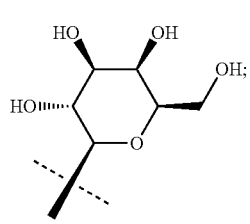

and
$R^1$ is —$CH_3$ or —$OCH_3$, or a pharmaceutically acceptable salt thereof.

In an embodiment, the invention provides a compound of Formula III:

Formula III

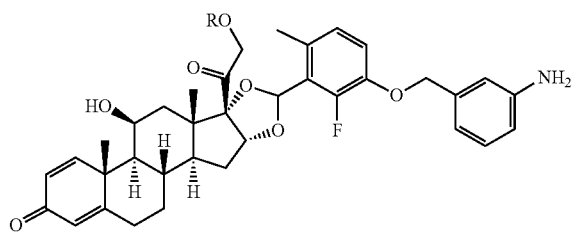

wherein R is H or

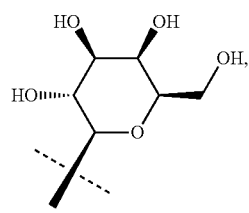

or a pharmaceutically acceptable salt thereof.

In a particular embodiment, the invention provides a compound of Formula IIIa:

Formula IIIa

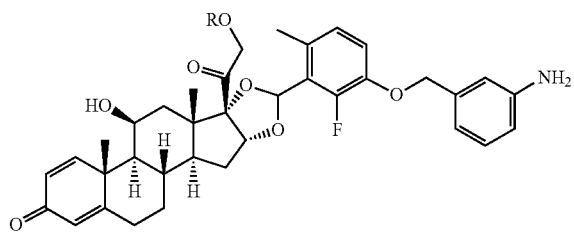

wherein R is H or

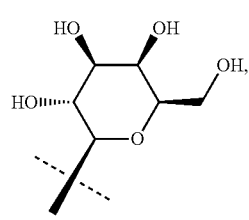

or a pharmaceutically acceptable salt thereof.

In a particular embodiment, the invention provides a compound of Formula IIIb:

Formula IIIb

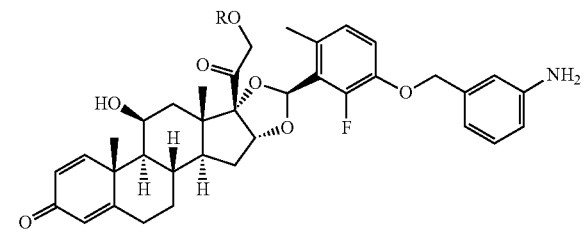

wherein R is H or

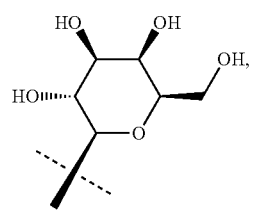

or a pharmaceutically acceptable salt thereof.

In a particular embodiment, the invention provides a compound of Formula IIIc:

Formula IIIc

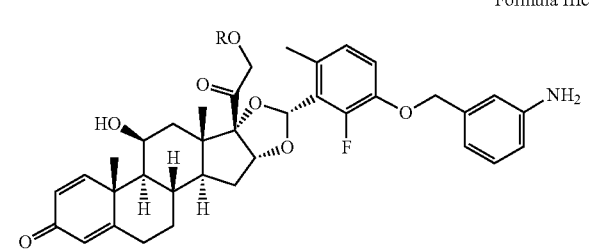

wherein R is H or

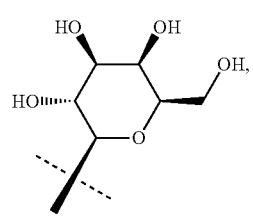

or a pharmaceutically acceptable salt thereof.

In an embodiment, R is H.
In an embodiment, R is

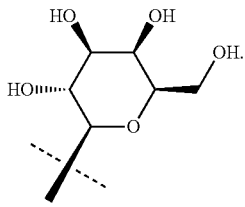

In an embodiment, R$^1$ is CH$_3$.
In an embodiment, R$^1$ is H.
In an embodiment, R$^1$ is OCH$_3$.
In an embodiment, R$^1$ is F.
In an embodiment, R$^2$ is H.
In an embodiment, R$^2$ is CH$_3$.
In an embodiment, R$^2$ is F.
In an embodiment, R$^2$ is OCH$_3$.
In an embodiment, X is O.
In an embodiment, X is OCH$_2$.
In an embodiment, X is SCH$_2$.
In an embodiment, X is CH$_2$.
In an embodiment, X is a bond.
In an embodiment, R is H, R$^1$ is CH$_3$, R$^2$ is F, and X is OCH$_2$.
In an embodiment, R is H, R$^1$ is OCH$_3$, R$^2$ is F, and X is OCH$_2$.
In an embodiment, X is connected to phenyl ring A at the meta position.
In an embodiment, X is connected to phenyl ring A at the ortho position.

In an embodiment, the present invention also provides a method of treating an inflammatory disease in a patient in need of such treatment, comprising administering to the patient an effective amount of a compound of Formula I, or a pharmaceutically acceptable salt thereof. In an embodiment, the present invention also provides a method of treating atopic dermatitis in a patient in need of such treatment, comprising administering to the patient an effective amount of a compound of Formula I, or a pharmaceutically acceptable salt thereof. In an embodiment, the present invention further provides a method of treating inflammatory bowel disease in a patient in need of such treatment, comprising administering to the patient an effective amount of a compound of Formula I, or a pharmaceutically acceptable salt thereof. In an embodiment, the present invention further provides a method of treating rheumatoid arthritis in a patient in need of such treatment, comprising administering to the patient an effective amount of a compound of Formula I, or a pharmaceutically acceptable salt thereof. In an embodiment, the present invention also provides a method of treating systemic lupus erythematosus in a patient in need of such treatment, comprising administering to the patient an effective amount of a compound of Formula I, or a pharmaceutically acceptable salt thereof. In an embodiment, the present invention also provides a method of treating lupus nephritis in a patient in need of such treatment, comprising administering to the patient an effective amount of a compound of Formula I, or a pharmaceutically acceptable salt thereof.

In an embodiment, the present invention further provides a compound of Formula I, or a pharmaceutically acceptable salt thereof for use in therapy. In an embodiment, the present invention provides a compound of Formula I, or a pharmaceutically acceptable salt thereof for use in treating an inflammatory disease. In an embodiment, the present invention provides a compound of Formula I, or a pharmaceutically acceptable salt thereof, for use in treating atopic dermatitis. In an embodiment, the present invention provides a compound of Formula I, or a pharmaceutically acceptable salt thereof, for use in treating rheumatoid arthritis. In an embodiment, the present invention provides a compound of Formula I, or a pharmaceutically acceptable salt thereof, for use in treating inflammatory bowel disease. In an embodiment, the present invention provides a compound of Formula I, or a pharmaceutically acceptable salt thereof, for use in treating lupus nephritis. In an embodiment, the present invention provides a compound of Formula I, or a pharmaceutically acceptable salt thereof, for use in treating systemic lupus erythematosus.

In an embodiment, the present invention also provides the use of a compound of Formula I, or a pharmaceutically acceptable salt thereof, for the manufacture of a medicament for treating an inflammatory disease. In an embodiment, the present invention provides the use of a compound of Formula I, or a pharmaceutically acceptable salt thereof, for the manufacture of a medicament for treating atopic dermatitis. In an embodiment, the present invention provides the use of a compound of Formula I, or a pharmaceutically acceptable salt thereof, for the manufacture of a medicament for treating rheumatoid arthritis. In an embodiment, the present invention further provides the use of a compound of Formula I, or a pharmaceutically acceptable salt thereof, for the manufacture of a medicament for treating inflammatory bowel disease. In an embodiment, the present invention further provides the use of a compound of Formula I, or a pharmaceutically acceptable salt thereof, for the manufacture of a medicament for treating lupus nephritis. In an embodiment, the present invention also provides the use of a compound of Formula I, or a pharmaceutically acceptable salt thereof, for the manufacture of a medicament for treating systemic lupus erythematosus.

In an embodiment, the present invention further provides a pharmaceutical composition, comprising a compound of Formula I, or a pharmaceutically acceptable salt thereof, with one or more pharmaceutically acceptable carriers, diluents, or excipients. In an embodiment, the present invention further provides a process for preparing a pharmaceutical composition, comprising admixing a compound of Formula I, or a pharmaceutically acceptable salt thereof, with one or more pharmaceutically acceptable carriers, diluents, or excipients. In an embodiment, the present invention also encompasses novel intermediates and processes for the synthesis of compounds of Formula I.

As used herein, the terms "treating", "treatment", or "to treat" includes restraining, slowing, stopping, or reversing the progression or severity of an existing symptom or disorder.

As used herein, the term "patient" refers to a mammal, in particular a human.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be determined by one skilled in the art by the use of known techniques and by observing results obtained under analogous circumstances. In determining the effective amount for a patient, a number of factors are considered by the attending diagnostician, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

As used herein, it is understood that Formula I encompasses Formulas Ia, Ib, Ic, Ib(i), Ic(i), Ib(ii), Ic(ii), Ib(iii), Ic(iii), II, IIa, IIb, IIc, III, IIIa, IIIb, and IIIc, and all references to Formula I herein should be read as including Formulas Ia, Ib, Ic, Ib(i), Ic(i), Ib(ii), Ic(ii), Ib(iii), Ic(iii), II, IIa, IIb, IIc, III, IIIa, IIIb, and IIIc.

As used herein, it is understood that Formula II encompasses Formulas IIa, IIb, and IIc, and all references to Formula II herein should be read as including Formulas IIa, IIb, and IIc.

As used herein, it is understood that Formula III encompasses Formulas IIIa, IIIb, and IIIc, and all references to Formula III herein should be read as including Formulas IIIa, IIIb, and IIIc.

As used herein "halogen" refers to F, Cl, Br, and I.

As used herein "C1-C3 alkyl" refers to $CH_3$, $CH_2CH_3$, $CH_2CH_2CH_3$, and $CH(CH_3)_2$.

As used herein "C3-C6 cycloalkyl" refers to cyclopropyl, cyclobutyl, cyclopentyl, and cyclohexyl.

As used herein "C1-C3 alkoxy" refers to $OCH_3$, $OCH_2CH_3$, $OCH_2CH_2CH_3$, and $OCH(CH_3)_2$.

As used herein "C2-C3 alkenyl" refers to $HC=CH_2$, and $C(CH_3)=CH_2$.

As used herein, the ortho and meta positions on phenyl ring A are shown in Formula I below:

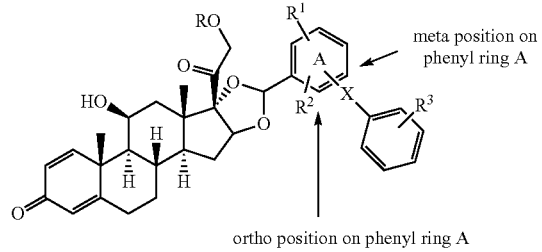

Formula I

For example, the compound of Formula I' illustrates X connected to phenyl ring A at the meta position:

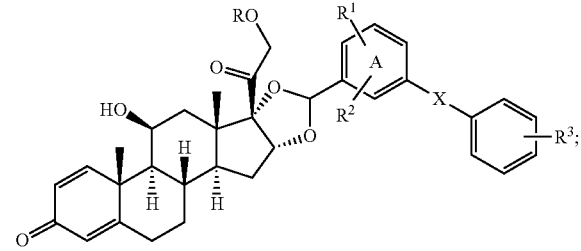

Formula I' and the compound of Formula I" illustrates X connected to phenyl ring A at the ortho position:

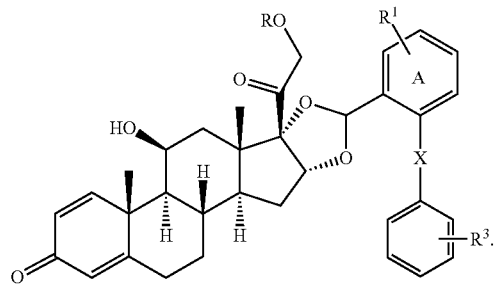

Formula I"

It is appreciated by one of ordinary skill in the art that when X is connected to phenyl ring A at the ortho position as shown in Formula I", then $R^2$ is H.

In addition, a compound of the present invention can be conjugated with an antibody to form an antibody drug conjugate (ADC) by methods understood by one of skill in the art. One example of such conjugation would include connection of a compound of the present invention to an antibody via a linker compound. Linker compounds known to those of skill in the art include, for example, cleavable linkers and noncleavable linkers. Such an ADC can deliver the compound of the present invention to specific target tissues or cells. Accordingly, provided herein are also ADCs comprising a compound of Formula I. In some embodiments, the compound of Formula I is conjugated to an antibody via a linker, e.g., a cleavable linker or a noncleavable linker.

The compounds or conjugates of the present invention can be formulated as pharmaceutical compositions administered by any route which makes the compound or conjugate bioavailable including, for example, oral, topical, or subcutaneous administration. Such pharmaceutical compositions, including ADCs, can be prepared using techniques and methods known in the art. Such pharmaceutical compositions, including ADCs can be prepared using techniques and methods known in the art (See, e.g., Remington: The Science and Practice of Pharmacy, A. Adejare, Editor, $23^{nd}$ Edition, published 2020, Elsevier Science; WO 2017/062271, and WO 2017/210471).

Furthermore, compounds of the present invention that have the hydroxy group at C21 capped wherein R is:

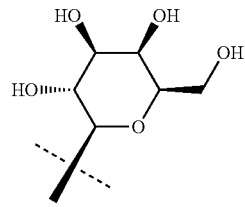

behave as prodrugs and are metabolized in vitro or in vivo to provide the active glucocorticoid receptor agonist wherein R is H.

Included within the scope of the present invention is a pharmaceutically acceptable salt of Formula I. A pharmaceutically acceptable salt of a compound of the invention, such as a compound of Formula I can be formed, for example, by reaction of an appropriate free base of a compound of the invention with an appropriate pharmaceutically acceptable acid in a suitable solvent such as diethyl ether under standard conditions well known in the art. See, for example, Berge, S. III., et al., "Pharmaceutical Salts," *Journal of Pharmaceutical Sciences,* 66: 1-19, (1977).

Certain compounds described in the following preparations may contain a suitable nitrogen protecting group referred to herein as "Pg". It is understood that protecting groups may be varied as appreciated by one of skill in the art depending on the particular reaction conditions and the particular transformations to be performed. The protection and deprotection conditions are well known to the skilled artisan and are described in the literature (See for example *"Greene's Protective Groups in Organic Synthesis"*, Fourth Edition, by Peter G. M. Wuts and Theodora W. Greene, John Wiley and Sons, Inc. 2007).

TABLE 1

Abbreviations and definitions

| Term | Definition |
| --- | --- |
| ACN | acetonitrile |
| aq | aqueous |
| Å | angstrom(s) |
| BOC/Boc | tert-butyloxycarbonyl |
| C18 | octadecylsilane |
| DCM | dichloromethane |
| DEA | diethylamine |
| DIBAL-H | diisobutylaluminum hydride |
| DMEA | dimethylethylamine |
| DMF | N,N-dimethylformamide |
| DMSO | dimethyl sulfoxide |
| dppf | 1,1'-bis(diphenylphosphino)ferrocene |
| equiv | equivalent(s) |
| ES/MS | electrospray mass spectrometry |
| EtOAc | ethyl acetate |
| EtOH | ethanol |
| FA | formic acid |
| g | gram(s) |
| h | hour(s) |
| HPLC | high performance liquid chromatography |
| IPA | isopropanol |
| IPAm | isopropylamine |
| L | liter(s) |
| LC | liquid chromatography |
| LCMS | liquid chromatography mass spectrometry |
| LDA | lithium diisopropylamide |
| M | molar |
| mbar | millibar(s) |
| MeOH | methanol |
| min | minute(s) |
| mL | milliliter(s) |
| mM | millimolar |
| mmol | millimole(s) |
| mol | mole(s) |
| MS | mass spectrometry |
| MTBE | methyl tert-butyl ether |
| MW | molecular weight |
| m/z | mass-to-charge ratio |
| nm | nanometer(s) |
| NMR | nuclear magnetic resonance |
| Pet ether | petroleum ether |
| ppm | parts per million |
| ROE | rotating-frame Overhauser enhancement |
| RP-HPLC | reverse-phase HPLC |
| rt | room temperature |
| satd | saturated |
| SFC | supercritical fluid chromatography |
| SM | starting material |
| THF | tetrahydrofuran |
| wt | weight |

The compounds of the present invention, or salts thereof, may be readily prepared by a variety of procedures known to one of ordinary skill in the art, some of which are illustrated in the preparations and examples below. One of ordinary skill in the art recognizes that the specific synthetic steps for each of the routes described may be combined in different ways, or in conjunction with steps from different schemes, to prepare compounds of the invention, or salts thereof. The product of each step can be recovered by conventional methods well known in the art, including extraction, evaporation, precipitation, chromatography, filtration, trituration, and crystallization. All substituents unless otherwise indicated, are as previously defined. The reagents and starting materials are readily available to one of ordinary skill in the art. The following preparations, examples, and assays further illustrate the invention, but should not be construed to limit the scope of the invention in any way.

Preparation 1

6-Bromo-2-fluoro-3-methoxybenzaldehyde

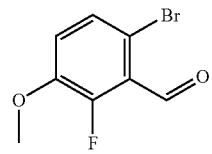

Two reactions were carried out in parallel. To a solution of 4-bromo-2-fluoro-1-methoxybenzene (250 g, 1.2 mol) in THF (1500 mL) was added LDA (2 M, 730 mL) slowly at −78° C., over 30 min. After an additional 30 min, DMF (140 mL, 1.8 mol) was added at −78° C. slowly over 30 min. After 1 h, the two reactions were combined and the mixture was diluted with aq citric acid (2000 mL) and extracted with EtOAc (1500 mL×2). The combined organic layers were washed with saturated brine (1000 mL) and concentrated under reduced pressure to give a residue. The residue was triturated with petroleum ether (1000 mL) at rt over 12 h to give the title compound (382 g, 67% yield). ES/MS m/z 233.9 (M+H).

Preparation 2

2-Fluoro-3-methoxy-6-methylbenzaldehyde

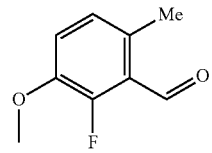

Three reactions were carried out in parallel. 6-Bromo-2-fluoro-3-methoxybenzaldehyde (120 g, 5.3 mol), methylboronic acid (47 g, 7.9 mol), Pd(dppf)Cl$_2$ (12 g, 0.02 mol), and Cs$_2$CO$_3$ (340 g, 1.1 mol) were added to a mixture of dioxane (600 mL) and water (120 mL). The mixture was stirred at 120° C. After 12 h, the three reactions were combined and the mixture was diluted with satd aq NH$_4$Cl (1000 mL) and extracted with MTBE (1500 mL×2). The combined organic layers were washed with satd aq NaCl (1000 mL) and concentrated under reduced pressure to give a residue. The residue was purified by normal phase chromatography, eluting with 40:1 Pet ether:EtOAc to give the title compound (180 g, 59% yield). ES/MS m/z 169.3 (M+H).

Preparation 3

2-Fluoro-3-hydroxy-6-methylbenzaldehyde

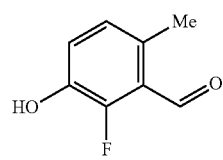

2-Fluoro-3-methoxy-6-methylbenzaldehyde (175 g, 1.0 mol) was added into DCM (1050 mL). BBr₃ (200 mL, 2.1 mol) was added slowly into the solution at 0° C. The reaction was stirred at rt. After 1 h, the mixture was diluted with satd aq sodium bicarbonate (1000 mL) until pH=7-8 and was extracted with MTBE (1500 mL×2). The combined organic layers were washed with satd aq NaCl (1000 mL) and concentrated under reduced pressure to give the title compound (110 g, 68% yield). ES/MS m/z 154.9 (M+H).

Preparation 4 tert-Butyl N-[3-[(2-fluoro-3-formyl-4-methyl-phenoxy)methyl]phenyl]carbamate

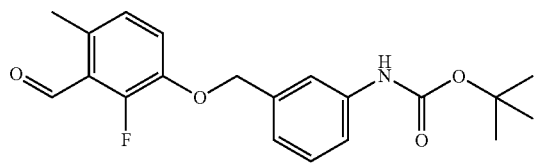 [SMILES: Cc1ccc(OCc2cccc(NC(=O)OC(C)(C)C)c2)c(F)c1C=O]

2-Fluoro-3-hydroxy-6-methylbenzaldehyde (130 g, 0.84 mol), tert-butyl (3-(bromomethyl)phenyl)carbamate (200 g, 0.70 mol), and potassium carbonate (350 g, 2.5 mol) were added in acetonitrile (780 mL) at rt and then heated to 50° C. After 5 h, the reaction was diluted with water (600 mL) and extracted with EtOAc (800 mL×2). The combined organic layers were washed with brine (800 mL) and concentrated under reduced pressure to give a residue. The residue was purified by normal phase chromatography, eluting with 50:1 Pet ether:EtOAc to give crude product. The crude product was triturated with MTBE (500 mL) at rt for 30 min to give the title compound (103 g, 32% yield). ES/MS m/z 382.1 (M+Na).

Preparation 5

(2R,3S,4S,5R,6R)-2-(Acetoxymethyl)-6-(2-((6aR, 6bS,7S,8aS,8bS,10S,11aR,12aS,12bS)-10-(3-((3-aminobenzyl)oxy)-2-fluoro-6-methylphenyl)-7-hydroxy 8a-dimethyl-4-oxo-1,2,4,6a,6b,7,8,8a,11a,12, 12a,12b-dodecahydro-8bH-naphtho[2',1':4,5]indeno [1,2-d][1,3]dioxol-8b-yl)-2-oxoethoxy)tetrahydro-2H-pyran-3,4,5-triyl triacetate

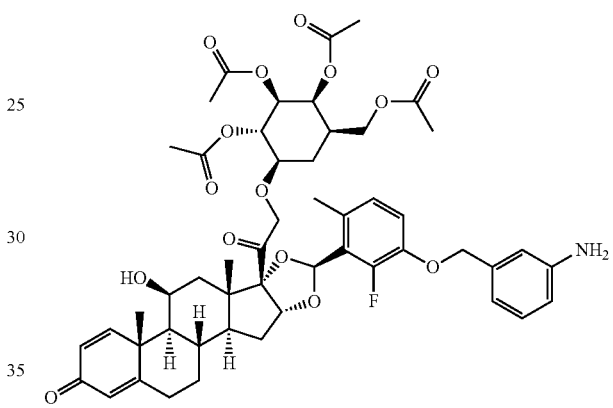

3 Å Molecular sieves (5 g) were added to (6aR,6bS,7S, 8aS,8bS,10S,11aR,12aS,12bS)-10-(3-((3-aminobenzyl) oxy)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3] dioxol-4-one (150 mg, 0.24 mmol, Example 2 below), 2,3,4,6-tetra-O-acetyl-alpha-D-galactopyranosyl bromide (155 mg, 0.37 mmol), and DCM (5 mL) at rt. After 1 h, the reaction was cooled to 0° C. Silver(I) oxide (115 mg, 0.49 mmol) and trimethylsilyl trifluoromethanesulfonate (45 μL, 0.24 mmol) were added. After 30 min, the reaction was quenched with satd aq sodium bicarbonate, filtered over diatomaceous earth, and rinsed with DCM (10 mL) and methanol (10 mL). The combined organic layers were concentrated under reduced pressure to give a residue. The residue was purified by reverse phase chromatography, eluting with 1:5 10 mM ammonium bicarbonate water+5% methanol:acetonitrile to give the title compound (43 mg, 19% yield). ES/MS m/z 948.0 (M+1).

Preparation 6 tert-Butyl (2-fluoro-4-methoxyphenoxy)diphenylsilane

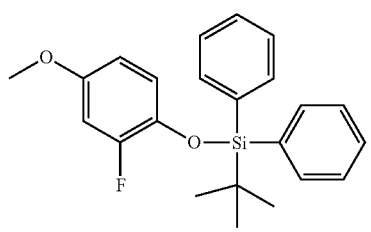 [SMILES: COc1ccc(O[Si](c2ccccc2)(c2ccccc2)C(C)(C)C)c(F)c1]

To a solution of 2-fluoro-4-methoxyphenol (25 g, 180 mmol) in DMF (350 mL 0.5 M) was added imidazole (18 g, 260 mmol) and tert-butylchlorodiphenylsilane (55 mL, 200 mmol). The reaction was stirred for 18 h at rt. The mixture was diluted with ethyl acetate. The organic solution was washed with water and brine, dried over $Na_2SO_4$, filtered, and concentrated to a crude residue. The residue was purified by normal phase purification, eluting with 5:1 hexanes: ethyl acetate to give the title compound (67 g, 93% yield). $^1$H NMR (399.8 MHz, $d_6$-DMSO) δ 7.67-7.65 (m, 4H), 7.51-7.44 (m, 6H), 6.82 (dd, J=2.9, 12.7 Hz, 1H), 6.59 (t, J=9.4 Hz, 1H), 6.47 (ddd, J=9.0, 3.0, 1.4 Hz, 1H), 3.64 (s, 3H), 1.06 (s, 9H).

Preparation 7

2-Fluoro-3-hydroxy-6-methoxybenzaldehyde

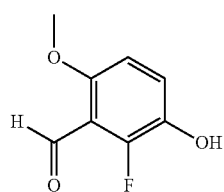

tert-Butyl (2-fluoro-4-methoxyphenoxy)diphenylsilane (56 g, 150 mmol, Preparation 6) was dissolved in 50 mL toluene and concentrated under vacuum for 18 h. The dried solid was dissolved in THF (500 mL) and cooled to −80° C. n-Butyllithium (1.7 M, 100 mL, 170 mmol) was added rapidly to the cooled solution with a large bore cannula. After 1.5 h, DMF (25 mL, 320 mmol) was added to the solution and the ice bath was removed. After 30 min, 5N aqueous HCl (35 mL) was added to the reaction, then tetrabutylammonium fluoride (1 M in THF, 185 mL, 185 mmol) was added. After 2.5 h, the organic layer was evaporated, acidified with 5N aqueous HCl, and partitioned between ethyl acetate and water (500 mL). The combined organic extracts were washed with water and brine, dried over $MgSO_4$, filtered, and concentrated to a crude residue. The residue was purified by normal phase purification, eluting with 1:1 hexanes:ethyl acetate to give the title compound (22 g, 88% yield). MS m/z 170.8 (M+H).

Scheme 1

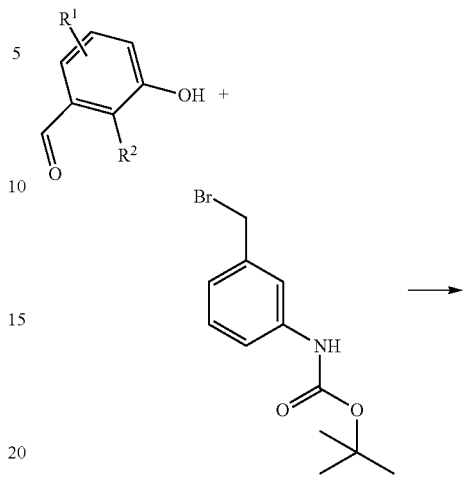

Preparation 8 tert-Butyl (3-((2-fluoro-3-formyl-4-methoxyphenoxy)methyl)phenyl)carbamate

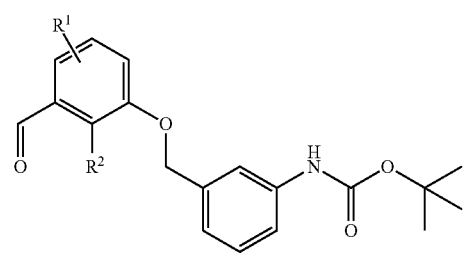

2-Fluoro-3-hydroxy-6-methoxybenzaldehyde (2.5 g, 15 mmol) and tert-butyl N-[3-(bromomethyl)phenyl]carbamate (5.1 g, 18 mmol) were dissolved in acetonitrile (50 mL). Potassium carbonate (2.9 g, 29 mmol) was added to the slurry and the reaction was stirred at rt. After 1 h, the reaction was warmed to 40° C. After 3 h, the reaction was cooled, filtered, and the solvent was evaporated. The crude residue was purified by normal phase purification, eluting with 7:3 hexanes:EtOAc to give the title compound (3.1 g, 57% yield). MS m/z 374.4 (M−H).

The following compounds in Table 2 were prepared in a manner essentially analogous to the procedure described in Preparation 8.

TABLE 2

Preparations 9-50

| Prep. No. | Structure | ES/MS (m/z) (M + H) | Starting phenol |
|---|---|---|---|
| 9 | 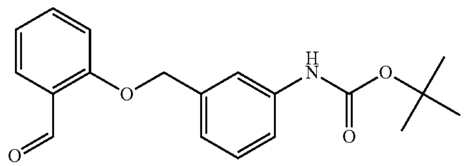 [SMILES: CC(C)(C)OC(=O)Nc1cccc(COc2ccccc2C=O)c1] | 326.0 | 2-hydroxybenzaldehyde |
| 10 | 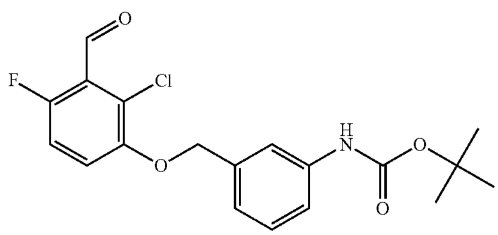 [SMILES: CC(C)(C)OC(=O)Nc1cccc(COc2ccc(F)c(C=O)c2Cl)c1] | 379.0 | 2-chloro-6-fluoro-3-hydroxybenzaldehyde |
| 11 | 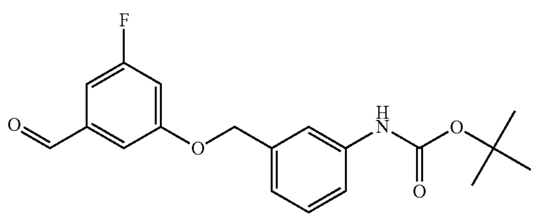 [SMILES: CC(C)(C)OC(=O)Nc1cccc(COc2cc(F)cc(C=O)c2)c1] | 344.0 | 3-fluoro-5-hydroxybenzaldehyde |
| 12 | 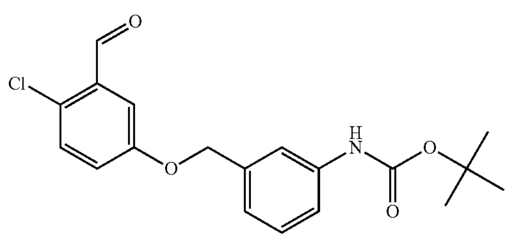 [SMILES: CC(C)(C)OC(=O)Nc1cccc(COc2ccc(Cl)c(C=O)c2)c1] | 360.0 | 2-chloro-5-hydroxybenzaldehyde |
| 13 | 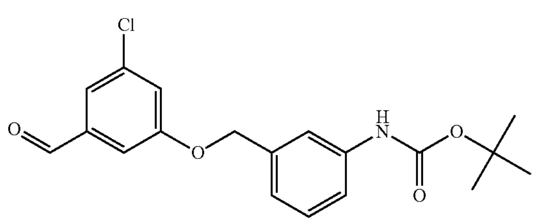 [SMILES: CC(C)(C)OC(=O)Nc1cccc(COc2cc(Cl)cc(C=O)c2)c1] | 360.0 | 3-chloro-5-hydroxybenzaldehyde |
| 14 | 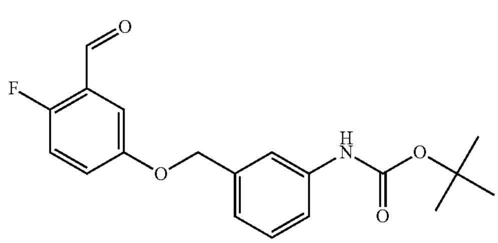 [SMILES: CC(C)(C)OC(=O)Nc1cccc(COc2ccc(F)c(C=O)c2)c1] | 344.0 | 2-fluoro-5-hydroxybenzaldehyde |

TABLE 2-continued

Preparations 9-50

| Prep. No. | Structure | ES/MS (m/z) (M + H) | Starting phenol |
|---|---|---|---|
| 15 | 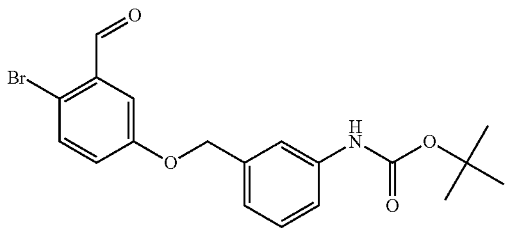 | 404.0 | 2-bromo-5-hydroxybenzaldehyde |
| 16 | 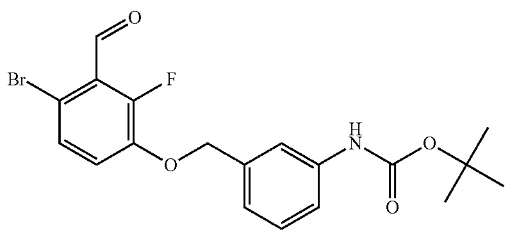 | 422.0 (M − H) | 6-bromo-2-fluoro-3-hydroxybenzaldehyde |
| 17 | 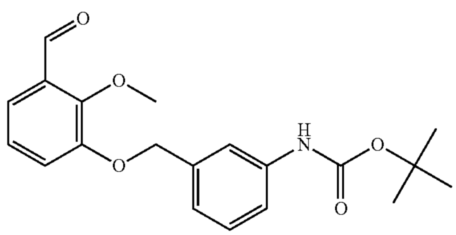 [SMILES: COc1c(C=O)cccc1OCc1cccc(NC(=O)OC(C)(C)C)c1] | 356.4 (M − H) | 3-hydroxy-2-methoxybenzaldehyde |
| 18 | 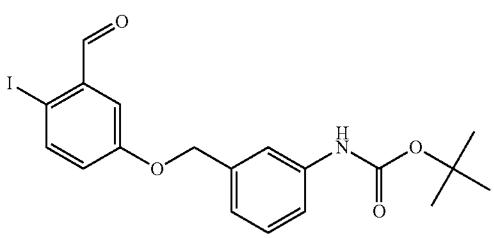 [SMILES: CC(C)(C)OC(=O)Nc1cccc(COc2ccc(I)c(C=O)c2)c1] | 451.4 (M − H) | 5-hydroxy-2-iodobenzaldehyde |
| 19 | 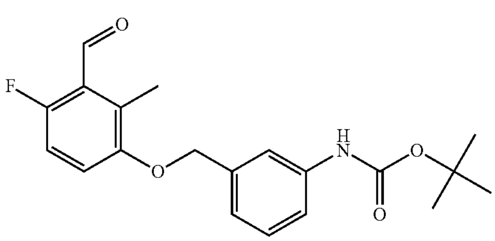 [SMILES: Cc1c(OCc2cccc(NC(=O)OC(C)(C)C)c2)ccc(F)c1C=O] | 359.2 | 6-fluoro-3-hydroxy-2-methylbenzaldehyde |
| 20 | 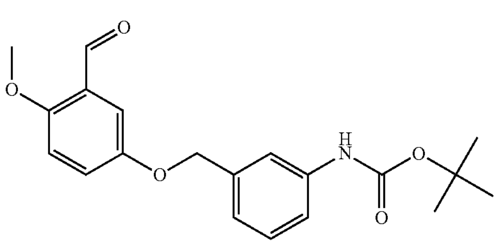 [SMILES: COc1ccc(OCc2cccc(NC(=O)OC(C)(C)C)c2)cc1C=O] | 356.0 (M − H) | 5-hydroxy-2-methoxybenzaldehyde |

TABLE 2-continued
Preparations 9-50
| Prep. No. | Structure | ES/MS (m/z) (M + H) | Starting phenol |
|---|---|---|---|
| 21 | 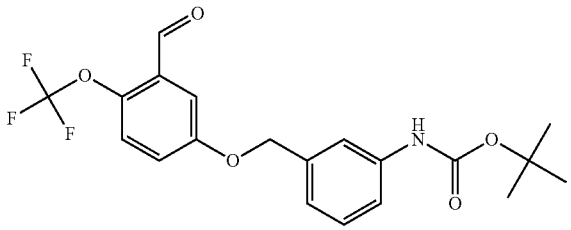 [SMILES: CC(C)(C)OC(=O)Nc1cccc(COc2ccc(OC(F)(F)F)c(C=O)c2)c1] | 410.6 (M − H) | 5-hydroxy-2-(trifluoromethoxy)benzaldehyde |
| 22 | 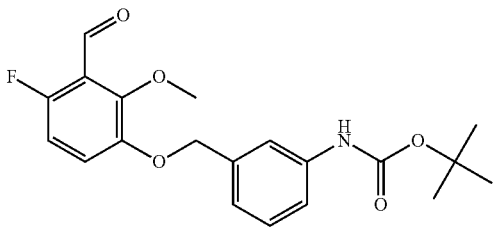 [SMILES: COc1c(OCc2cccc(NC(=O)OC(C)(C)C)c2)ccc(F)c1C=O] | 374.5 (M − H) | 6-fluoro-3-hydroxy-2-methoxybenzaldehyde |
| 23 | 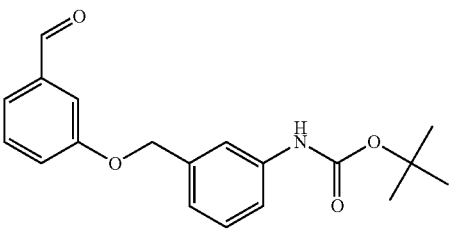 [SMILES: CC(C)(C)OC(=O)Nc1cccc(COc2cccc(C=O)c2)c1] | 363.2 | 3-hydroxybenzaldehyde |
| 24 | 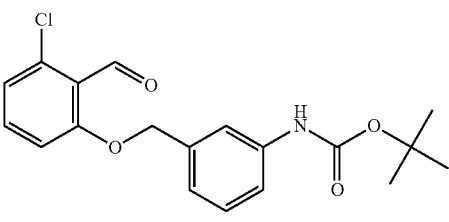 | 360.0 (M − H) | 2-chloro-6-hydroxybenzaldehyde |
| 25 | 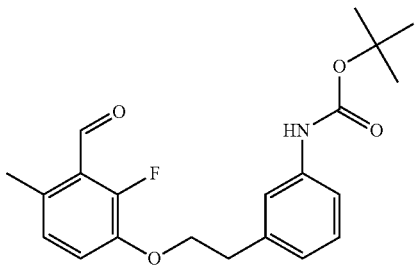 [SMILES: Cc1ccc(OCCc2cccc(NC(=O)OC(C)(C)C)c2)c(F)c1C=O] | 372.0 (M − H) | 2-fluoro-3-hydroxy-6-methylbenzaldehyde |
| 26 | 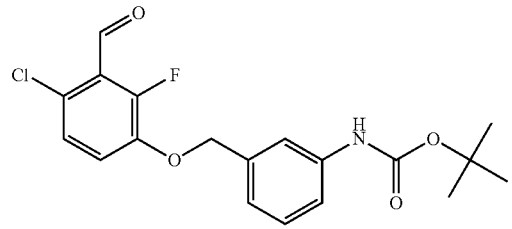 [SMILES: CC(C)(C)OC(=O)Nc1cccc(COc2ccc(Cl)c(C=O)c2F)c1] | 378.0 (M − H) | 6-chloro-2-fluoro-3-hydroxybenzaldehyde |

TABLE 2-continued

Preparations 9-50

| Prep. No. | Structure | ES/MS (m/z) (M + H) | Starting phenol |
|---|---|---|---|
| 27 | 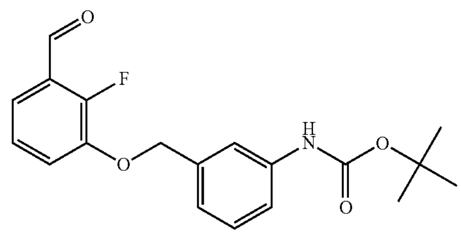 | 246.0 (M + H − Boc) | 2-fluoro-3-hydroxybenzaldehyde |
| 28 | 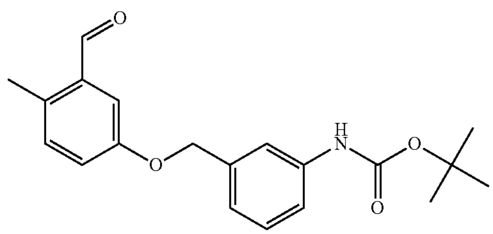 [SMILES: Cc1ccc(OCc2cccc(NC(=O)OC(C)(C)C)c2)cc1C=O] | 340.0 (M − H) | 5-hydroxy-2-methylbenzaldehyde |
| 29 | 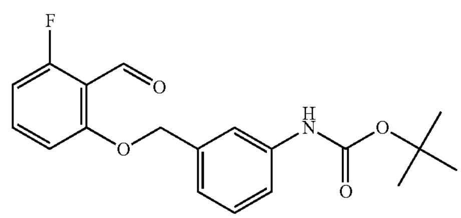 [SMILES: CC(C)(C)OC(=O)Nc1cccc(COc2cccc(F)c2C=O)c1] | 344.0 (M − H) | 2-fluoro-6-hydroxybenzaldehyde |
| 30 | 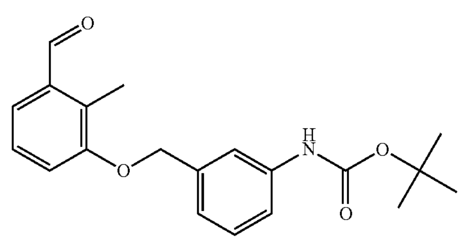 [SMILES: Cc1c(C=O)cccc1OCc1cccc(NC(=O)OC(C)(C)C)c1] | 340.2 (M − H) | 3-hydroxy-2-methylbenzaldehyde |
| 31 | 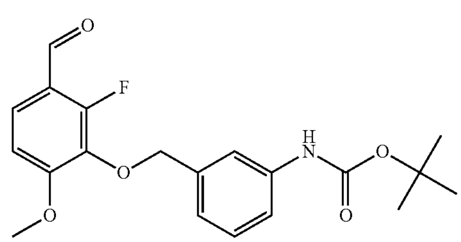 [SMILES: COc1ccc(C=O)c(F)c1OCc1cccc(NC(=O)OC(C)(C)C)c1] | 374.2 (M − H) | 2-fluoro-3-hydroxy-4-methoxybenzaldehyde |
| 32 | 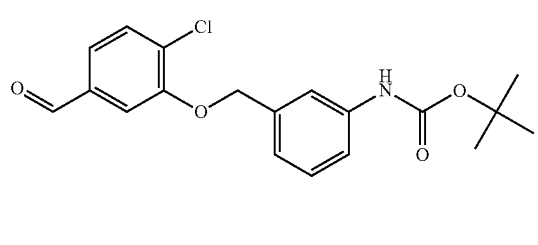 [SMILES: CC(C)(C)OC(=O)Nc1cccc(COc2cc(C=O)ccc2Cl)c1] | 360.0 (M − H) | 4-chloro-3-hydroxybenzaldehyde |

TABLE 2-continued
Preparations 9-50
| Prep. No. | Structure | ES/MS (m/z) (M + H) | Starting phenol |
|---|---|---|---|
| 33 | 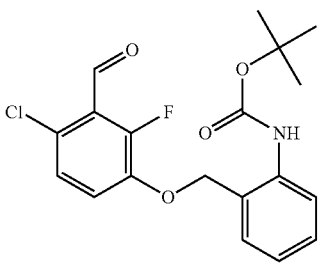 [SMILES: CC(C)(C)OC(=O)Nc1ccccc1COc1ccc(Cl)c(C=O)c1F] | 402.2 (M + Na) | 6-chloro-2-fluoro-3-hydroxybenzaldehyde |
| 34 | 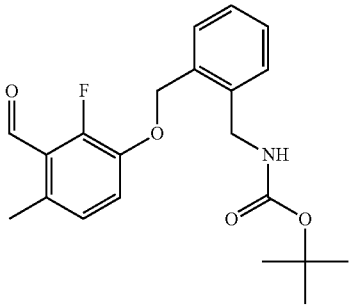 [SMILES: Cc1ccc(OCc2ccccc2CNC(=O)OC(C)(C)C)c(F)c1C=O] | 396.2 (M + Na) | 2-fluoro-3-hydroxy-6-methylbenzaldehyde |
| 35 | 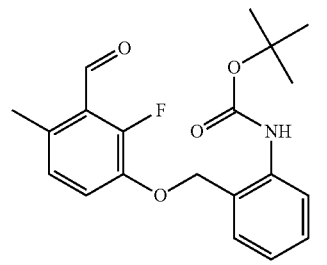 [SMILES: Cc1ccc(OCc2ccccc2NC(=O)OC(C)(C)C)c(F)c1C=O] | 382.2 (M + Na) | 2-fluoro-3-hydroxy-6-methylbenzaldehyde |
| 36 | 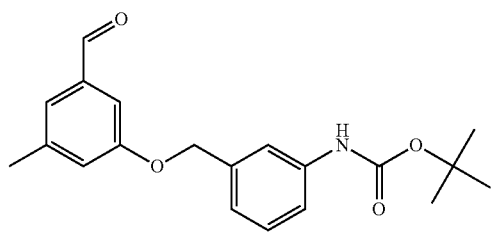 [SMILES: Cc1cc(C=O)cc(OCc2cccc(NC(=O)OC(C)(C)C)c2)c1] | 382.2 (M + Na) | 3-hydroxy-5-methylbenzaldehyde |
| 37 | 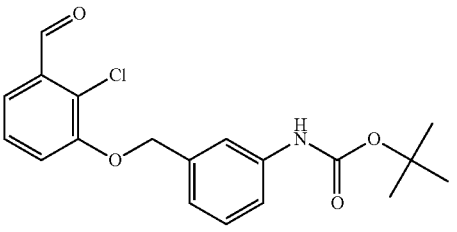 [SMILES: CC(C)(C)OC(=O)Nc1cccc(COc2cccc(C=O)c2Cl)c1] | 379.2 (M + NH$_4$) | 2-chloro-3-hydroxybenzaldehyde |

TABLE 2-continued
Preparations 9-50
| Prep. No. | Structure | ES/MS (m/z) (M + H) | Starting phenol |
|---|---|---|---|
| 38 | 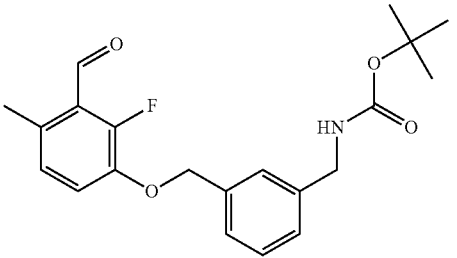 [SMILES: Cc1ccc(OCc2cccc(CNC(=O)OC(C)(C)C)c2)c(F)c1C=O] | 396.2 (M + Na) | 2-fluoro-3-hydroxy-6-methylbenzaldehyde |
| 39 | 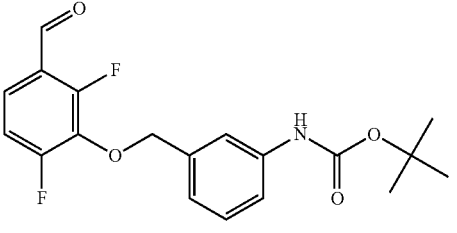 | 396.2 (M + Na) | 2,4-difluoro-3-hydroxybenzaldehyde |
| 40 | 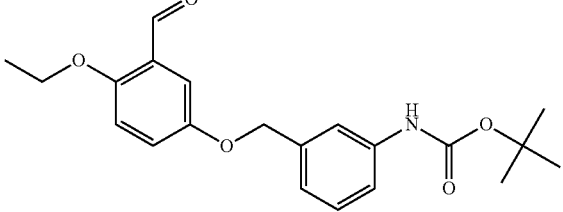 | 370.4 (M − H) | 2-ethoxy-5-hydroxybenzaldehyde |
| 41 | 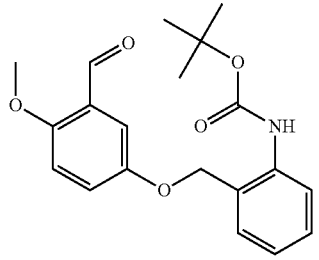 [SMILES: COc1ccc(OCc2ccccc2NC(=O)OC(C)(C)C)cc1C=O] | 356.4 (M − H) | 5-hydroxy-2-methoxybenzaldehyde |
| 42 | 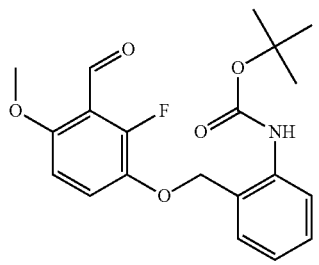 [SMILES: COc1ccc(OCc2ccccc2NC(=O)OC(C)(C)C)c(F)c1C=O] | 374.4 (M − H) | 2-fluoro-3-hydroxy-6-methoxybenzaldehyde |

TABLE 2-continued
Preparations 9-50
| Prep. No. | Structure | ES/MS (m/z) (M + H) | Starting phenol |
|---|---|---|---|
| 43 | 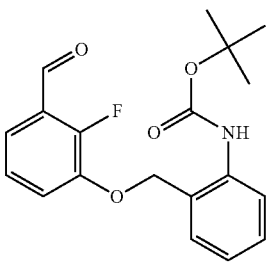 [SMILES: CC(C)(C)OC(=O)Nc1ccccc1COc1cccc(C=O)c1F] | 344.2 (M − H) | 2-fluoro-3-hydroxybenzaldehyde |
| 44 | 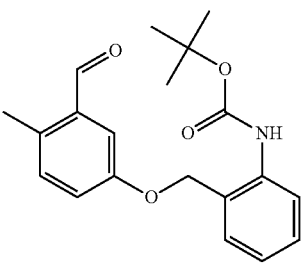 [SMILES: Cc1ccc(OCc2ccccc2NC(=O)OC(C)(C)C)cc1C=O] | 340.2 (M − H) | 5-hydroxy-2-methylbenzaldehyde |
| 45 | 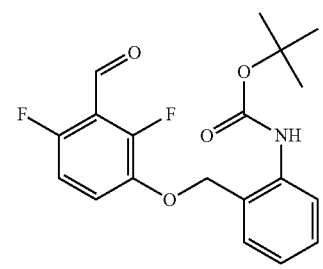 [SMILES: CC(C)(C)OC(=O)Nc1ccccc1COc1ccc(F)c(C=O)c1F] | 362.0 (M + NH$_4$) | 2,6-difluoro-3-hydroxybenzaldehyde |
| 46 | 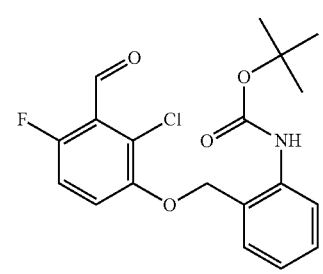 [SMILES: CC(C)(C)OC(=O)Nc1ccccc1COc1ccc(F)c(C=O)c1Cl] | 378.0 (M − H) | 2-chloro-6-fluoro-3-hydroxybenzaldehyde |
| 47 | 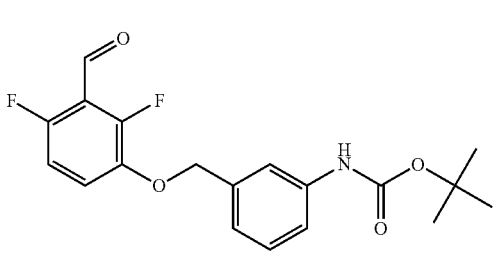 [SMILES: CC(C)(C)OC(=O)Nc1cccc(COc2ccc(F)c(C=O)c2F)c1] | 362.2 (M − H) | 2,6-difluoro-3-hydroxybenzaldehyde |

TABLE 2-continued

Preparations 9-50

| Prep. No. | Structure | ES/MS (m/z) (M + H) | Starting phenol |
|---|---|---|---|
| 48 | 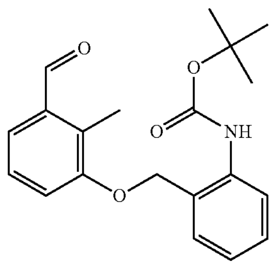 [SMILES: Cc1c(C=O)cccc1OCc1ccccc1NC(=O)OC(C)(C)C] | 340.3 (M − H) | 3-hydroxy-2-methylbenzaldehyde |
| 49 | 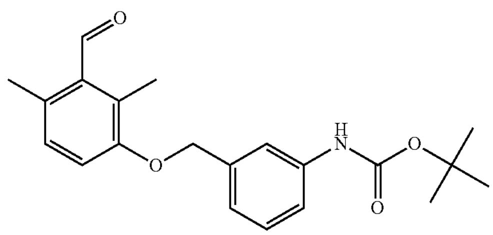 [SMILES: Cc1ccc(OCc2cccc(NC(=O)OC(C)(C)C)c2)c(C)c1C=O] | 372.8 (M + NH$_4$) | 3-hydroxy-2,6-dimethylbenzaldehyde |
| 50 | 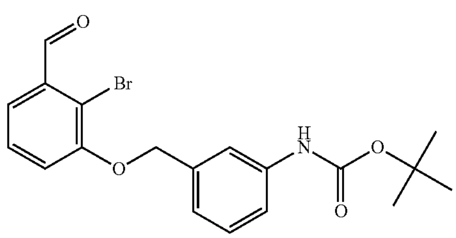 | 406.6 | 2-bromo-3-hydroxybenzaldehyde |

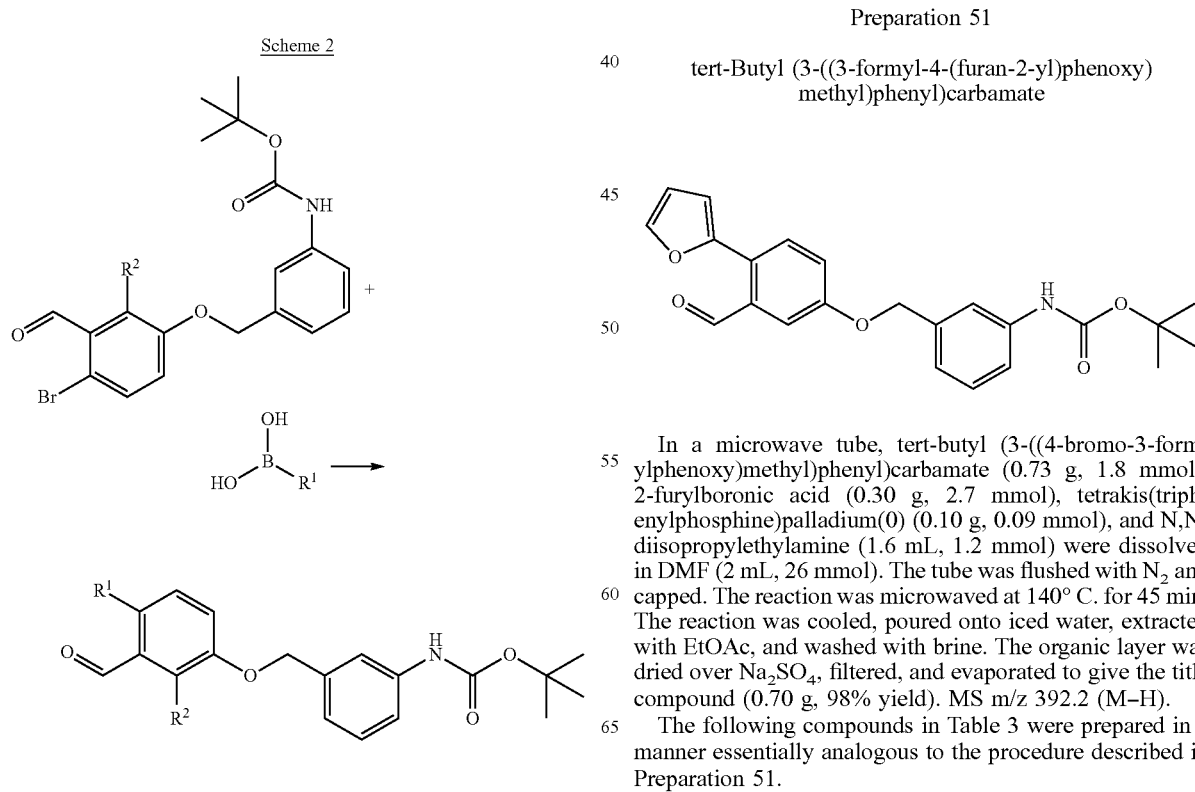

Scheme 2

Preparation 51 tert-Butyl (3-((3-formyl-4-(furan-2-yl)phenoxy)methyl)phenyl)carbamate

In a microwave tube, tert-butyl (3-((4-bromo-3-formylphenoxy)methyl)phenyl)carbamate (0.73 g, 1.8 mmol), 2-furylboronic acid (0.30 g, 2.7 mmol), tetrakis(triphenylphosphine)palladium(0) (0.10 g, 0.09 mmol), and N,N-diisopropylethylamine (1.6 mL, 1.2 mmol) were dissolved in DMF (2 mL, 26 mmol). The tube was flushed with N$_2$ and capped. The reaction was microwaved at 140° C. for 45 min. The reaction was cooled, poured onto iced water, extracted with EtOAc, and washed with brine. The organic layer was dried over Na$_2$SO$_4$, filtered, and evaporated to give the title compound (0.70 g, 98% yield). MS m/z 392.2 (M−H).

The following compounds in Table 3 were prepared in a manner essentially analogous to the procedure described in Preparation 51.

TABLE 3
Preparations 52-55
| Prep. No. | Structure | ES/MS (m/z) (M + H) | Boronic acid |
|---|---|---|---|
| 52 | 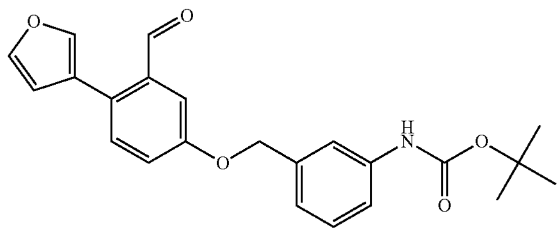 [SMILES: CC(C)(C)OC(=O)Nc1cccc(COc2ccc(-c3ccoc3)c(C=O)c2)c1] | 392.2 | furan-3-ylboronic acid |
| 53 | 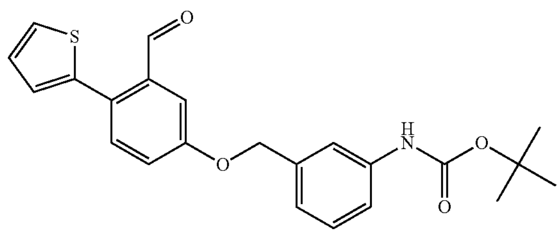 [SMILES: CC(C)(C)OC(=O)Nc1cccc(COc2ccc(-c3cccs3)c(C=O)c2)c1] | 408.4 (M − H) | thiophen-2-ylboronic acid |
| 54 | 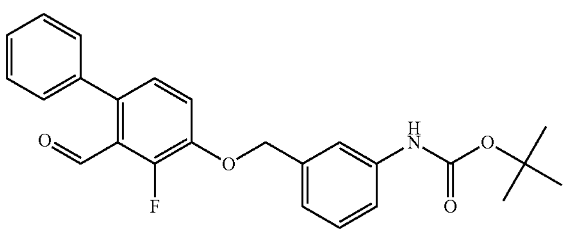 [SMILES: CC(C)(C)OC(=O)Nc1cccc(COc2ccc(-c3ccccc3)c(C=O)c2F)c1] | 420.6 (M − H) | phenylboronic acid |
| 55 | 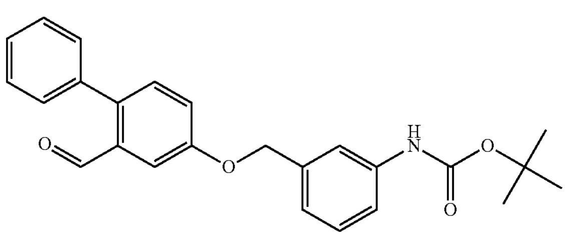 [SMILES: CC(C)(C)OC(=O)Nc1cccc(COc2ccc(-c3ccccc3)c(C=O)c2)c1] | 402.2 (M − H) | phenylboronic acid |
Scheme 3
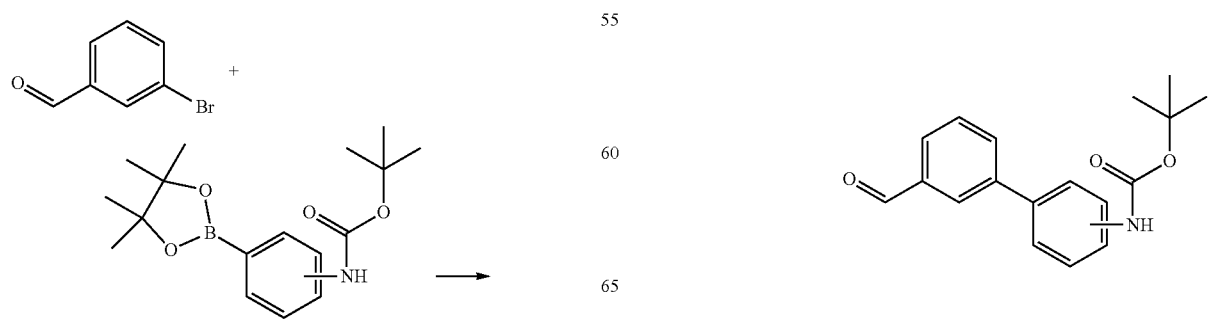

Preparation 56 tert-Butyl (3'-formyl-[1,1'-biphenyl]-3-yl)carbamate

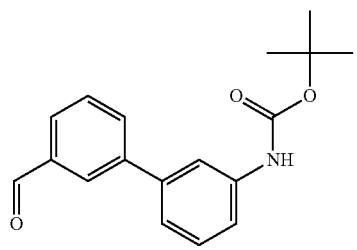 [SMILES: CC(C)(C)OC(=O)Nc1cccc(-c2cccc(C=O)c2)c1]

3-Bromobenzaldehyde (1.5 g, 8.1 mmol), tert-butyl (3-(4,4,5,5-tetramethyl-1,3,2-dioxaborolan-2-yl)phenyl)carbamate (2.1 g, 6.4 mmol), and potassium carbonate (3.3 g, 24 mmol) were dissolved in 1,4 dioxane (11 mL) and water (3 mL) in a 40-mL reaction vial. The resulting homogenous mixture was stirred and degassed three times. 1,1' Bis(di-tert-butylphosphino)ferrocene dichloropalladium(II) dichloromethane complex (530 mg, 0.81 mmol) was added and the mixture was degassed, capped, and heated to 90° C. for 2.25 h. The reaction was cooled, filtered over diatomaceous earth, and the solvent was evaporated. The crude residue was purified by normal phase chromatography, eluting with 7:3 hexanes:EtOAc to give the title compound (1.5 g, 63% yield). MS m/z 315.4 (M+18).

The following compound in Table 4 was prepared in a manner essentially analogous to the procedure described in Preparation 56.

TABLE 4

Preparation 57

| Prep. No. | Structure | ES/MS (m/z) (M + H) | Boronic acid |
|---|---|---|---|
| 57 | 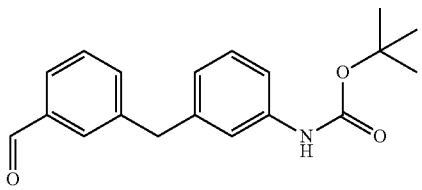 [SMILES: CC(C)(C)OC(=O)Nc1cccc(Cc2cccc(C=O)c2)c1] | 296.2 (M − H) | tert-butyl (4-(4,4,5,5-tetramethyl-1,3,2-dioxaborolan-2-yl)phenyl)carbamate |

Scheme 4

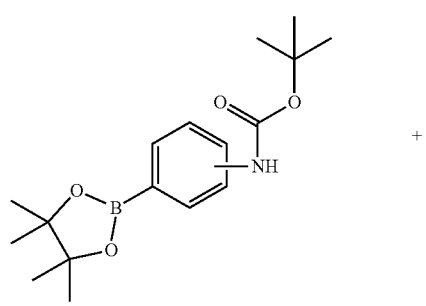

+

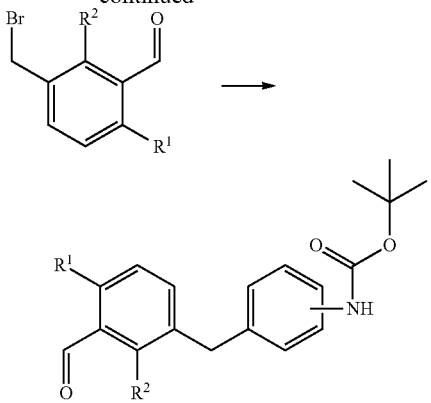

Preparation 58 tert-Butyl (3-(3-formylbenzyl)phenyl)carbamate 3-(Bromomethyl)benzaldehyde (320 mg, 1.5 mmol), tert-butyl (3-(4,4,5,5-tetramethyl-1,3,2-dioxaborolan-2-yl)phenyl)carbamate (300 mg, 0.94 mmol), and potassium carbonate (410 mg, 3.0 mmol) were dissolved in toluene (9 mL) and water (1 mL) in a vial. The reaction was purged with argon. 1,1' Bis(di-tert-butylphosphino)ferrocene dichloropalladium(II) dichloromethane complex (80 mg, 0.10 mmol) was added, the vial was capped and heated to 100° C. for 1.5 h. The reaction was cooled, filtered over diatomaceous earth, and the solvent was evaporated. The crude residue was purified by normal phase chromatography, eluting with 7:3 heptane:EtOAc to give the title compound (300 mg, 54% yield). MS m/z 329.4 (M+18).

The following compounds in Table 5 were prepared in a manner essentially analogous to the procedure described in Preparation 58.

TABLE 5

Preparations 59-60

| Prep. No. | Structure | ES/MS (m/z) (M + H) | Boronic acid/ester |
|---|---|---|---|
| 59 | 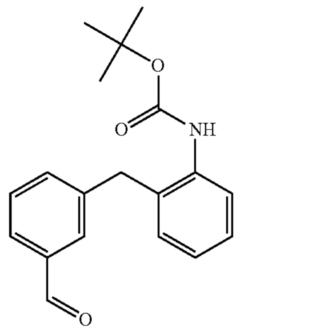 [SMILES: CC(C)(C)OC(=O)Nc1ccccc1Cc1cccc(C=O)c1] | 329.4 (M + NH₄) | tert-butyl (2-(4,4,5,5-tetramethyl-1,3,2-dioxaborolan-2-yl)phenyl) carbamate |
| 60 | 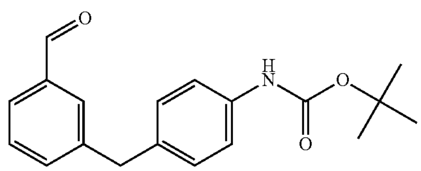 [SMILES: CC(C)(C)OC(=O)Nc1ccc(Cc2cccc(C=O)c2)cc1] | 329.4 (M + NH₄) | tert-butyl (4-(4,4,5,5-tetramethyl-1,3,2-dioxaborolan-2-yl)phenyl) carbamate |

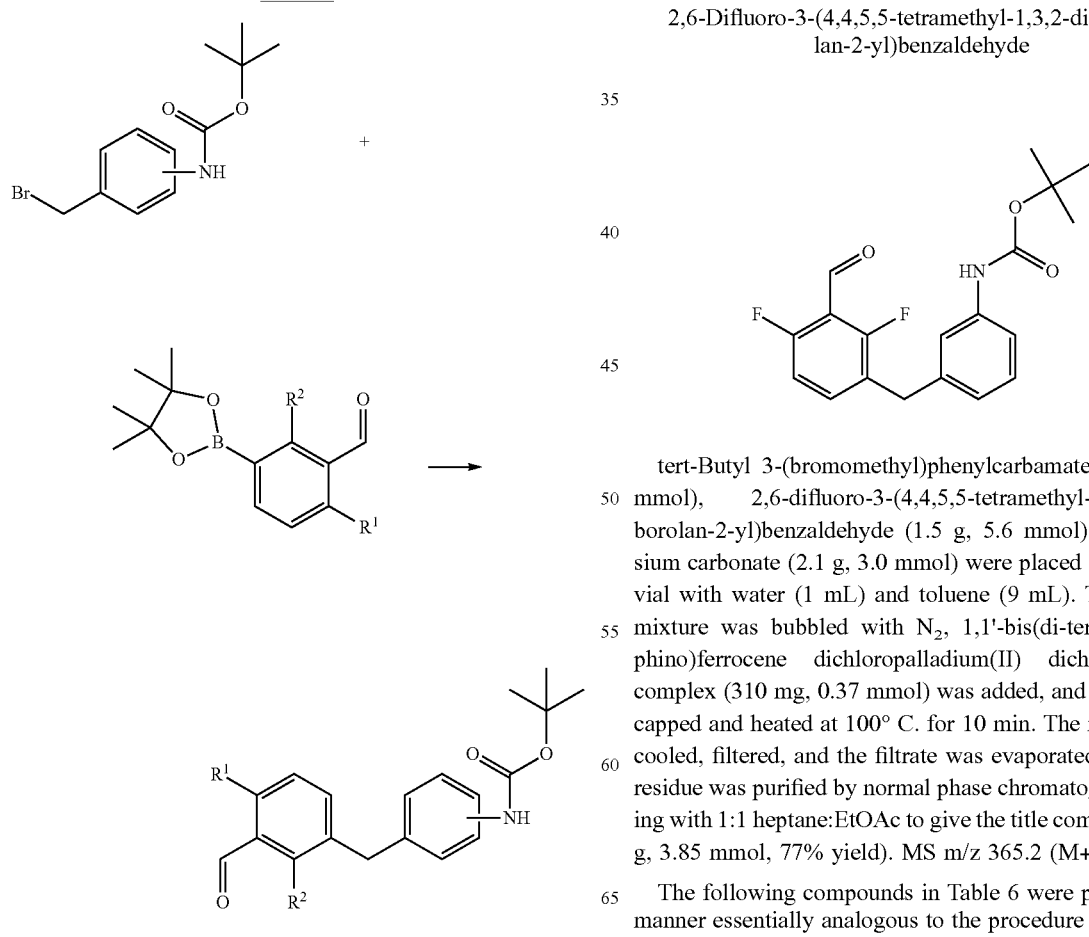

Scheme 5

Preparation 61

2,6-Difluoro-3-(4,4,5,5-tetramethyl-1,3,2-dioxaborolan-2-yl)benzaldehyde tert-Butyl 3-(bromomethyl)phenylcarbamate (1.5 g, 5.0 mmol), 2,6-difluoro-3-(4,4,5,5-tetramethyl-1,3,2-dioxaborolan-2-yl)benzaldehyde (1.5 g, 5.6 mmol), and potassium carbonate (2.1 g, 3.0 mmol) were placed in a reaction vial with water (1 mL) and toluene (9 mL). The reaction mixture was bubbled with N₂, 1,1'-bis(di-tert-butylphosphino)ferrocene dichloropalladium(II) dichloromethane complex (310 mg, 0.37 mmol) was added, and the vial was capped and heated at 100° C. for 10 min. The reaction was cooled, filtered, and the filtrate was evaporated. The crude residue was purified by normal phase chromatography, eluting with 1:1 heptane:EtOAc to give the title compound (1.38 g, 3.85 mmol, 77% yield). MS m/z 365.2 (M+NH₄).

The following compounds in Table 6 were prepared in a manner essentially analogous to the procedure described in Preparation 61.

TABLE 6
Preparations 62-66
| Prep. No. | Structure | ES/MS (m/z) (M + H) | Boronic acid/ester |
|---|---|---|---|
| 62 | 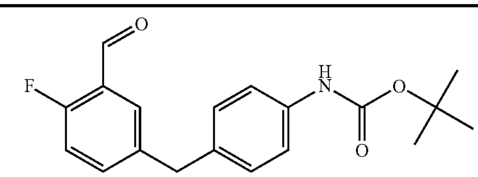 | No ion | 2-fluoro-5-(4,4,5,5-tetramethyl-1,3,2-dioxaborolan-2-yl)benzaldehyde |
| 63 | 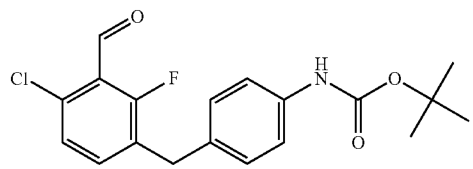 [SMILES: CC(C)(C)OC(=O)Nc1ccc(Cc2ccc(Cl)c(C=O)c2F)cc1] | 381.0 (M + NH₄) | (4-chloro-2-fluoro-3-formylphenyl) boronic acid |
| 64 | 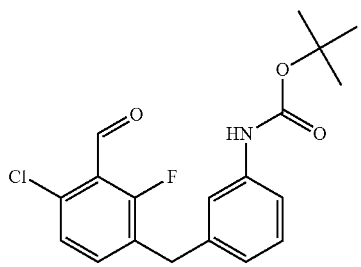 [SMILES: CC(C)(C)OC(=O)Nc1cccc(Cc2ccc(Cl)c(C=O)c2F)c1] | 381.2 (M + NH₄) | (4-chloro-2-fluoro-3-formylphenyl) boronic acid |
| 65 | 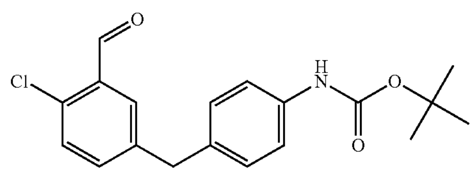 [SMILES: CC(C)(C)OC(=O)Nc1ccc(Cc2ccc(Cl)c(C=O)c2)cc1] | 363.2 (M + NH₄) | (4-chloro-3-formylphenyl) boronic acid |
| 66 | 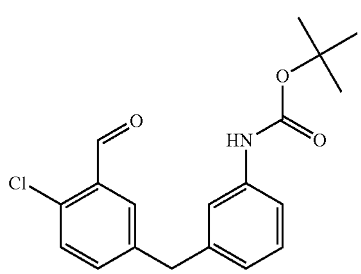 [SMILES: CC(C)(C)OC(=O)Nc1cccc(Cc2ccc(Cl)c(C=O)c2)c1] | 363.2 (M + H) | (4-chloro-3-formylphenyl) boronic acid |
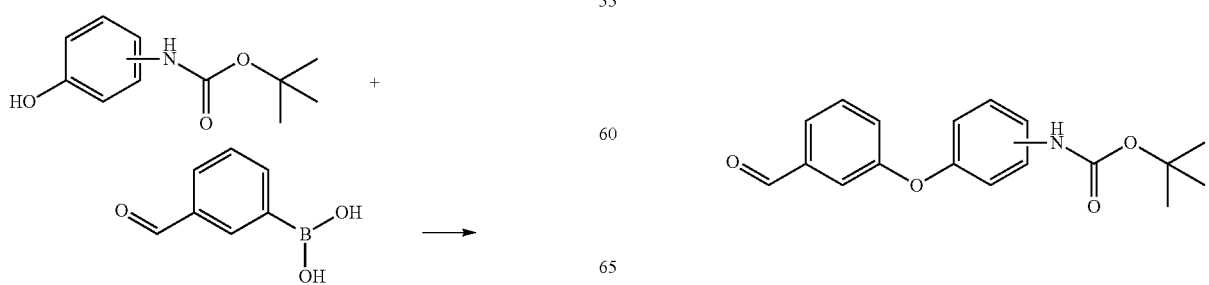
Scheme 6

Preparation 67 tert-Butyl (4-(3-formylphenoxy)phenyl)carbamate

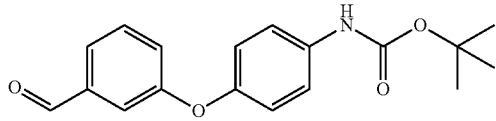 [SMILES: CC(C)(C)OC(=O)Nc1ccc(Oc2cccc(C=O)c2)cc1]

(3-Formylphenyl)boronic acid (610 mg, 4.1 mmol), tert-butyl (4-hydroxyphenyl)carbamate (420 mg, 2.0 mmol), copper(II) acetate (370 mg, 2.0 mmol), triethylamine (1.4 mL, 10 mmol), and 4 Å molecular sieves (500 mg) were added in DCM (15 mL) in a vial. The reaction was incubated at rt for 10 h. The reaction was filtered over diatomaceous earth and the solvent was evaporated. The crude residue was purified by normal phase chromatography, eluting with 7:3 hexanes:EtOAc to give the title compound (180 mg, 29% yield). MS m/z 312.2 (M–H).

The following compounds in Table 7 were prepared in a manner essentially analogous to the procedure described in Preparation 67.

TABLE 7

| | Preparation 68 | | |
|---|---|---|---|
| Prep. No. | Structure | ES/MS (m/z) (M + H) | Phenol |
| 68 | 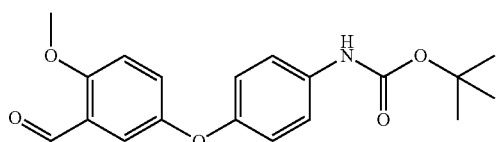 | 312.2 (M − H) | tert-butyl (3-hydroxyphenyl)carbamate |

Scheme 7

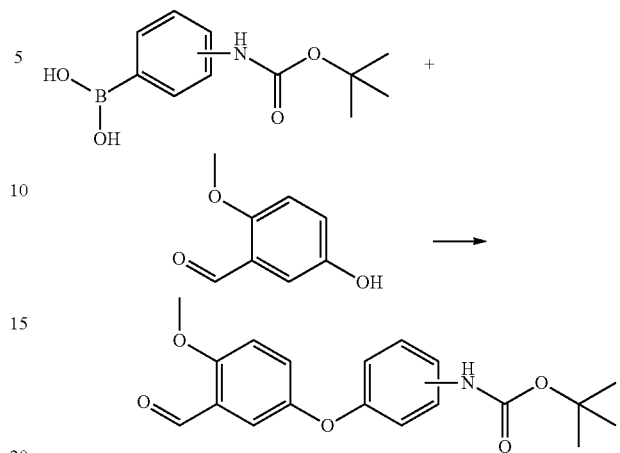

Preparation 69 tert-Butyl (4-(3-formylphenoxy)phenyl)carbamate

5-Hydroxy-2-methoxybenzaldehyde (1.00 g, 6.57 mmol), [4-(tert-butoxycarbonylamino)phenyl]boronic acid (3.12 g, 13.2 mmol), copper(II) acetate (1.19 g, 6.57 mmol), and 4 Å molecular sieves (1.0 g) were added to a flask. DCM (60 mL) and triethylamine (4.6 mL, 33 mmol) were then added. The reaction mixture was stirred at rt overnight. More [4-(tert-butoxycarbonylamino)phenyl]boronic acid (1.1 g, 4.6 mmol) and copper(II) acetate (400 mg, 2.2 mmol) were added and the reaction mixture was stirred at rt for three days. The reaction was filtered and the solvent was evaporated. The crude residue was purified by normal phase chromatography, eluting with heptane:EtOAc to give the title compound (400 mg, 18% yield). MS m/z 361.0 (M+NH$_4$).

The following compounds in Table 8 were prepared in a manner essentially analogous to the procedure described in Preparation 69.

TABLE 8

| | Preparation 70 | | |
|---|---|---|---|
| Prep. No. | Structure | ES/MS (m/z) (M + H) | Boronic acid |
| 70 | | 361.0 (M + NH$_4$) | [3-(tert-butoxycarbonylamino)phenyl]boronic acid |

Preparation 71 tert-Butyl (3-((2-fluoro-3-formylphenyl)ethynyl)phenyl)carbamate

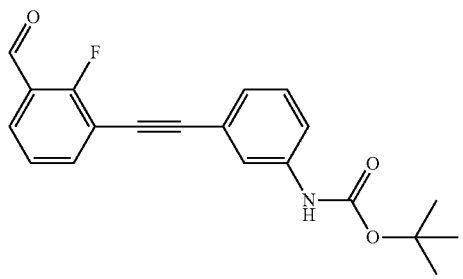 [SMILES: CC(C)(C)OC(=O)Nc1cccc(C#Cc2cccc(C=O)c2F)c1]

3-Ethynyl-2-fluorobenzaldehyde (0.25 g, 1.7 mmol) was mixed with tert-butyl N-(3-iodophenyl)carbamate (0.55 g, 1.7 mmol), bis(triphenylphosphine)palladium(II) dichloride (0.025 g, 0.036 mmol), and copper(I) iodide (0.01 g., 0.05 mmol) in triethylamine (10 mL, 72 mmol) under $N_2$. The reaction mixture was stirred at rt overnight. The reaction mixture was diluted with EtOAc and filtered through diatomaceous earth. The filtrate was washed with 1 M aq HCl, brine, dried over $Na_2SO_4$, and filtered. The solvent was evaporated to give the title compound (0.57 g, 100% yield). MS m/z 338.2 (M−H).

Scheme 8

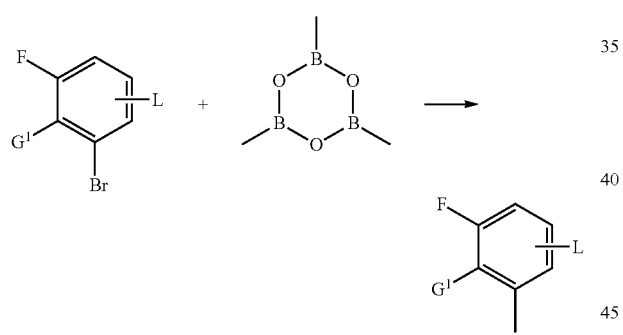

Wherein $G^1$ is

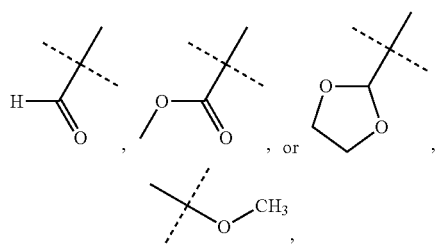

, or

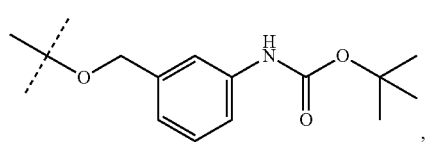

,

Wherein L is

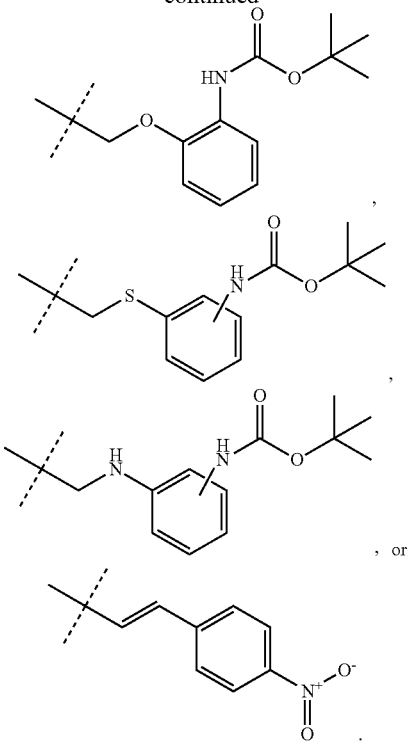

Preparation 72

2-(6-Fluoro-3-methoxy-2-methylphenyl)-1,3-dioxolane

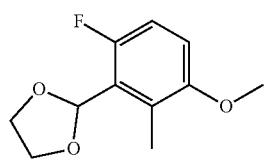

To a microwave vial, added 2-(2-bromo-6-fluoro-3-methoxyphenyl)-1,3-dioxolane (970 mg, 3.5 mmol), trimethylboroxine (50 mass %) in THF (600 μL, 4.3 mmol), and cesium carbonate (2.3 g, 7.1 mmol) in 1,4-dioxane (12 mL, 140 mmol) and water (2 mL, 110 mmol). Degassed the solution with $N_2$ for 2 min. [1,1'-Bis(diphenylphosphino)ferrocene]dichloro palladium(II) (130 mg, 0.17 mmol) was added and degassed the solution with $N_2$ for 2 min. The vial was capped and microwaved at 110° C. for 1 h. The reaction mixture was diluted with water (10 mL) and extracted with EtOAc (10 mL). The organic layer was dried with $Na_2SO_4$, filtered through paper, and rotary evaporated to a crude oil. The crude oil was purified by normal phase chromatography, eluting with 7:3 hexanes:MTBE to give the title compound (0.61 g, 82% yield). MS m/z 212.8 (M+H).

The following compounds in Table 9 were prepared in a manner essentially analogous to the procedure described in Preparation 72.

TABLE 9

| Prep. No. | Structure | ES/MS (m/z) (M + H) | Bromide |
|---|---|---|---|
| 73 | 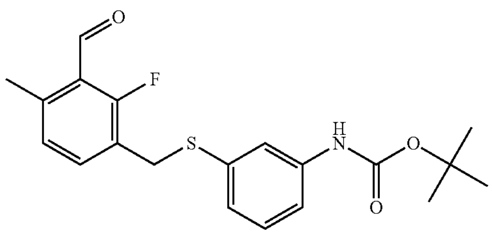 [SMILES: Cc1ccc(CSc2cccc(NC(=O)OC(C)(C)C)c2)c(F)c1C=O] | No ion* | tert-butyl (3-((4-bromo-2-fluoro-3-formylbenzyl)thio)phenyl)carbamate |
| 74 | 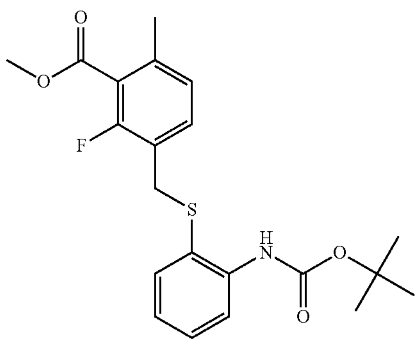 [SMILES: COC(=O)c1c(C)ccc(CSc2ccccc2NC(=O)OC(C)(C)C)c1F] | 305.9 (M − Boc + H) | methyl 6-bromo-3-(((2-((tert-butoxycarbonyl)amino)phenyl)thio)methyl)-2-fluorobenzoate |
| 75 | 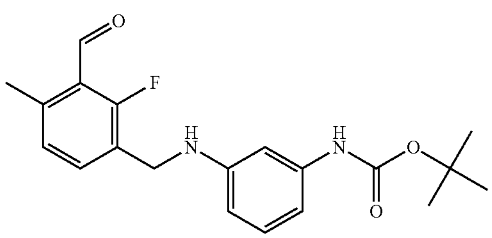 [SMILES: Cc1ccc(CNc2cccc(NC(=O)OC(C)(C)C)c2)c(F)c1C=O] | 359.0 | tert-butyl (3-((4-bromo-2-fluoro-3-formylbenzyl)amino)phenyl)carbamate |
| 76 | 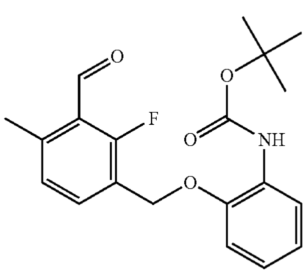 [SMILES: Cc1ccc(COc2ccccc2NC(=O)OC(C)(C)C)c(F)c1C=O] | No ion** | tert-butyl (2-((4-bromo-2-fluoro-3-formylbenzyl)oxy)phenyl)carbamate |
| 77 | 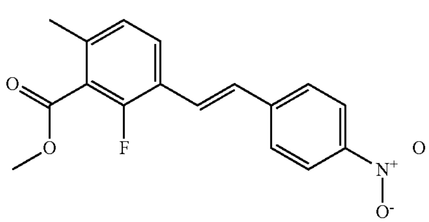 | 315.9 | methyl (E)-6-bromo-2-fluoro-3-(4-nitrostyryl)benzoate |

TABLE 9-continued

Preparations 73-78

| Prep. No. | Structure | ES/MS (m/z) (M + H) | Bromide |
|---|---|---|---|
| 78 | 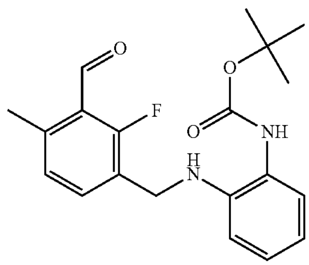 [SMILES: Cc1ccc(CNc2ccccc2NC(=O)OC(C)(C)C)c(F)c1C=O] | 359.0 | tert-butyl (2-((4-bromo-2-fluoro-3-formylbenzyl)amino)phenyl)carbamate |

*¹H NMR (400.14 MHz, DMSO): δ 10.40 (s, 1H), 9.39 (s, 1H), 7.55-7.50 (m, 2H), 7.26 (d, J = 8.3 Hz, 1H), 7.19 (t, J = 7.9 Hz, 1H), 7.08 (d, J = 7.9 Hz, 1H), 6.96 (d, J = 7.8 Hz, 1H), 4.22 (s, 2H), 1.46 (s, 10H)
**¹H NMR (400.21 MHz, DMSO): δ 10.45 (s, 1H), 7.97 (s, 1H), 7.78 (t, J = 7.8 Hz, 1H), 7.65-7.61 (m, 1H), 7.22-7.20 (m, 1H), 7.14-7.12 (m, 1H), 7.07-7.02 (m, 1H), 6.95-6.91 (m, 1H), 5.21 (s, 2H), 2.57 (s, 3H), 1.43 (s, 9H)

Preparation 79

6-Fluoro-3-hydroxy-2-methylbenzaldehyde

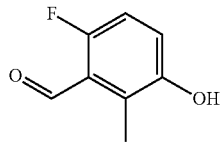

Boron tribromide in DCM (14 mL, 14 mmol, 1 mol/L) was added over a period of 2 min to a solution of 2-(6-fluoro-3-methoxy-2-methylphenyl)-1,3-dioxolane (600 mg, 2.8 mmol) in DCM (14 mL, 220 mmol) cooled to 0° C. The bath was removed after the addition. After 30 min, the reaction was quenched with satd aq NH₄Cl. The reaction was diluted with DCM, washed with 2 M aq NaOH, and then washed with 5 M aq HCl. The organic layer was dried with Na₂SO₄, filtered through paper, and rotary evaporated to a crude residue. The crude residue was purified by normal phase chromatography, eluting with 7:3 hexanes:EtOAc to give the title compound (130 mg, 30% yield). MS m/z 153.0 (M−H).

Preparation 80 tert-Butyl (4-fluoro-2-methoxyphenoxy)diphenylsilane

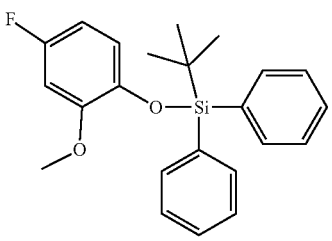 [SMILES: COc1cc(F)ccc1O[Si](c1ccccc1)(c1ccccc1)C(C)(C)C]

To a solution of 4-fluoro-2-methoxy-phenol (2.3 g, 16 mmol) in DCM (35 mL) was added imidazole (2.8 g, 41 mmol) and tert-butylchlorodiphenylsilane (6 mL, 23 mmol). After 1.75 h, the solvent was evaporated, and the residue was partitioned between 200 mL of 10% EtOAc in hexanes and 100 mL water. The organics were washed once with brine, dried over MgSO₄, filtered, and evaporated. The crude residue was purified by normal phase chromatography, eluting with 9:1 hexanes:EtOAc to give the title compound (6.7 g, quantitative yield). ¹H NMR (399.8 MHz, d₆-DMSO) δ7.64 (dd, J=1.5, 7.9 Hz, 4H), 7.48-7.43 (m, 6H), 6.82 (dd, J=2.9, 10.5 Hz, 1H), 6.60 (dd, J=5.9, 8.8 Hz, 1H), 6.48 (td, J=8.5, 3.0 Hz, 1H), 3.56 (s, 3H), 1.05 (s, 9H)

Preparation 81

6-Fluoro-3-hydroxy-2-methoxybenzaldehyde

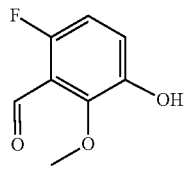

tert-Butyl (4-fluoro-2-methoxyphenoxy)diphenylsilane (3.2 g, 8.5 mmol) was dissolved in tetrahydrofuran (30 mL) and cooled to −78° C. n-Butyllithium (7 mL, 11 mmol, 1.6 III) was added over 3 minutes. After 1.5 h, DMF (2 mL) was added at −78° C. After 1 h, added about 4 mL of 10% aq NH₄Cl and warmed to rt over 1.5 h. Evaporated the solvent to a crude residue, then made acidic with 1 M aq HCl, and partitioned between water and 300 mL EtOAc. The organic layer was washed with water, brine, dried over MgSO₄, filtered, and evaporated. The crude residue was purified by normal phase chromatography, eluting with 3:2 hexanes: EtOAc to give the title compound (0.79 g, 55% yield). MS m/z 171.0 (M+H).

Preparation 82 tert-Butyl (3-((4-cyclopropyl-3-(1,3-dioxolan-2-yl)-2-fluorophenoxy)methyl)phenyl)carbamate

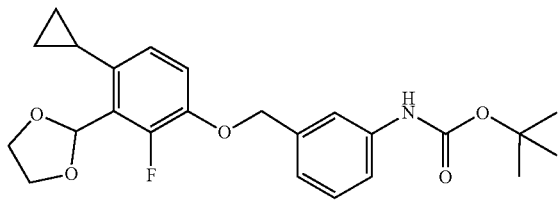 [SMILES: CC(C)(C)OC(=O)Nc1cccc(COc2ccc(C3CC3)c(C3OCCO3)c2F)c1]

tert-Butyl (3-((4-bromo-3-(1,3-dioxolan-2-yl)-2-fluorophenoxy)methyl)phenyl)carbamate (200 mg, 0.43 mmol), cyclopropyl boronic acid (0.21 g, 2.4 mmol), and potassium phosphate tribasic (0.28 g, 1.3 mmol) were placed in a 25 mL vial purged with $N_2$. Toluene (3 mL) and water (0.75 mL) were added. The reaction mixture was degassed with $N_2$ for 5 min and then tetrakis(triphenylphosphine)palladium (0) (0.10 g, 0.09 mmol) was added in one portion. The reaction was heated to 100° C. overnight. Upon cooling to rt, EtOAc and water were added; the phases were separated, and the aqueous layer was extracted twice with EtOAc. The combined organic layers were dried over $Na_2SO_4$, filtered, and concentrated to a crude residue. The crude residue was purified by normal phase chromatography, eluting with 1:1 hexanes:EtOAc to give the title compound (170 mg, 94% yield). MS m/z 428.4 (M−H).

Preparation 83

(2,6-Dimethyl-3-nitrophenyl)methylene diacetate

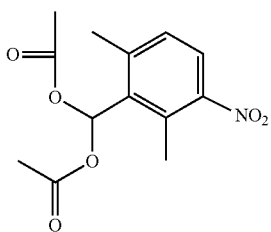 [SMILES: CC(=O)OC(OC(C)=O)c1c(C)ccc([N+](=O)[O-])c1C]

2,6-Dimethyl-3-nitrobenzaldehyde (1.9 g, 10 mmol) was dissolved in DCM (23 mL), then acetic anhydride (1.3 mL, 14 mmol) and copper(II) trifluoromethanesulfonate (41 mg, 0.11 mmol) were added. The solution was stirred at rt for 3.5 h. The reaction was quenched with satd aq $NaHCO_3$. The organic layer was separated, washed with water, brine, dried over $Na_2SO_4$, filtered, and concentrated to a crude residue. The crude residue was purified by normal phase chromatography, eluting with 3:2 hexanes:EtOAc to give the title compound (2.4 g, 81% yield). $^1H$ NMR (400.13 MHz, DMSO-d6): 7.96 (s, 1H), 7.80 (d, J=8.3 Hz, 1H), 7.35 (d, J=8.4 Hz, 1H), 2.58 (s, 3H), 2.53 (s, 2H), 2.12 (s, 6H).

Preparation 84

(3-Amino-2,6-dimethylphenyl)methylene diacetate

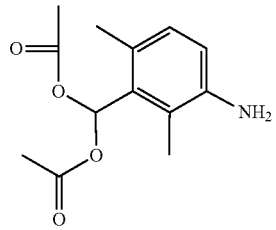 [SMILES: CC(=O)OC(OC(C)=O)c1c(C)ccc(N)c1C]

Sulfided 5 wt % platinum on carbon (1.0 g, 5.2 mmol) was added to a 500-mL Parr shaker bottle and degassed with $N_2$. Added 25 mL EtOAc, then added (2,6-dimethyl-3-nitrophenyl)methylene diacetate (2.7 g, 9.6 mmol) in 25 mL EtOAc to the bottle. The bottle was sealed, purged with $N_2$, purged with $H_2$, and pressurized to 60 psi $H_2$ for 1.5 h at rt. The reaction mixture was filtered and concentrated to give the title compound (2.1 g, quant yield). MS m/z 251.8 (M+H).

Preparation 85

(3-((3-((tert-Butoxycarbonyl)amino)benzyl)amino)-2,6-dimethylphenyl)methylene diacetate A mixture of (3-amino-2,6-dimethylphenyl)methylene diacetate (276 mg, 1.10 mmol) and potassium carbonate (435 mg, 3.15 mmol) in DMF (3 mL) was stirred at rt for 1 h. tert-Butyl N-[3-(bromomethyl)phenyl]carbamate (300 mg, 1.05 mmol) was added to the slurry and the reaction was stirred at 50° C. for 1 h. After cooling, the reaction mixture was partitioned between ethyl acetate and water. The phases were separated. The organic phase was transferred to a round-bottom flask, and the solvent evaporated in vacuo. Residual DMF was evaporated (azeotroped) with xylenes giving residue as a clear paste. The crude residue was purified by normal phase purification, eluting with 1:1 EtOAc:hexanes to give the title compound (363 mg, 76% yield). MS m/z 457.2 (M+H).

Scheme 9

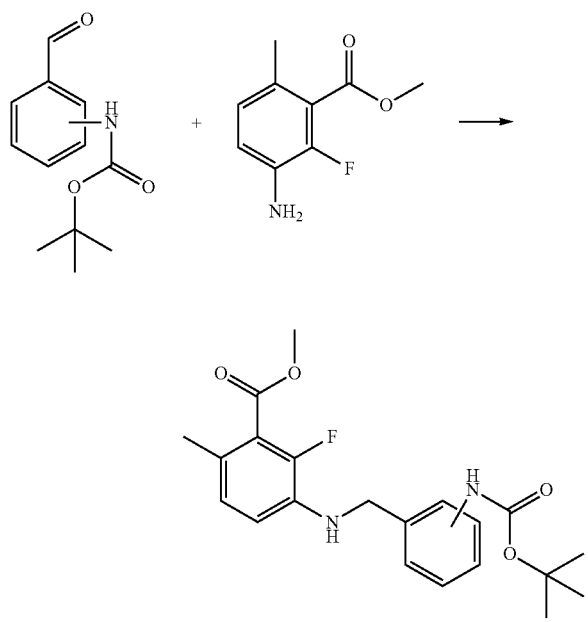

tert-Butyl (3-formylphenyl)carbamate (1.2 g, 5.2 mmol), methyl 3-amino-2-fluoro-6-methylbenzoate (950 mg, 4.8 mmol), and acetic acid (0.55 mL, 9.6 mmol) was dissolved in methanol (5 mL) and cooled to 0° C. Sodium cyanoborohydride (0.61 g, 9.5 mmol) was carefully added into the solution. The ice bath was removed, and the reaction mixture stirred at rt overnight under $N_2$. The reaction was quenched by addition of water (10 mL). The reaction mixture was partitioned between EtOAc and water. The combined organic extracts were washed with brine, dried with $Na_2SO_4$, filtered, and concentrated to a crude residue. The crude residue was purified by normal phase chromatography, eluting with 3:2 Pet ether:EtOAc to give the title compound (1.9 g, 75% yield). MS m/z 389.0 (M+H).

The following compound in Table 10 was prepared in a manner essentially analogous to the procedure described in Preparation 86.

TABLE 10

| Preparation 87 | | | |
|---|---|---|---|
| Prep. No. | Structure | ES/MS (m/z) (M + H) | Formyl starting material |
| 87 |  | 389.0 | tert-butyl (2-formylphenyl) carbamate |

Preparation 86

Methyl 3-((3-((tert-butoxycarbonyl)amino)benzyl)amino)-2-fluoro-6-methylbenzoate

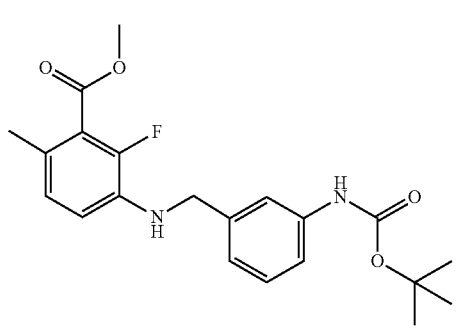

Preparation 88

Methyl 6-bromo-2-fluoro-3-formylbenzoate

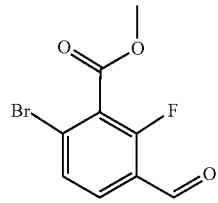

N-Bromosuccinimide (5.8 g, 31 mmol) was added to a solution of methyl 6-bromo-2-fluoro-3-methylbenzoate (3.9 g, 14 mmol) in carbon tetrachloride (36 mL), followed by 2,2'-azobis(2-methylpropionitrile (0.24 g, 1.4 mmol), and the reaction mixture was stirred at 85° C. overnight. The mixture was diluted with DCM, washed with brine, dried over Na₂SO₄, and concentrated to a crude residue. The residue was dissolved in ACN and purified by preparative C18 HPLC (35%-60% water [0.225% FA]-ACN). The eluent was concentrated to give methyl 6-bromo-3-(dibromomethyl)-2-fluorobenzoate (1.9 g, 4.6 mmol). The material was dissolved in ethanol (15 mL). A mixture of silver nitrate (2.0 g, 12 mmol) in water (10 mL) was added and the reaction mixture was heated at 75° C. for 6 h under N₂. The reaction mass was filtered and washed with EtOAc. The filtrate was concentrated to giver a crude residue. The crude residue was purified by normal phase chromatography, eluting with 8% EtOAc:Pet ether to give the title compound (1.1 g, 91% yield).

Scheme 10

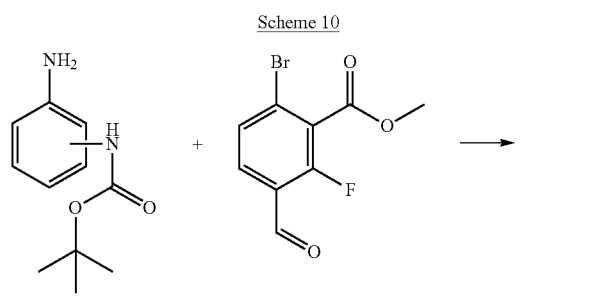

Preparation 89

Methyl 6-bromo-3-(((3-((tert-Butoxycarbonyl)amino)phenyl)amino)methyl)-2-fluorobenzoate

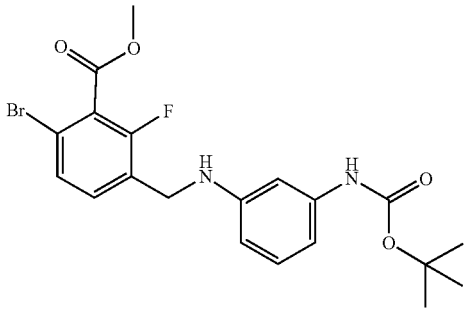 [SMILES: COC(=O)c1c(Br)ccc(CNc2cccc(NC(=O)OC(C)(C)C)c2)c1F]

Methyl 6-bromo-2-fluoro-3-formylbenzoate (1.0 g, 3.7 mmol), tert-butyl N-(3-aminophenyl)carbamate (870 mg, 4.1 mmol), and acetic acid (0.43 mL, 7.5 mmol) were dissolved in methanol (9 mL) and cooled to 0° C. Sodium cyanoborohydride (480 mg, 7.5 mmol) was carefully added into the solution. The ice bath was removed, and the reaction mixture stirred at rt overnight under N₂. The reaction was quenched by addition of water (30 mL). The reaction mixture was partitioned between EtOAc and water. The combined organic extracts were washed with brine, dried with Na₂SO₄, filtered, and concentrated to a crude residue. The crude residue was purified by normal phase chromatography, eluting with 7:3 Pet ether:EtOAc to give the title compound (1.7 g, 89% yield). MS m/z 454.9 (M+H).

The following compound in Table 11 was prepared in a manner essentially analogous to the procedure described in Preparation 89.

TABLE 11

| Prep. No. | Structure | ES/MS (m/z) (M + H) | Formyl starting material |
|---|---|---|---|
| 90 | 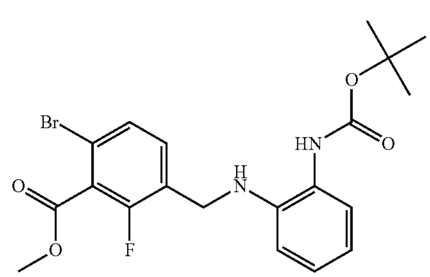 [SMILES: COC(=O)c1c(Br)ccc(CNc2ccccc2NC(=O)OC(C)(C)C)c1F] | 454.9 | methyl 6-bromo-2-fluoro-3-formylbenzoate |

Preparation 91

Methyl 3-((3-((tert-butoxycarbonyl)amino)benzyl)(methyl)amino)-2-fluoro-6-methylbenzoate

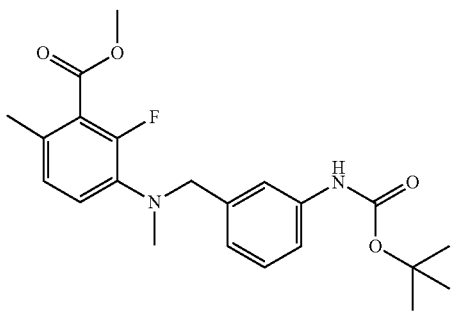

To a solution of methyl 3-((3-((tert-butoxycarbonyl)amino)benzyl)amino)-2-fluoro-6-methylbenzoate (1.7 g, 3.3 mmol) in methanol (5 mL) was added sodium cyanoborohydride (420 mg, 6.5 mmol) and acetic acid (0.5 mL, 9 mmol). Formaldehyde in water (730 μL, 9.8 mmol, 37 mass %) was then added at 25° C. The mixture was stirred at rt overnight under $N_2$. The crude mixture was purified by normal phase chromatography, eluting with 4:1 Pet ether:EtOAc to give the title compound (1.3 g, 92% yield). MS m/z 403.0 (M+H).

Scheme 11

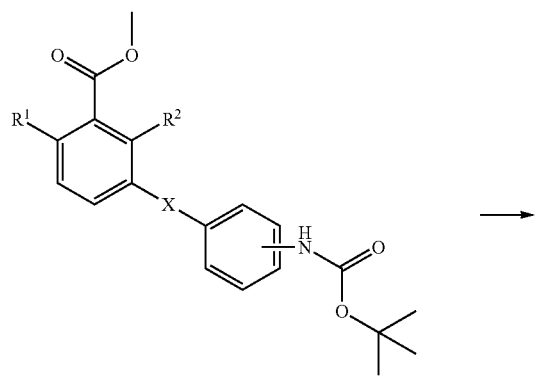

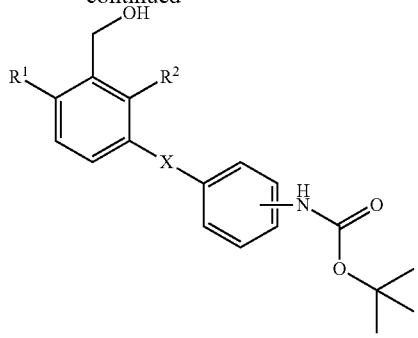

Preparation 92 tert-Butyl (3-(((2-fluoro-3-(hydroxymethyl)-4-methylphenyl)(methyl)amino)methyl)phenyl)carbamate

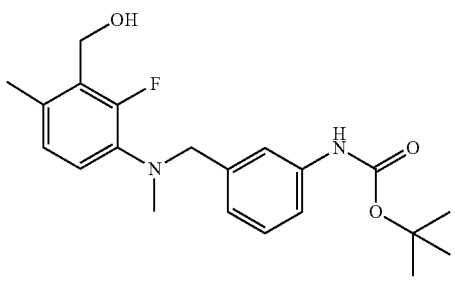 [SMILES: Cc1ccc(N(C)Cc2cccc(NC(=O)OC(C)(C)C)c2)c(F)c1CO]

To a solution methyl 3-((3-((tert-butoxycarbonyl)amino)benzyl)(methyl)amino)-2-fluoro-6-methylbenzoate (1.2 g, 2.8 mmol) in DCM (10 mL) was added DIBAL-H in toluene (7 mL, 7.0 mmol, 1.0 mol/L) at 0° C. The reaction mixture was warmed to rt for 3 h. The solution was cooled back to 0° C. and satd aq Rochelle salt and DCM were added, followed by extraction with DCM. The organic layer was washed with brine, dried over $Na_2SO_4$, passed through a silica gel plug, and concentrated to a crude residue. The residue was purified by normal phase chromatography, eluting with 1:1 Pet ether:EtOAc to give the title compound (640 mg, 57% yield). MS m/z 375.0 (M+H). The following compounds in Table 12 were prepared in a manner essentially analogous to the procedure described in Preparation 92.

TABLE 12

Preparations 93-98

| Prep. No. | Structure | ES/MS (m/z) (M + H) | Ester SM |
|---|---|---|---|
| 93 | ![structure] | 278.0 (M − Boc + H) | methyl 3-(((2-((tert-butoxycarbonyl)amino)phenyl)thio)methyl)-2-fluoro-6-methylbenzoate |

TABLE 12-continued

Preparations 93-98

| Prep. No. | Structure | ES/MS (m/z) (M + H) | Ester SM |
|---|---|---|---|
| 94 | 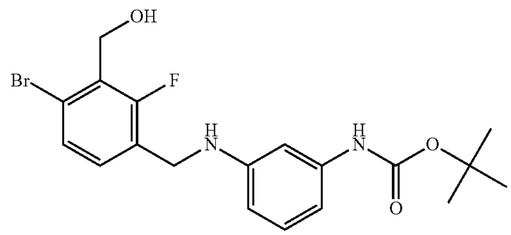 [SMILES: CC(C)(C)OC(=O)Nc1cccc(NCc2ccc(Br)c(CO)c2F)c1] | 426.9 | methyl 6-bromo-3-(((3-((tert-butoxycarbonyl)amino)phenyl)amino)methyl)-2-fluorobenzoate |
| 95 | 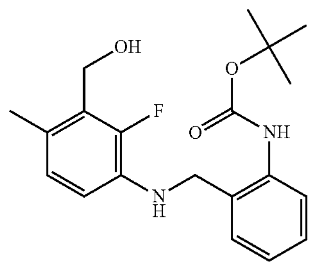 [SMILES: Cc1ccc(NCc2ccccc2NC(=O)OC(C)(C)C)c(F)c1CO] | 361.0 | methyl 3-((2-((tert-butoxycarbonyl)amino)benzyl)amino)-2-fluoro-6-methylbenzoate |
| 96 | 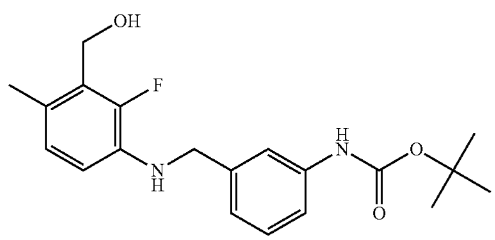 [SMILES: Cc1ccc(NCc2cccc(NC(=O)OC(C)(C)C)c2)c(F)c1CO] | 361.2 | methyl 3-((3-((tert-butoxycarbonyl)amino)benzyl)amino)-2-fluoro-6-methylbenzoate |
| 97 | 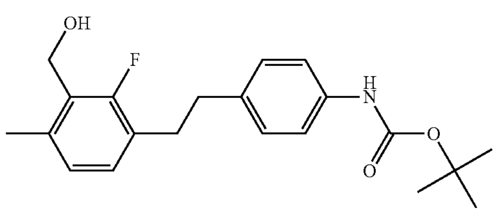 [SMILES: Cc1ccc(CCc2ccc(NC(=O)OC(C)(C)C)cc2)c(F)c1CO] | No ion* | methyl 3-(4-((tert-butoxycarbonyl)amino)phenethyl)-2-fluoro-6-methylbenzoate |
| 98 | 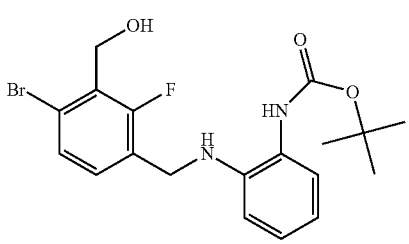 [SMILES: CC(C)(C)OC(=O)Nc1ccccc1NCc1ccc(Br)c(CO)c1F] | 426.9 | methyl 6-bromo-3-(((2-((tert-butoxycarbonyl)amino)phenyl)amino)methyl)-2-fluorobenzoate |

*$^1$H NMR (400.14 MHz, DMSO): δ 9.23 (s, 1H), 7.35-7.31 (m, 2H), 7.09-7.02 (m, 3H), 6.89 (d, J = 7.8 Hz, 1H), 4.92 (t, J = 5.3 Hz, 1H), 4.49-4.48 (m, 2H), 4.03 (q, J = 7.1 Hz, 1H), 2.79-2.72 (m, 4H), 2.33 (s, 3H), 1.46 (s, 9H).

Scheme 12

Preparation 99 tert-Butyl (3-(((2-fluoro-3-formyl-4-methylphenyl)(methyl)amino)methyl)phenyl)carbamate

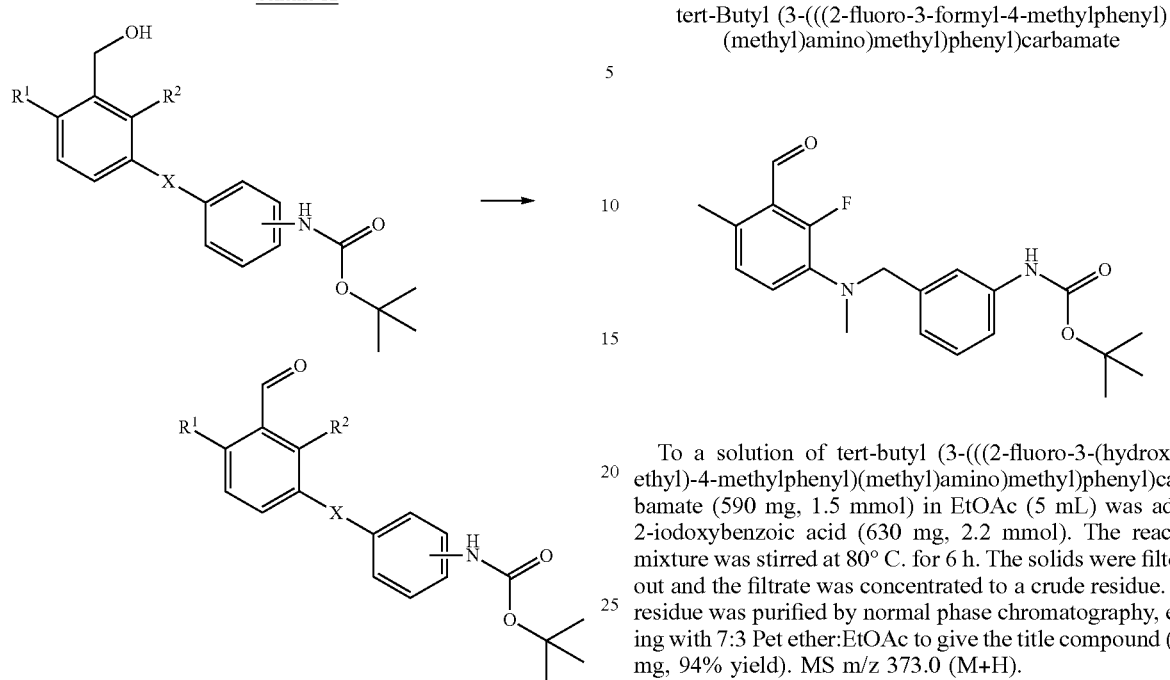

To a solution of tert-butyl (3-(((2-fluoro-3-(hydroxymethyl)-4-methylphenyl)(methyl)amino)methyl)phenyl)carbamate (590 mg, 1.5 mmol) in EtOAc (5 mL) was added 2-iodoxybenzoic acid (630 mg, 2.2 mmol). The reaction mixture was stirred at 80° C. for 6 h. The solids were filtered out and the filtrate was concentrated to a crude residue. The residue was purified by normal phase chromatography, eluting with 7:3 Pet ether:EtOAc to give the title compound (580 mg, 94% yield). MS m/z 373.0 (M+H).

The following compounds in Table 13 were prepared in a manner essentially analogous to the procedure described in Preparation 99.

TABLE 13

| | Preparations 100-104 | | |
|---|---|---|---|
| Prep. No. | Structure | ES/MS (m/z) (M + H) | Alcohol starting material |
| 100 | | No ion* | (6-bromo-3-(bromomethyl)-2-fluorophenyl)methanol |
| 101 | | 275.9 (M − Boc + H) | tert-butyl (2-((2-fluoro-3-(hydroxymethyl)-4-methylbenzyl)thio)phenyl)carbamate |
| 102 | | 424.9 | tert-butyl (3-((4-bromo-2-fluoro-3-(hydroxymethyl)benzyl)amino)phenyl)carbamate |

TABLE 13-continued

Preparations 100-104

| Prep. No. | Structure | ES/MS (m/z) (M + H) | Alcohol starting material |
|---|---|---|---|
| 103 | 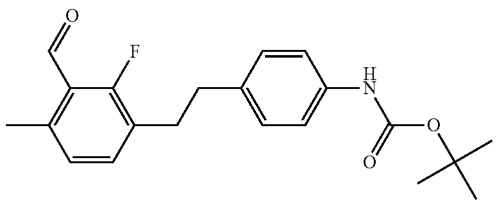 [SMILES: Cc1ccc(CCc2ccc(NC(=O)OC(C)(C)C)cc2)c(F)c1C=O] | No ion** | tert-butyl (4-(2-fluoro-3-(hydroxymethyl)-4-methylphenethyl)phenyl)carbamate |
| 104 | 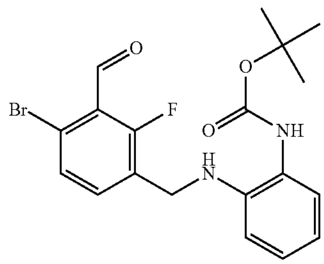 [SMILES: CC(C)(C)OC(=O)Nc1ccccc1NCc1ccc(Br)c(C=O)c1F] | 425.0 | tert-butyl (2-((4-bromo-2-fluoro-3-(hydroxymethyl)benzyl)amino)phenyl)carbamate |

*¹H NMR (400.15 MHz, DMSO): δ 10.31 (d, J = 0.8 Hz, 1H), 7.90-7.86 (m, 1H), 7.78 (dd, J = 0.8, 8.4 Hz, 1H), 4.84 (d, J = 1.0 Hz, 2H)
**¹H NMR (400.15 MHz, DMSO): δ 10.42 (s, 1H), 9.23 (s, 1H), 7.44-7.40 (m, 1H), 7.36-7.33 (m, 2H), 7.09-7.05 (m, 3H), 2.92-2.81 (m, 4H), 2.50 (s, 3H), 1.47 (s, 9H).

Preparation 105 tert-Butyl (4-(2-(2-fluoro-3-formyl-4-methylphenoxy)ethyl)phenyl)carbamate

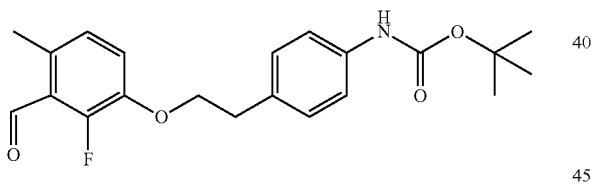

To a solution of 2-fluoro-3-hydroxy-6-methylbenzaldehyde (250 mg, 1.5 mmol) and 4-((tert-butoxycarbonyl)amino)phenethyl 4-methylbenzenesulfonate (760 mg, 1.9 mmol) in acetonitrile (10 mL) was added potassium carbonate (670 mg, 4.9 mmol). The suspension was stirred at 80° C. for 16 h. The reaction mixture was concentrated under reduced pressure to give a residue. The residue was diluted with water (40 mL), extracted with EtOAc (20 mL). The combined organic layers were washed with brine (20 mL), dried over anhydrous Na₂SO₄, filtered, and concentrated under reduced pressure to give a residue. The residue was purified by normal phase chromatography, eluting with 17:3 Pet ether:EtOAc to give the title compound (510 mg, 85% yield). ¹H NMR (400.15 MHz, CDCl₃): δ 10.47 (s, 1H), 7.24 (d, J=8.4 Hz, 2H), 7.15 (d, J=8.5 Hz, 2H), 6.96 (t, J=8.4 Hz, 1H), 6.82 (d, J=8.4 Hz, 1H), 6.37-6.35 (m, 1H), 4.12 (t, J=7.0 Hz, 2H), 3.01 (t, J=6.9 Hz, 2H), 2.45 (s, 3H), 1.45 (s, 8H).

Preparation 106

(6-Bromo-3-(bromomethyl)-2-fluorophenyl)methanol

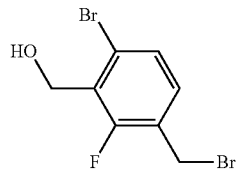 [SMILES: OCc1c(Br)ccc(CBr)c1F]

To a solution of 6-bromo-3-(bromomethyl)-2-fluorobenzoic acid (4.9 g, 11 mmol) in THF (100 mL) under a nitrogen atmosphere and cooled in an ice bath, borane-THF complex in THF (35 mL, 35 mmol, 1 mol/L) was added dropwise. The reaction mixture was allowed to warm to rt for overnight. The reaction was quenched by addition of MeOH (100 mL) and concentrated in vacuo. The resulting residue was partitioned between EtOAc (100 mL) and 1 M HCl (30 mL) and the aqueous layer was extracted once with EtOAc (100 mL). The combined organic extracts were dried with Na₂SO₄, filtered, and concentrated to give a crude residue. The residue was purified by normal phase chromatography, eluting with 7:3 Pet ether:EtOAc to give the title compound (2.9 g, 62% yield). ¹H NMR (400.15 MHz, DMSO): δ7.50-7.42 (m, 2H), 5.38-5.23 (m, 1H), 4.70 (d, J=0.5 Hz, 2H), 4.59 (d, J=1.5 Hz, 2H).

Scheme 13

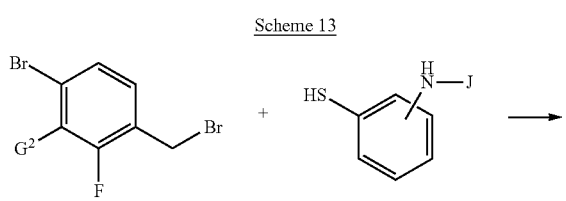

to give the crude residue. The residue was purified by normal phase chromatography, eluting with 3:1 Pet ether:EtOAc to give the title compound (780 mg, 89% yield). ¹H NMR (400.15 MHz, DMSO): δ 10.19 (s, 1H), 9.39 (s, 1H), 7.57-7.51 (m, 2H), 7.47 (s, 1H), 7.27 (d, J=8.6 Hz, 1H), 7.19 (t, J=7.9 Hz, 1H), 6.96 (d, J=7.8 Hz, 1H), 4.21 (s, 2H), 1.46 (s, 9H).

The following compound in Table 14 was prepared in a manner essentially analogous to the procedure described in Preparation 107.

TABLE 14

| Preparation 108 | | | |
| --- | --- | --- | --- |
| Prep. No. | Structure | ES/MS (m/z) (M + H) | Thiol starting material |
| 108 | 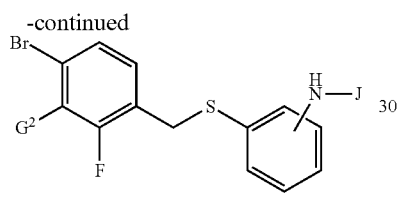 | 371.8 | 2-aminobenzenethiol |

-continued

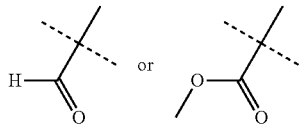

Wherein G² is

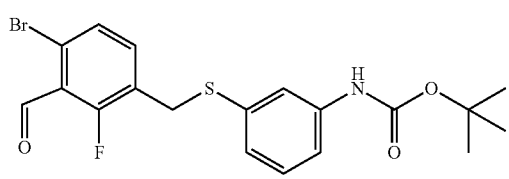

Wherein J is hydrogen or Boc.

Preparation 107 tert-Butyl (3-((4-bromo-2-fluoro-3-formylbenzyl)thio)phenyl)carbamate

To a mixture of 6-bromo-3-(bromomethyl)-2-fluorobenzaldehyde (620 mg, 1.9 mmol) and tert-butyl N-(3-sulfanylphenyl)carbamate (500 mg, 2.0 mmol) in DCM (10 mL) was added triethylamine (530 µL, 3.8 mmol) under N₂. The mixture was stirred at rt for 2 h. The reaction mixture was partitioned between DCM (30 mL) and water (30 mL). The combined organic extracts were concentrated under vacuum Preparation 109

Methyl 6-bromo-3-(((2-((tert-butoxycarbonyl)amino)phenyl)thio)methyl)-2-fluorobenzoate To a solution of methyl 3-(((2-aminophenyl)thio)methyl)-6-bromo-2-fluorobenzoate (1.3 g, 3.4 mmol) in tert-butanol (13 mL, 140 mmol) was added di-tert-butyl dicarbonate (3.5 mL, 15 mmol). The mixture was stirred at 50° C. overnight under N₂. The reaction was concentrated under vacuum to give the crude residue. The residue was purified by normal phase chromatography, eluting with 10:1 Pet ether:EtOAc to give the title compound (1.6 g, quantitative yield). MS m/z 371.8 (M-Boc+H).

Preparation 110

(3-Bromo-2-fluoro-4-methylphenyl)methanol

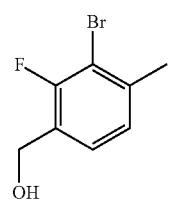

To a solution of 3-bromo-2-fluoro-4-methylbenzaldehyde (2 g, 6.6 mmol) in MeOH was added sodium borohydride (620 mg, 16 mmol) at 0° C. The mixture was stirred for 1 h. The mixture was slowly quenched with 1 M aq HCl (30 mL) under N₂, adjusting to pH 6. The reaction mixture was concentrated under vacuum to give crude residue. The residue was purified by normal phase chromatography, eluting with 1:2 Pet ether:EtOAc to give the title compound (820 mg, 51% yield).

Preparation 111 tert-Butyl (3-((3-bromo-2-fluoro-4-methylbenzyl)oxy)phenyl)carbamate

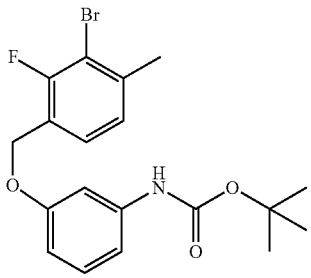 [SMILES: Cc1ccc(COc2cccc(NC(=O)OC(C)(C)C)c2)c(F)c1Br]

To a solution of (3-bromo-2-fluoro-4-methylphenyl)methanol (650 mg, 2.7 mmol), tert-butyl (3-hydroxyphenyl)carbamate (870 mg, 4.0 mmol), and tetrabutylphosphine (1.1 g, 5.4 mmol) in THF (10 mL, 120 mmol) was added N,N,N',N'-tetramethylazodicarboxamide (940 mg, 5.4 mmol). The reaction mixture was stirred at rt for 2 h under anhydrous N₂. The reaction mixture was partitioned between EtOAc (100 mL) and water (100 mL). The combined organic extracts were washed with brine (200 mL), dried with Na₂SO₄, filtered, and concentrated under vacuum to give crude residue. The residue was purified by normal phase chromatography, eluting with 9:1 Pet ether:EtOAc to give the title compound (1.2 g, 96% yield). MS m/z 355.8 (M-tBu+H).

Preparation 112 tert-Butyl (3-((2-fluoro-3-formyl-4-methylbenzyl)oxy)phenyl)carbamate

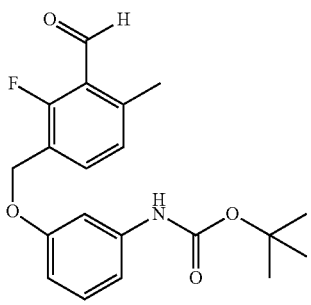 [SMILES: Cc1ccc(COc2cccc(NC(=O)OC(C)(C)C)c2)c(F)c1C=O]

To a solution of tert-butyl (3-((3-bromo-2-fluoro-4-methylbenzyl)oxy)phenyl)carbamate (0.82 g, 1.8 mmol) in THF (5 mL, 62 mmol) was added isopropylmagnesium chloride lithium chloride complex solution in THF (3.1 mL, 4.0 mmol, 1.3 mol/L) at 0° C. and stirred for 30 min. DMF (450 µL, 5.7 mmol) was added to the mixture at 0° C. The mixture was warmed to rt for 1.5 h and then quenched by addition of satd aq NH₄Cl (5 mL). The reaction mixture was partitioned between EtOAc (30 mL) and water (30 mL). The combined organic extracts were concentrated under vacuum to give the crude product. The residue was purified by normal phase chromatography, eluting with 95:5 Pet ether:EtOAc to give the title compound (220 mg, 25% yield). MS m/z 259.9 (M-Boc+H).

Preparation 113 tert-Butyl (2-((4-bromo-2-fluoro-3-formylbenzyl)oxy)phenyl)carbamate

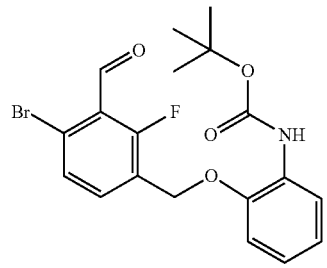 [SMILES: CC(C)(C)OC(=O)Nc1ccccc1OCc1ccc(Br)c(C=O)c1F]

Cesium carbonate (230 mg, 0.71 mmol) was added to a solution of tert-butyl (2-hydroxyphenyl)carbamate (100 mg, 0.47 mmol) and 6-bromo-3-(bromomethyl)-2-fluoro-benzaldehyde (160 mg, 0.51 mmol) in DMF (3 mL). The reaction mixture was stirred at rt for 1 h under N₂ and then quenched with the addition of water. The reaction mixture was partitioned between EtOAc (20 mL) and water (20 mL). The combined organic extracts were concentrated under vacuum to give the crude product. The residue was purified by normal phase chromatography, eluting with 4:1 Pet ether:EtOAc to give the title compound (210 mg, quantitative yield). ¹H NMR (400.21 MHz, DMSO): δ 10.24 (s, 1H), 8.08 (s, 1H), 7.82 (t, J=7.9 Hz, 1H), 7.69 (d, J=8.3 Hz, 1H), 7.63 (d, J=7.6 Hz, 1H), 7.10 (dd, J=1.0, 8.1 Hz, 1H), 7.06-7.02 (m, 1H), 6.95-6.91 (m, 1H), 5.21 (s, 2H), 1.44 (s, 9H).

Scheme 14

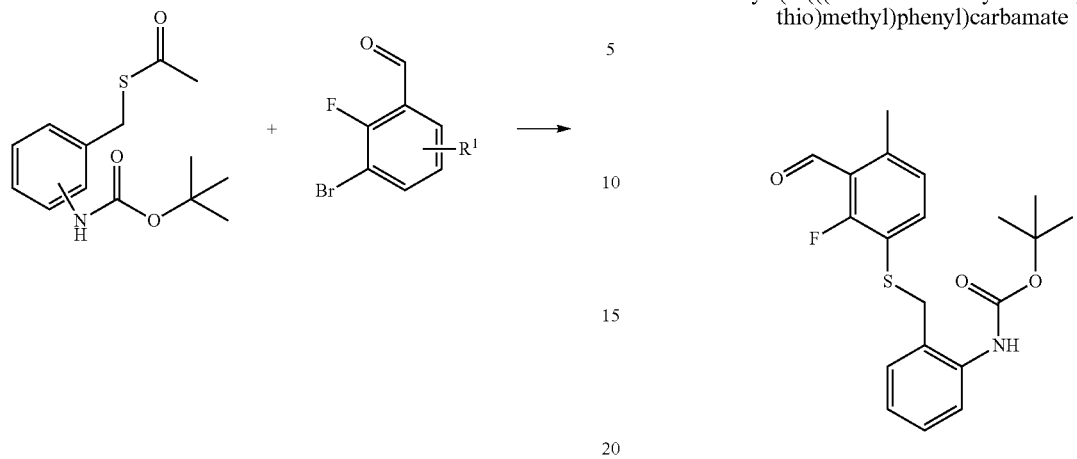

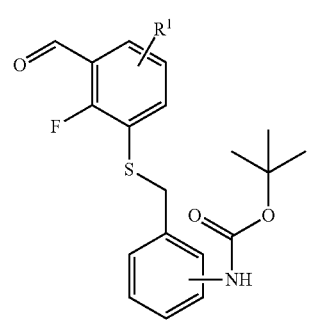

Preparation 114 tert-Butyl (2-(((2-fluoro-3-formyl-4-methylphenyl)thio)methyl)phenyl)carbamate

To a solution of S-(2-((tert-butoxycarbonyl)amino)benzyl) ethanethioate (670 mg, 2.2 mmol) in 1,4-dioxane (10 mL) and water (2 mL) was added 3-bromo-2-fluoro-6-methyl-benzaldehyde (550 mg, 1.8 mmol), 2-dicyclohexylphosphino-2',4',6'-triisopropylbiphenyl (220 mg, 0.44 mmol), potassium carbonate (610 mg, 4.4 mmol), and tris(dibenzylideneacetone)dipalladium(0) (210 mg, 0.22 mmol). The mixture was heated to 100° C. overnight. Upon completion, the reaction mixture was concentrated under reduced pressure. The residue was diluted with water (20 mL) and extracted with EtOAc (20 mL×2). The combined organic layers were washed with brine (40 mL), dried over Na$_2$SO$_4$, and concentrated in vacuo to give a residue. The residue was purified by normal phase chromatography, eluting with 95:5 Pet ether:EtOAc to give the title compound (670 mg, 54% yield). MS m/z 275.9 (M-Boc+H).

The following compounds in Table 15 were prepared in a manner essentially analogous to the procedure described in Preparation 114.

TABLE 15

Preparations 115-116

| Prep. No. | Structure | ES/MS (m/z) (M + H) | Thioate SM |
|---|---|---|---|
| 115 | ![structure] | 398.2 (M + Na) | S-(3-((tert-butoxycarbonyl)amino)benzyl) ethanethioate |
| 116 | ![structure] | 275.9 (M − Boc + H) | S-(3-((tert-butoxycarbonyl)amino)benzyl) ethanethioate |

Scheme 15

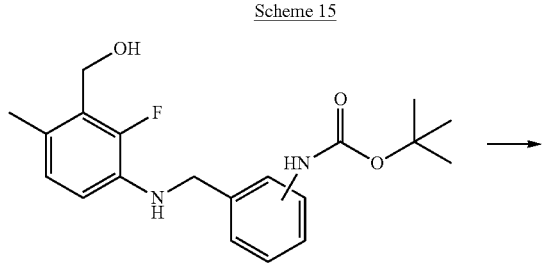

Preparation 117 tert-Butyl (2-(((2-fluoro-3-formyl-4-methylphenyl)amino)methyl)phenyl)carbamate

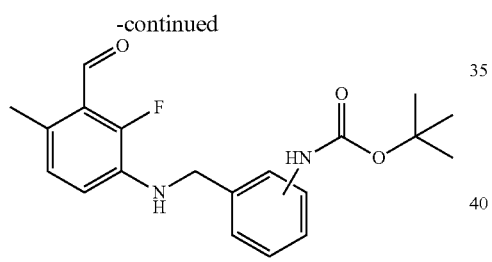

To a solution tert-butyl (2-(((2-fluoro-3-(hydroxymethyl)-4-methylphenyl)amino)methyl)phenyl)carbamate (950 mg, 2.4 mmol) in THF (20 mL) was added manganese dioxide (2.2 g, 25 mmol) at rt. The resulting mixture was stirred at 70° C. overnight. Additional manganese dioxide (2.2 g, 25 mmol) was added to the incomplete reaction and continued stirring at 70° C. for 4 h. Upon completion, the reaction mixture was filtered and washed with MeOH:DCM (1:1) through a pad of diatomaceous earth and the filtrate was concentrated under reduced pressure to afford the crude product. The residue was purified by normal phase chromatography, eluting with 9:1 Pet ether:EtOAc to give the title compound (220 mg, 20% yield). MS m/z 359.0 (M+H).

The following compound in Table 16 was prepared in a manner essentially analogous to the procedure described in Preparation 117.

TABLE 16

Preparation 118

| Prep. No. | Structure | ES/MS (m/z) (M + H) | Alcohol SM |
|---|---|---|---|
| 118 | 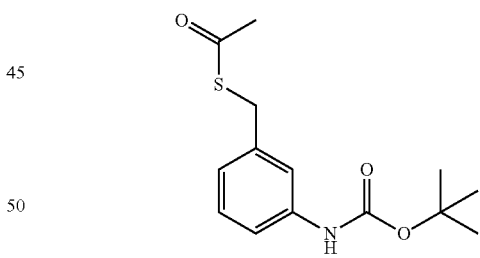 | 303.0 (M − tBu + H) | tert-butyl (3-(((2-fluoro-3-(hydroxymethyl)-4-methylphenyl)amino)methyl)phenyl)carbamate |

Preparation 119

S-(3-((tert-Butoxycarbonyl)amino)benzyl) ethanethioate

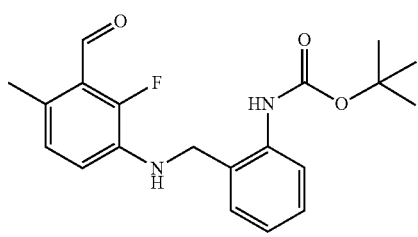 [SMILES: Cc1ccc(NCc2ccccc2NC(=O)OC(C)(C)C)c(F)c1C=O]

Dissolved tert-butyl (3-(bromomethyl)phenyl)carbamate (2.0 g, 6.7 mmol) and potassium thioacetate (1.6 g, 14 mmol) in DMF (9 mL, 120 mmol) and stirred at rt under N₂ for 2 h. The reaction was quenched by addition of a satd aq NH₄Cl (20 mL) and extracted with EtOAc (3×30 mL). The combined organic extracts were washed with brine (20 mL), dried with Na₂SO₄, filtered, and concentrated under vacuum to give the crude product. The residue was purified by normal phase chromatography, eluting with 17:3 Pet ether:EtOAc to give the title compound (1.8 g, 89% yield). MS m/z 225.9 (M-tBu+H).

Preparation 120

Methyl (E)-6-bromo-2-fluoro-3-(4-nitrostyryl)benzoate

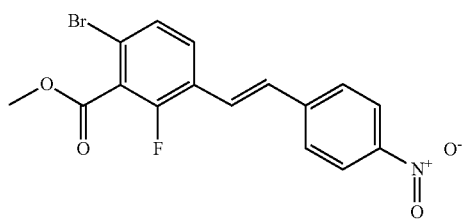

To a solution of diethyl (4-nitrobenzyl)phosphonate (1.7 g, 6.1 mmol) and 15-crown-5 (1.3 g, 5.7 mmol) in DMF (30 mL) was added sodium hydride in oil (340 mg, 8.5 mmol, 60 mass %). After stirring at 0° C. for 30 min, methyl 6-bromo-2-fluoro-3-formylbenzoate (1.5 g, 5.7 mmol) was added under $N_2$. After 1.5 h, the reaction was quenched by addition of satd aq $NH_4Cl$ (40 mL) to precipitate a yellow solid. The solid was collected by suction filtration, washed with water, and dried under vacuum to give the title compound (2.2 g, 89% yield). MS m/z 379.9, 381.9 (M+H).

Preparation 121

Methyl 3-(4-((tert-butoxycarbonyl)amino)phenethyl)-2-fluoro-6-methylbenzoate

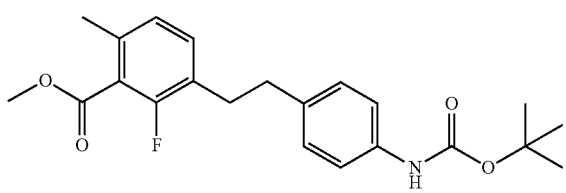 [SMILES: COC(=O)c1c(C)ccc(CCc2ccc(NC(=O)OC(C)(C)C)cc2)c1F]

To a solution of methyl (E)-2-fluoro-6-methyl-3-(4-nitrostyryl)benzoate (710 mg, 2.2 mmol) in MeOH (15 mL) was added palladium (650 mg, 0.31 mmol) and di-tert-butyl dicarbonate (0.57 mL, 2.5 mmol). The mixture was stirred at rt for 2 h under $H_2$ (15 psi). The reaction mixture was filtered through a pad of diatomaceous earth and the filtrate was concentrated under reduced pressure to afford the crude product. The residue was purified by normal phase chromatography, eluting with 3:2 Pet ether:EtOAc to give the title compound (620 mg, 69% yield). $^1$H NMR (400.21 MHz, DMSO): δ 9.24 (s, 1H), 7.34 (d, J=8.3 Hz, 2H), 7.26 (t, J=7.9 Hz, 1H), 7.05 (dd, J=8.2, 14.8 Hz, 3H), 3.87 (s, 3H), 2.86-2.68 (m, 4H), 2.26 (s, 3H), 1.47 (s, 10H).

Preparation 122 tert-Butyl (3-((4-bromo-3-(1,3-dioxolan-2-yl)-2-fluorophenoxy)methyl)phenyl)carbamate

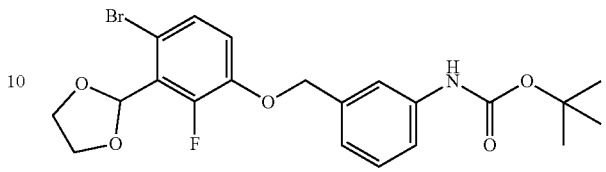

With a Dean-Stark trap attached, a solution of tert-butyl (3-((4-bromo-2-fluoro-3-formylphenoxy)methyl)phenyl)carbamate (1.0 g, 2.5 mmol), ethylene glycol (0.55 mL, 9.8 mmol), and p-toluenesulfonic acid monohydrate (47 mg, 0.25 mmol) in toluene (16 mL, 150 mmol) was refluxed at 135° C. for 1 h. The reaction solution was cooled to rt and diluted with water (15 mL) and EtOAc (25 mL). The phases were separated, and the aqueous was extracted with EtOAc. The combined organic layers were dried with $Na_2SO_4$, filtered, and evaporated to give a crude residue. The residue was purified by normal phase chromatography, eluting with 24:1 DCM:MeOH to give the title compound (1.2 g, 44% yield). MS m/z 486.8 (M+$NH_4$).

Alternative Preparation 122 tert-Butyl (3-((4-bromo-3-(1,3-dioxolan-2-yl)-2-fluorophenoxy)methyl)phenyl)carbamate With a Dean-Stark trap attached, a solution of 6-bromo-2-fluoro-3-hydroxybenzaldehyde (1.04 g, 4.75 mmol), ethylene glycol (1.1 mL, 20 mmol), and p-toluenesulfonic acid monohydrate (88 mg, 0.46 mmol) in toluene (32 mL) was refluxed at 135° C. for 1 h. The reaction solution was cooled to rt and washed with water (15 mL). The phases were separated. The organic layer was dried with $Na_2SO_4$, filtered, and evaporated to give a crude residue. The residue was purified by normal phase chromatography, eluting with 20:1 DCM:MeOH to give 4-bromo-3-(1,3-dioxolan-2-yl)-2-fluoro-phenol (1.06 g, 4.03 mmol). This material was dissolved in DMF (8.0 mL) and potassium carbonate (1.40 g, 10.1 mmol) was added. This mixture was stirred at rt for 5 min. tert-Butyl 3-(bromomethyl)phenylcarbamate (1.21 g, 4.23 mmol) was then added and the mixture stirred for 75 min. The mixture was then diluted with water (40 mL) and extracted with EtOAc (40 mL). The phases were separated. The organic layer was dried with $Na_2SO_4$, filtered, and evaporated to give a crude residue. The residue was purified by normal phase chromatography, eluting with 3:1 EtOAc: hexanes to give tert-butyl (3-((4-bromo-3-(1,3-dioxolan-2-yl)-2-fluorophenoxy)methyl)phenyl)carbamate (1.72 g, 3.66 mmol, 77% yield). MS m/z 485.0, 487.2 (M+$NH_4$).

Scheme 16

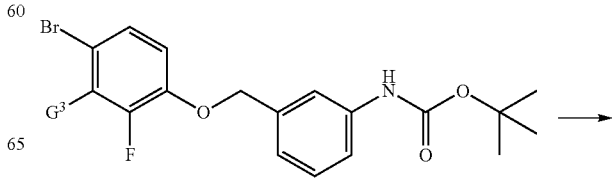

-continued

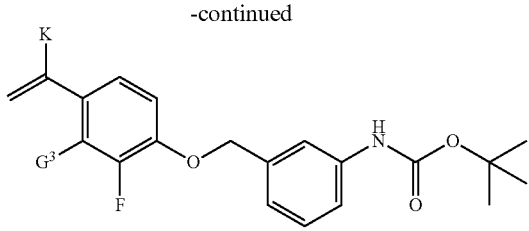

Wherein G³ is

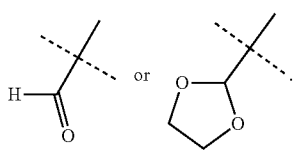

Wherein K is hydrogen or methyl.

microwave vial that was purged with N₂. THF (9 mL) and water (1 mL, 56 mmol) were added. The mixture was degassed by bubbling sub-surface N₂ for 5 minutes, palladium(II) acetate (10 mg, 0.04 mmol) was added, and the reaction was heated to 100° C. overnight. The reaction was cooled to rt for 3 days. EtOAc and water were added, the phases were separated, and the aqueous layer was extracted twice with EtOAc. The combined organic layers were dried over Na₂SO₄, filtered, and concentrated to a crude residue. The residue was purified by normal phase chromatography, eluting with 3:2 hexanes:EtOAc to give the title compound (320 mg, 16% yield). MS m/z 369.6 (M−H).

The following compound in Table 17 was prepared in a manner essentially analogous to the procedure described in Preparation 123.

TABLE 17

| Preparation 124 | | | |
|---|---|---|---|
| Prep. No. | Structure | ES/MS (m/z) (M + H) | Borate SM |
| 124 | 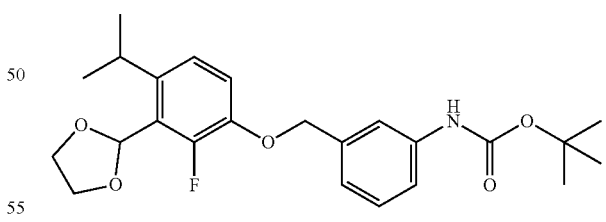 | 428.2 (M − H) | trifluoro(prop-1-en-2-yl)borate potassium(I) |

Preparation 123 tert-Butyl (3-((2-fluoro-3-formyl-4-vinylphenoxy)methyl)phenyl)carbamate

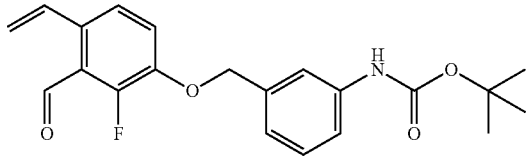 [SMILES: C=Cc1ccc(OCc2cccc(NC(=O)OC(C)(C)C)c2)c(F)c1C=O]

tert-Butyl (3-((4-bromo-3-(1,3-dioxolan-2-yl)-2-fluoro-phenoxy)methyl)phenyl)carbamate (400 mg, 0.85 mmol), potassium vinyltrifluoroborate (0.14 g, 1.0 mmol), and cesium carbonate (0.84 g, 2.6 mmol) were placed in a 25-mL Preparation 125 tert-Butyl N-[3-[[3-(1,3-dioxolan-2-yl)-2-fluoro-4-isopropyl-phenoxy]methyl]phenyl]carbamate Sulfided 5 wt % platinum on carbon (0.057 g, 0.29 mmol) was added to a 70-mL Parr shaker bottle and degassed with N₂. Added 5 mL EtOAc, then added tert-butyl (3-((3-(1,3-dioxolan-2-yl)-2-fluoro-4-(prop-1-en-2-yl)phenoxy)methyl)phenyl)carbamate (0.231 g, 0.538 mmol) in 6 mL EtOAc to the bottle. The bottle was sealed, purged with N₂, purged with H₂, and pressurized to 60 psi H₂ for 5 h at rt. The reaction mixture was filtered and concentrated to give the title compound (255 mg, quant yield). MS m/z 430.4 (M−H).

Preparation 126 tert-Butyl (3-((4-cyano-3-(1,3-dioxolan-2-yl)-2-fluorophenoxy)methyl)phenyl)carbamate

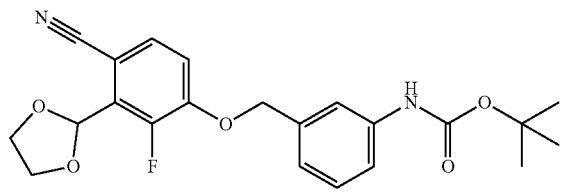 [SMILES: CC(C)(C)OC(=O)Nc1cccc(COc2ccc(C#N)c(C3OCCO3)c2F)c1]

In a microwave vial, a mixture of tert-butyl (3-((4-bromo-3-(1,3-dioxolan-2-yl)-2-fluorophenoxy)methyl)phenyl)carbamate (240 mg, 0.50 mmol), zinc cyanide (130 mg, 1.1 mmol), and zinc chloride in THF (1.0 mL, 0.50 mmol, 0.500 mol/L) in DMF (2.5 mL, 32 mmol) was bubbled with $N_2$. Tetrakis(triphenylphosphine)palladium(0) (31 mg, 0.03 mmol) was added. The reaction mixture was bubbled with $N_2$, capped, and microwaved at 110° C. for 1 h. Additional zinc cyanide (120 mg, 1.0 mmol) and tetrakis(triphenylphosphine)palladium(0) (27 mg, 0.02 mmol) were added. The reaction mixture was bubbled with $N_2$, capped, and microwaved at 120° C. for 30 min. The reaction solution was washed with water (15 mL). The organic layer was dried with $Na_2SO_4$, filtered through paper, and rotary evaporated to give crude residue. The residue was purified by normal phase chromatography, eluting with 7:3 hexanes:EtOAc to give the title compound (90 mg, 43% yield). MS m/z 412.6 (M−H).

In Scheme 17, the compound of structure 1, wherein R is H, is reacted with a compound of structure 2, wherein Pg is a suitable nitrogen protecting group, such as a tert-butyloxy carbonyl, and wherein G is:

under conditions well known to one of ordinary skill in the art to provide the compound of Formula I wherein R is hydrogen.

More specifically, as shown in Scheme 17A below, the compound of structure 1a, wherein R is H, is reacted with the compound of structure 2, wherein Pg and G are defined as above, under conditions well known to one of ordinary skill in the art to provide the compounds of Formula Ib and Formula Ic.

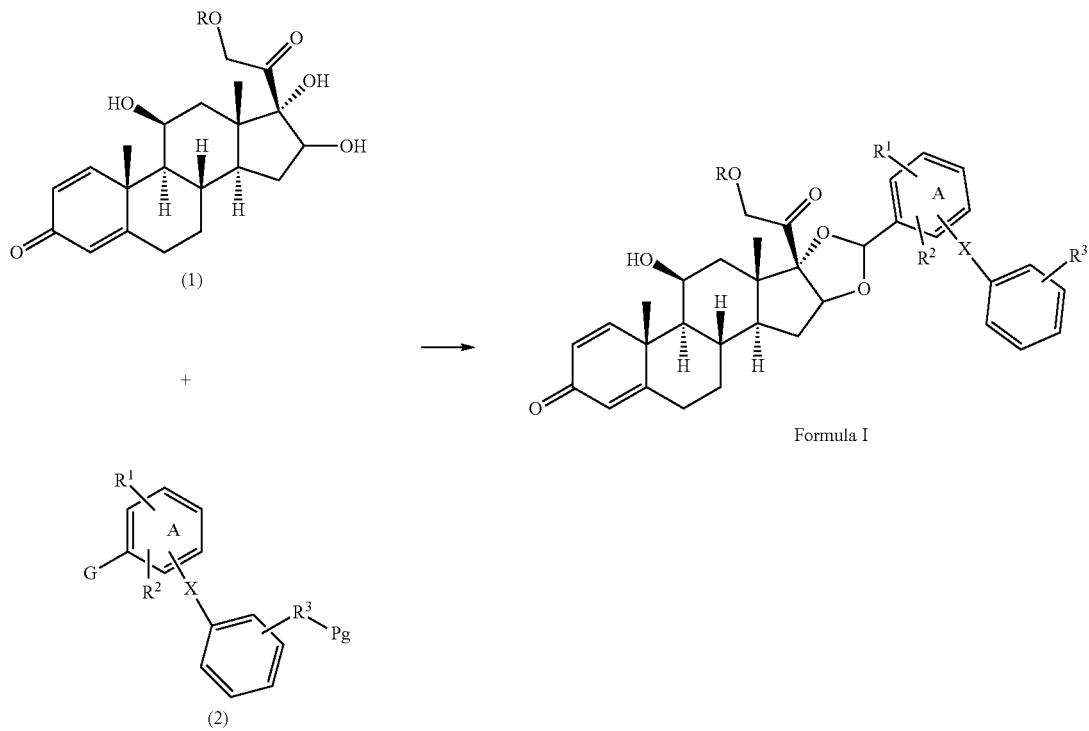

Scheme 17

Scheme 17A

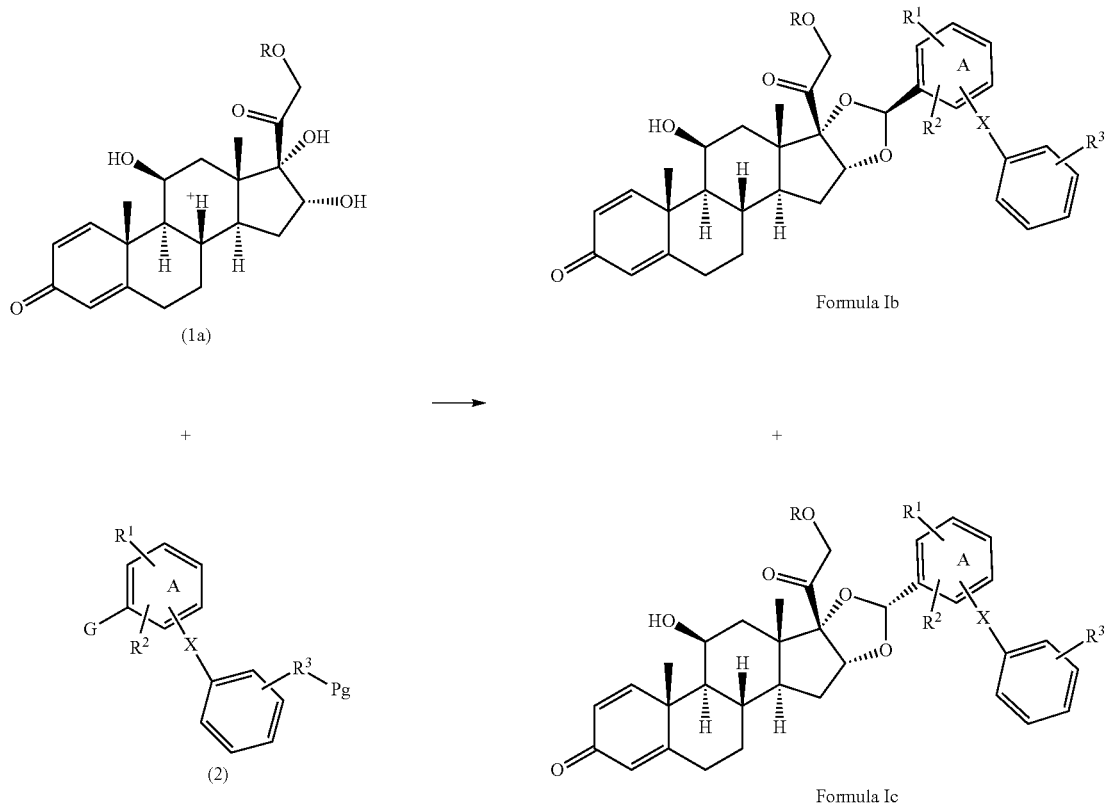

For example, about 1 equivalent of the compound of structure 1a, wherein R is H, and about 1 equivalent of a compound of structure 2, wherein Pg and G are as defined in Scheme 17, are suspended in a suitable organic solvent, such as acetonitrile. The suspension is cooled to about −10° C. to about −25° C. and then treated with about 5 equivalents of a suitable acid, such as perchloric acid (70% in water) or trifluoroacetic acid. The reaction mixture is then warmed to room temperature and allowed to stir for about 1 to 8 hours. Additional organic solvents may be added, such as acetonitrile and dimethylformamide, and the mixture is allowed to stir for about 2 additional hours. The reaction is then quenched using standard conditions, such as with saturated aqueous sodium bicarbonate and the products are isolated using standard techniques well known in the art, such as extraction with suitable organic solvents, such as methylene chloride:isopranol, drying the organic extracts over magnesium sulfate, filtering, and concentration under vacuum to provide the crude product mixture. This crude mixture can be purified and the products of Formula Ib and Formula Ic separated using techniquest well know in the art, such as chromatography, including for example normal phase chromatography with a suitable eluent, such as MeOH in DCM, and reverse phase chromatography with a suitable eluent, such as 2:1 10 mM ammonium bicarbonate water +5% methanol:acetonitrile.

EXAMPLE 1

(6aR,6bS,7S,8aS,8bS,10R,11aR,12aS,12bS)-10-(3-((3-Aminobenzyl)oxy)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one

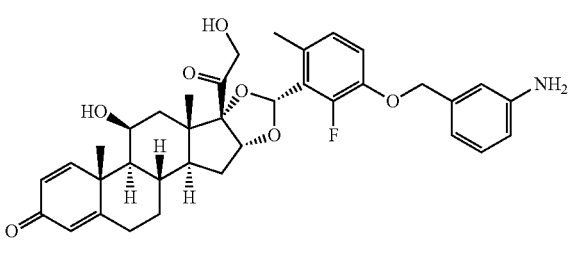

Perchloric acid (70% in water, 4.8 mL) was added to a suspension of (8S,9S,10R,11S,13S,14S,16S,17S)-11,16,17-trihydroxy-17-(2-hydroxyacetyl)-10,13-dimethyl-7,8,9,11,12,14,15,16-octahydro-6H-cyclopenta[a]phenanthren-3-one (4.4 g, 12 mmol, also referred to as "16alpha-hydroxyprednisolone") and tert-butyl N-[3-[(2-fluoro-3-formyl-4-methyl-phenoxy)methyl]phenyl]carbamate (4.0 g, 11 mmol, preparation 4) in acetonitrile (110 mL) at −10° C. and was warmed to rt. After 1 h, DMF (10 mL) was added to the suspension at rt. After 18 h, the reaction was quenched with saturated aqueous sodium bicarbonate and extracted with 9:1 methylene chloride:isopropanol. The organic layers were combined; dried over magnesium sulfate; filtered, and concentrated under reduced pressure to give a residue. The residue was purified by reverse phase chromatography, eluting with 1:1 10 mM ammonium bicarbonate water+5% methanol:acetonitrile to give the title compound, peak 1 (1.72 g, 25% yield). ES/MS m/z 618.6 (M+H). $^1$H NMR (400.13 MHz, d$_6$-DMSO) δ 0.93-0.87 (m, 6H), 1.40 (s, 3H), 1.71-1.60 (m, 1H), 1.89-1.76 (m, 4H), 2.18-2.12 (m, 2H), 2.29 (s, 4H), 4.23-4.17 (m, 1H), 4.32-4.30 (m, 1H), 4.50-4.43 (m, 1H), 4.81 (d, J=3.2 Hz, 1H), 4.98-4.95 (m, 3H), 5.16-5.10 (m, 3H), 5.61 (s, 1H), 5.95 (s, 1H), 6.18-6.15 (m, 1H), 6.53-6.48 (m, 2H), 6.58 (s, 1H), 6.90-6.86 (m, 1H), 6.99 (t, J=7.7 Hz, 1H), 7.12 (t, J=8.5 Hz, 1H), 7.33-7.30 (m, 1H).

EXAMPLE 2

(6aR,6bS,7S,8aS,8bS,10S,11aR,12aS,12bS)-10-(3-((3-Aminobenzyl)oxy)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one

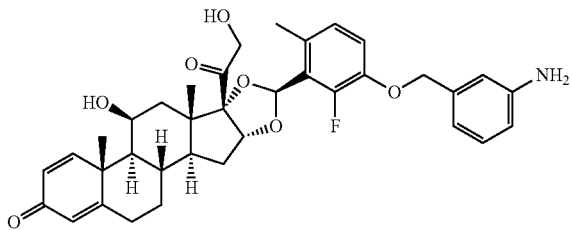

From Example 1, the residue was purified by reverse phase chromatography, eluting with 1:1 10 mM ammonium bicarbonate water+5% methanol:acetonitrile to give the title compound, peak 2 (1.24 g, 18% yield). ES/MS m/z 618.6 (M+H). $^1$H NMR (400.13 MHz, d$_6$-DMSO) δ $^1$H NMR (400.13 MHz, DMSO): 0.88 (s, 3H), 1.24-1.12 (m, 2H), 1.40 (s, 3H), 1.69-1.56 (m, 1H), 1.91-1.76 (m, 4H), 2.08-2.01 (m, 2H), 2.22 (s, 3H), 2.39-2.29 (m, 1H), 3.18 (d, J=5.2 Hz, 1H), 4.12-4.00 (m, 1H), 4.37-4.30 (m, 2H), 4.79 (d, J=3.1 Hz, 1H), 5.00-4.93 (m, 2H), 5.10-5.06 (m, 3H), 5.31 (d, J=6.7 Hz, 1H), 5.95 (s, 1H), 6.18 (dd, J=1.8, 10.1 Hz, 1H), 6.34 (s, 1H), 6.53-6.48 (m, 2H), 6.58 (s, 1H), 6.87 (d, J=8.5 Hz, 1H), 6.99 (t, J=7.7 Hz, 1H), 7.09 (t, J=8.5 Hz, 1H), 7.33 (d, J=10.1 Hz, 1H).

EXAMPLE 3

(6aR,6bS,7S,8aS,8bS,10S,11aR,12aS,12bS)-10-(3-((3-Aminobenzyl)oxy)-2-fluoro-6-methylphenyl)-7-hydroxy-6a,8a-dimethyl-8b-(2-(((2R,3R,4S,5R,6R)-3,4,5-trihydroxy-6-(hydroxymethyl)tetrahydro-2H-pyran-2-yl)oxy)acetyl)-1,2,6a,6b,7,8,8a,8b,11a,12,12a,12b-dodecahydro-4H-naphtho[2',1':4,5]indeno[1,2-d][1,3]dioxol-4-one (2R,3 S,4S,5R,6R)-2-(Acetoxymethyl)-6-(2-((6aR,6bS,7S,8aS,8bS,10S,11aR,12aS,12bS)-10-(3-((3-aminobenzyl)oxy)-2-fluoro-6-methylphenyl)-7-hydroxy-6a,8a-dimethyl-4-oxo-1,2,4,6a,6b,7,8,8a,11a,12,12a,12b-dodecahydro-8bH-naphtho[2',1':4,5]indeno[1,2-d][1,3]dioxol-8b-yl)-2-oxoethoxy)tetrahydro-2H-pyran-3,4,5-triyl triacetate (40 mg, 0.04 mmol, Preparation 5) was added to methanol (2 mL) and potassium carbonate (20 mg, 0.20 mmol). After 1 h, the mixture was loaded onto a diatomaceous earth and was purified by reverse phase chromatography, eluting with 1:2 10 mM ammonium bicarbonate water+5% methanol:acetonitrile to give the title compound (19 mg, 57% yield). ES/MS m/z 780.4 (M+H). $^1$H NMR (500.11 MHz, d$_6$-DMSO) δ 0.90 (s, 3H), 1.28-1.27 (m, 2H), 1.41 (s, 3H), 1.72-1.69 (m, 1H), 1.92-1.88 (m, 4H), 2.11-2.10 (m, 2H), 2.22 (s, 3H), 2.40-2.35 (m, 1H), 3.50-3.46 (m, 1H), 3.57-3.53 (m, 1H), 3.64-3.61 (m, 1H), 4.17-4.15 (m, 1H), 4.34-4.32 (m, 1H), 4.43-4.39 (m, 2H), 4.57-4.52 (m, 1H), 4.64-4.62 (m, 1H), 4.75-4.72 (m, 2H), 5.00-4.93 (m, 3H), 5.12-5.08 (m, 2H), 5.31-5.29 (m, 1H), 5.95 (d, J=0.4 Hz, 1H), 6.20-6.17 (m, 1H), 6.34 (s, 1H), 6.54-6.49 (m, 2H), 6.59 (s, 1H), 6.88 (d, J=8.5 Hz, 1H), 7.00 (t, J=7.7 Hz, 1H), 7.12-7.08 (m, 1H), 7.35-7.33 (m, 1H).

EXAMPLE 4

(6aR,6bS,7S,8aS,8bS,10R,11aR,12aS,12bS)-10-(3-((3-Aminobenzyl)oxy)-2-fluoro-6-methoxyphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one

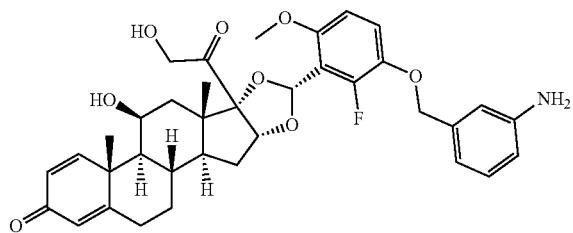

To a suspension of tert-butyl (3-((2-fluoro-3-formyl-4-methoxyphenoxy)methyl)phenyl)carbamate (2.6 g, 6.9 mmol, preparation 8) and 16alpha-hydroxyprednisolone (2.5 g, 6.6 mmol) in acetonitrile (100 mL) at −20° C. was added perchloric acid (70% in water, 3.3 mL, 5 equiv) dropwise. The mixture was stirred at −20° C. for 7 h. The solution was transferred to a separatory funnel. The solution was added dropwise to an aqueous solution of sodium hydroxide (7.5 mL 5N aq NaOH in 1 L water). After the addition was completed, the pH was measured at 5 and the pH was adjusted to 8 with 5N aq NaOH. The suspension was stirred for 10 minutes. The solid was collected by vacuum filtration and the solid was washed with water. The solid was dried on the filter overnight. The solid was purified by reverse phase chromatography, eluting with 1:1 10 mM ammonium bicarbonate water+5% methanol:acetonitrile to give the title compound, peak 1 (804 mg, 18% yield). MS m/z 634.2 (M+H). $^1$H NMR (399.8 MHz, d$_6$-DMSO) δ 7.33 (d, J=10.1 Hz, 1H), 7.17 (t, J=9.2 Hz, 1H), 6.98 (t, J=7.8 Hz, 1H), 6.76 (dd, J=1.0, 9.2 Hz, 1H), 6.56 (d, J=1.6 Hz, 1H), 6.52-6.48 (m, 2H), 6.17 (dd, J=1.9, 10.1 Hz, 1H), 5.96 (s, 1H), 5.71 (s, 1H), 5.17 (t, J=6.0 Hz, 1H), 5.10 (s, 2H), 4.94-4.90 (m, 3H), 4.79 (d, J=3.1 Hz, 1H), 4.44-4.38 (m, 1H), 4.33-4.31 (m, 1H), 4.22-4.15 (m, 1H), 3.70 (s, 3H), 2.37-2.33 (m, 1H), 2.14-2.04 (m, 2H), 1.96-1.88 (m, 1H), 1.82-1.70 (m, 3H), 1.64-1.56 (m, 1H), 1.41 (s, 3H), 0.86 (s, 5H).

EXAMPLE 5

(6aR,6bS,7S,8aS,8bS,10S,11aR,12aS,12bS)-10-(3-((3-Aminobenzyl)oxy)-2-fluoro-6-methoxyphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one

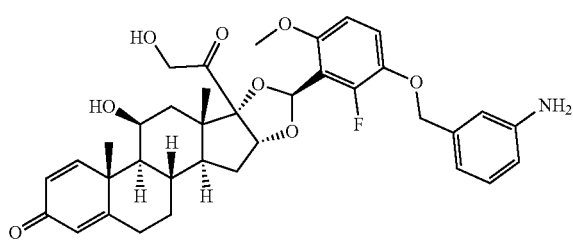

From Example 4, the residue was purified by reverse phase chromatography, eluting with 1:1 10 mM ammonium bicarbonate water+5% methanol:acetonitrile to give the title compound peak 2 (1.19 g, 27% yield). MS m/z 634.2 (M+H). $^1$H NMR (399.8 MHz, d$_6$-DMSO) δ 7.32 (d, J=10.0 Hz, 1H), 7.17-7.12 (m, 1H), 6.99 (t, J=7.7 Hz, 1H), 6.72 (d, J=8.8 Hz, 1H), 6.58 (s, 1H), 6.53-6.46 (m, 3H), 6.18 (dd, J=1.7, 10.1 Hz, 1H), 5.95 (s, 1H), 5.25 (d, J=6.5 Hz, 1H), 5.10 (s, 2H), 5.00-4.90 (m, 3H), 4.78 (d, J=3.1 Hz, 1H), 4.37-4.31 (m, 2H), 4.02-3.96 (m, 1H), 3.63 (s, 3H), 2.34-2.31 (m, 1H), 2.11-2.02 (m, 2H), 1.88-1.76 (m, 4H), 1.60-1.54 (m, 1H), 1.40 (s, 3H), 1.23-1.18 (m, 2H), 0.87 (s, 3H).

Alternative Preparation of Example 5

All solid handling steps were handled in a disposable glove bag including charging the flask with 16alpha-hydroxyprednisolone, solid filtration steps and solid transfer steps.

To a suspension of tert-butyl (3-((2-fluoro-3-formyl-4-methoxyphenoxy)methyl)phenyl)carbamate (25 g, 67 mmol, preparation 8) and 16alpha-hydroxyprednisolone (25 g, 65 mmol) in ACN (1000 mL) at −25° C. in a 2-L round bottom flask was added perchloric acid in water (31 mL, 330 mmol, 10.6 mol/L) dropwise. The mixture was stirred at −20° C. while monitoring the reaction by LCMS. Internal temperature monitoring indicated a small exotherm upon addition of perchloric acid. The internal temperature was kept below −19° C. with dry ice addition. The mixture was kept below −19° C. for 2 h and then was allowed to warm to −10° C. The mixture split in two and added dropwise to two separate beakers (Beaker 1 and Beaker 2) containing 76 mL of 5 M aq NaOH in 2 L of water, each. A solid formed upon addition and complete quench of perchloric acid was tested (pH 10). The sticky solid from each addition was transferred and combined to a third beaker (Beaker 3) containing 10% MeOH in DCM. The mixture was stirred until the sticky solid completely dissolved. The remaining solutions (Beaker 1 and Beaker 2) were then filtered through paper to collect residual solids. The isolated solids were rinsed with water and transferred to Beaker 3. Beaker 3 was stirred until all solids were dissolved. The solution was dried for 2 h with Na$_2$SO$_4$, filtered and evaporated to give a tan foam. The filtrates from the solid collection were extracted with three portions 10% IPA in DCM. The combined organic extracts were dried over Na$_2$SO$_4$ with stirring overnight, then filtered and evaporated to give additional crude residue. The crude products were dissolved in 150 mL 1% MeOH in DCM and purified by normal phase chromatography using 0-5% MeOH in DCM to give a solid. It was diluted with 600 mL EtOH and spun on the rotary evaporator at 45° C. for 5 minutes. The heat bath was turned up to 60° C. When the heat bath reached 60° C. it was turned off and the flask spun until the bath reached rt. The flask was taken off the rotary evaporator, capped and allowed to stand overnight at room temperature.

The solid was collected by vacuum filtration in a glove bag. The solids were rinsed with EtOH and dried on the filter for 5 h. The solid redissolved in 20% EtOH in DCM (1.5 L). Additional DCM was added to achieve a near clear solution (some haze persisted). Solvent exchange was achieved by rotary evaporation at 450 mbar and 45° C. to remove DCM. Once distillation had stopped, the pressure was decreased to 100 mbar to bring off EtOH to approximately 600 mL. The mixture was removed from the rotary evaporator and allowed to stand for 5 h at rt. The solid was collected by vacuum filtration and the solids washed twice with additional EtOH. The filter cake was dried in a vacuum oven at rt for 48 h to give the title compound (42 g, 38% yield). MS m/z 634.6 (M+H).

Structural Assignment by NMR

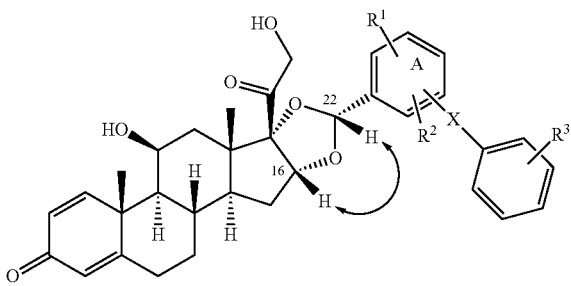

Two dimensional through-space ROE NMR analysis of acetal isomers consistently gave a cross peak for H22 (acetal) and H16 in the R configuration. Alternatively, H22 in the S configuration consistently gave about 1 ppm larger shift. All other compounds were assigned essentially by the same method.

The following compounds in Table 18a were prepared in a manner essentially analogous to the procedures described in Examples 1 to 4 utilizing the corresponding starting material of structure 1a and starting material of structure 2 as prepared in the corresponding preparations and tables 2-17 described above or prepared using standard procedures well known to one of ordinary skill in the art. Purification of final products was performed essentially by the following methods:

A. C18 column using eluent 10 mM $NH_4HCO_3$ in water+ 5% MeOH:ACN
B. C18 column using eluent 0.1% FA in water:ACN
C. SFC Chiralpak AY using eluent EtOH+0.05% DEA: $CO_2$
D. Chiralpak IC using eluent MeOH+0.2% IPAm
E. SFC Lux Amylose-2 using eluent IPA+0.5% DMEA: $CO_2$
F. SFC Chiralpak AD-H using eluent IPA+0.5% DMEA: $CO_2$
G. Chiralpak IC using eluent EtOH+0.1% $NH_3H_2O$: heptane
H. SFC Chiralpack AD using eluent IPA+0.1% $NH_3H_2O$: $CO_2$
I. Chiralcel IH using eluent EtOH+ACN (0.1% DEA): heptane
J. SFC Chiralpak AD using eluent EtOH+0.5% DEA:$CO_2$
K. Chiralpak IE using eluent EtOH+0.1% $NH_3H_2O$:ACN
L. Chiralpak AD-H using eluent EtOH:ACN+0.2% IPAm
M. Chiralpak AD-H using eluent EtOH:ACN
N. SFC Chiralpak IC using eluent EtOH+0.05% DMEA: $CO_2$
O. SFC Chiralcel OJ-H using eluent MeOH+0.5% DMEA:$CO_2$ TABLE 18a Examples 6-158 (structures)

| Ex No. | Structure | ES/MS (m/z) (M + H) | Purification method* |
|---|---|---|---|
| 6 | 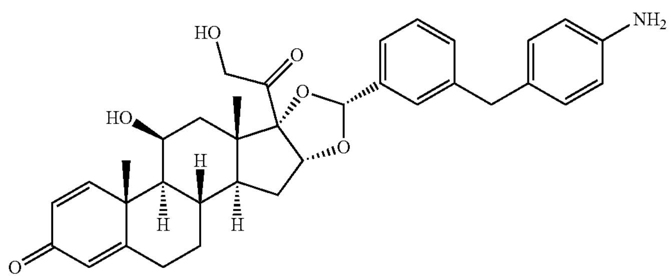 | 570.4 | A |
| 7 | 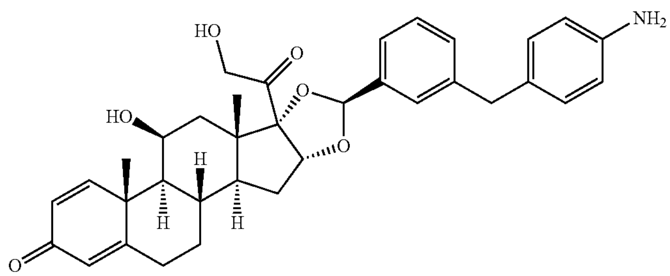 | 570.4 | A |

TABLE 18a-continued
Examples 6-158 (structures)
| Ex No. | Structure | ES/MS (m/z) (M + H) | Purification method* |
|---|---|---|---|
| 8 | 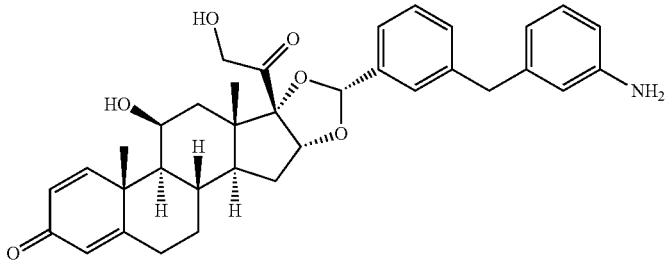 | 570.4 | A |
| 9 | 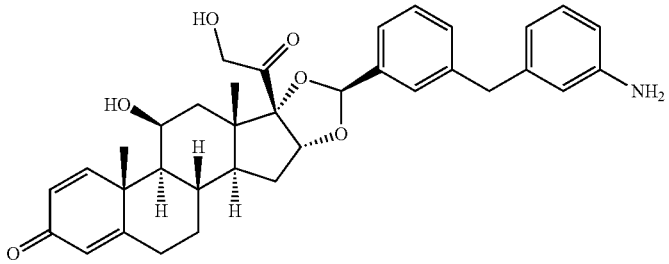 | 570.4 | A |
| 10 | 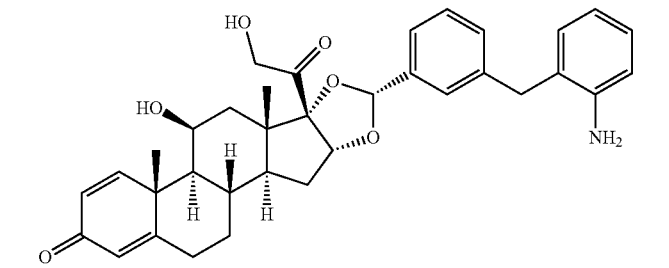 | 571.4 | B |
| 11 | 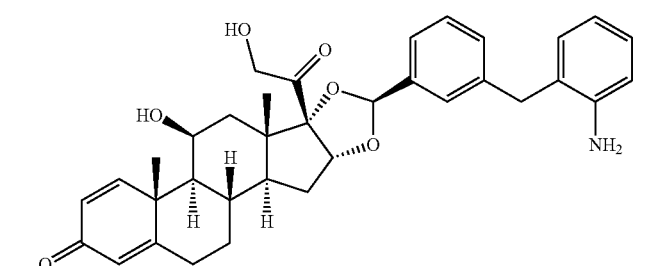 | 570.4 | B |
| 12 | 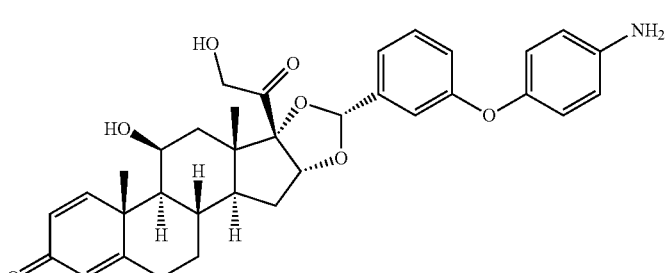 | 572.2 | A |

TABLE 18a-continued

Examples 6-158 (structures)

| Ex No. | Structure | ES/MS (m/z) (M + H) | Purification method* |
|---|---|---|---|
| 13 | 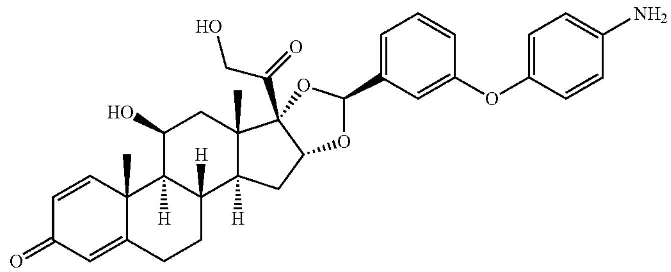 | 572.2 | A |
| 14 | 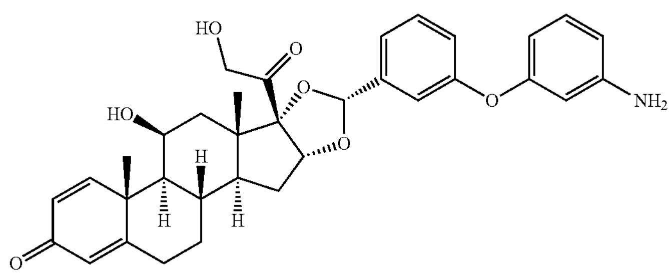 | 572.2 | A |
| 15 | 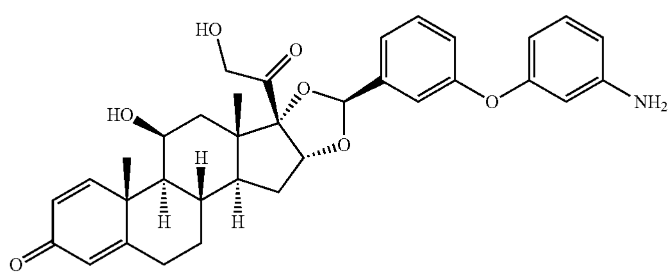 | 572.2 | A |
| 16 | 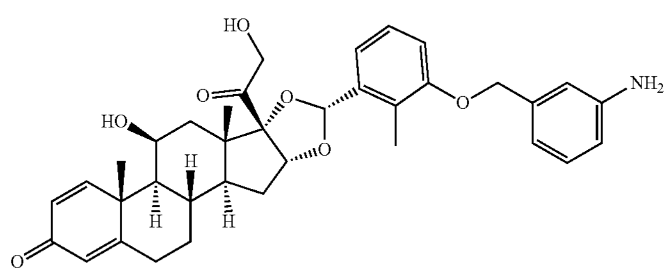 | 600.2 | A |
| 17 | 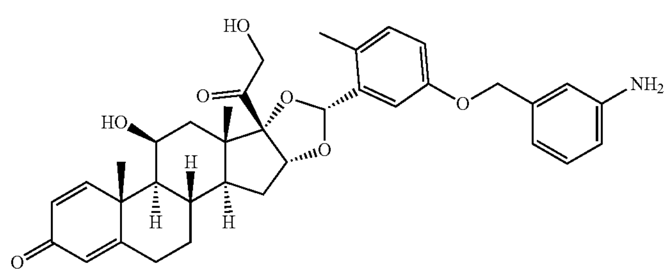 | 600.2 | A |

TABLE 18a-continued

Examples 6-158 (structures)

| Ex No. | Structure | ES/MS (m/z) (M + H) | Purification method* |
|---|---|---|---|
| 18 | 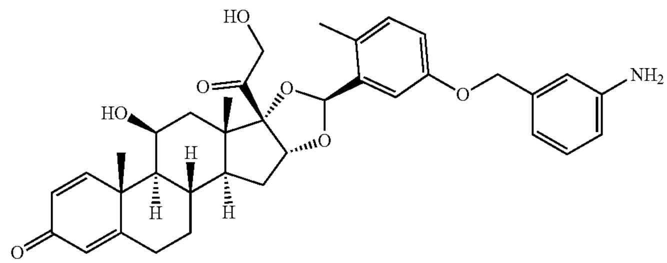 | 600.2 | A |
| 19 | 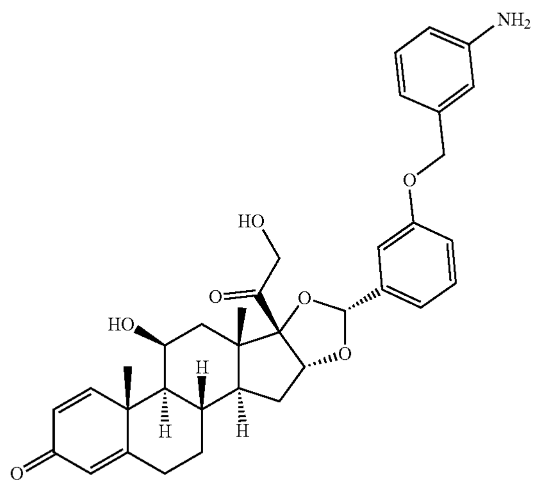 | 586.2 | A |
| 20 | 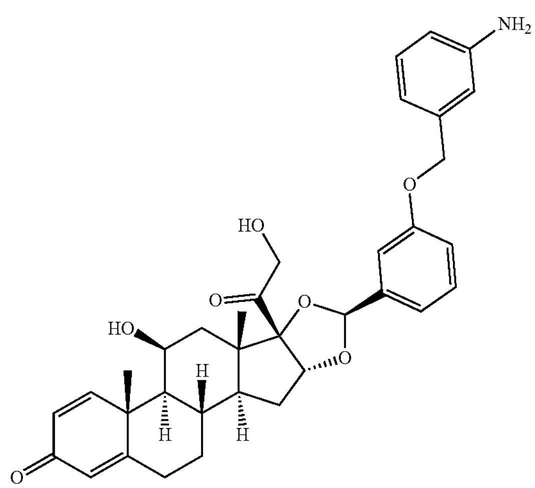 | 586.2 | A |
| 21 | 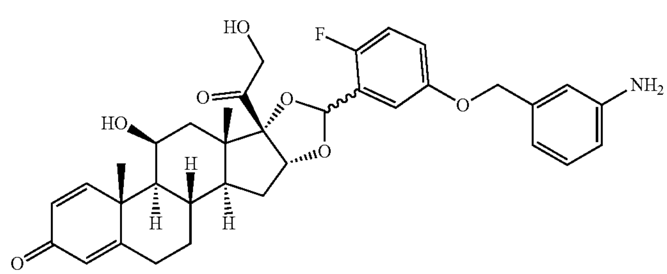 | 604.2 | A |

TABLE 18a-continued

Examples 6-158 (structures)

| Ex No. | Structure | ES/MS (m/z) (M + H) | Purification method* |
|---|---|---|---|
| 22 | 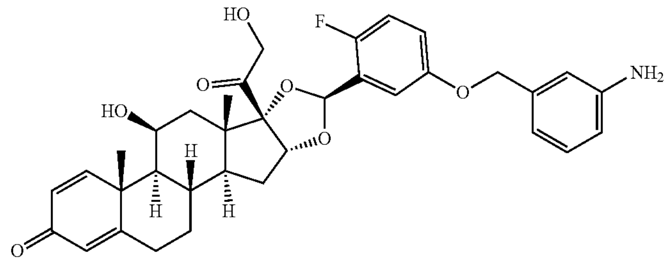 | 604.2 | A, O |
| 23 | 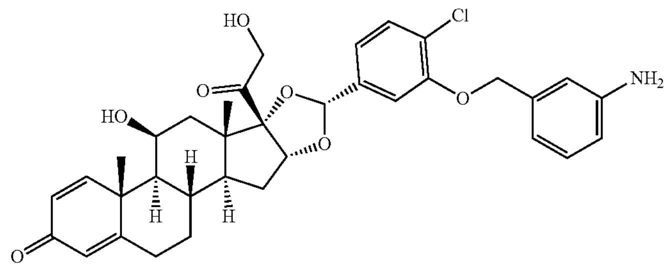 | 620.2 | A |
| 24 | 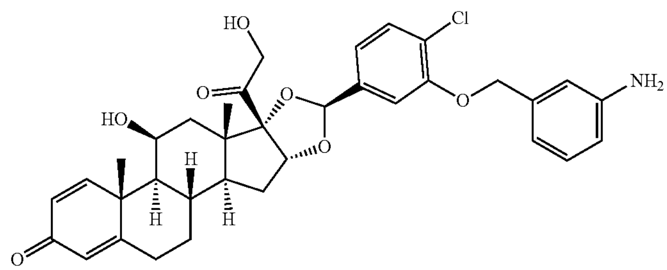 | 620.2 | A |
| 25 | 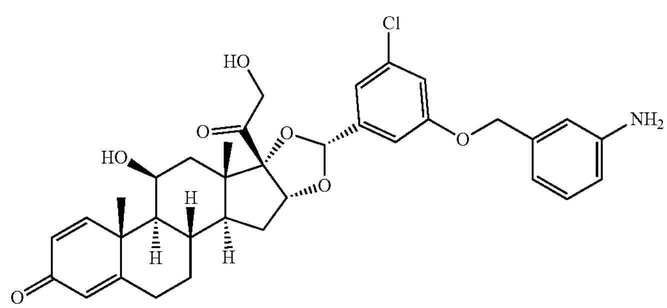 | 620.2 | A |
| 26 | 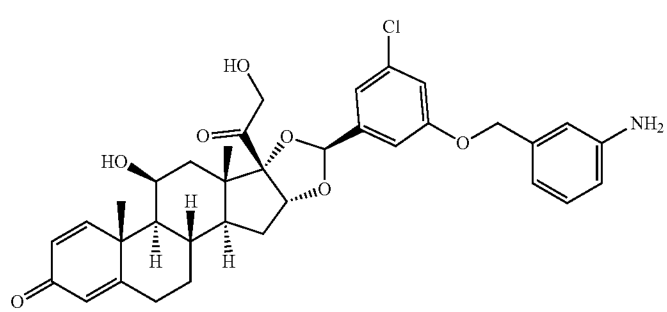 | 620.2 | A |

TABLE 18a-continued

Examples 6-158 (structures)

| Ex No. | Structure | ES/MS (m/z) (M + H) | Purification method* |
|---|---|---|---|
| 27 | 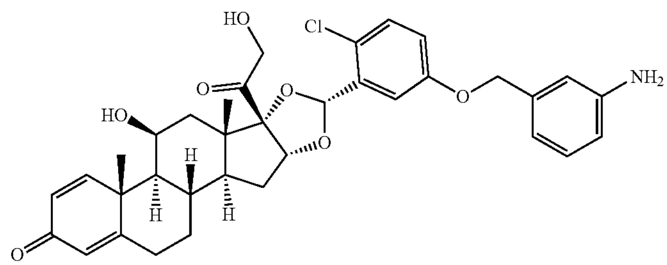 | 620.2 | A |
| 28 | 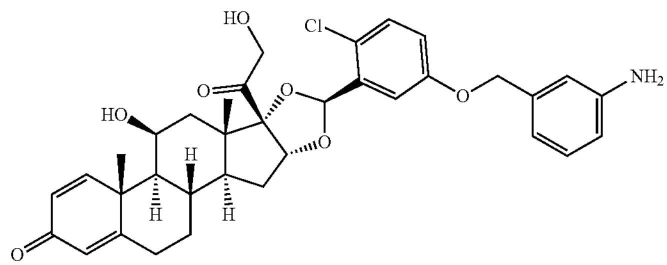 | 620.2 | A |
| 29 | 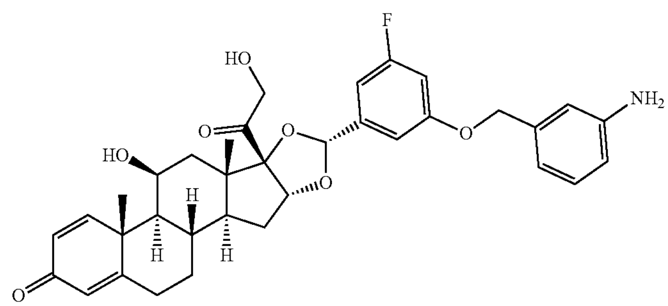 | 604.2 | A |
| 30 | 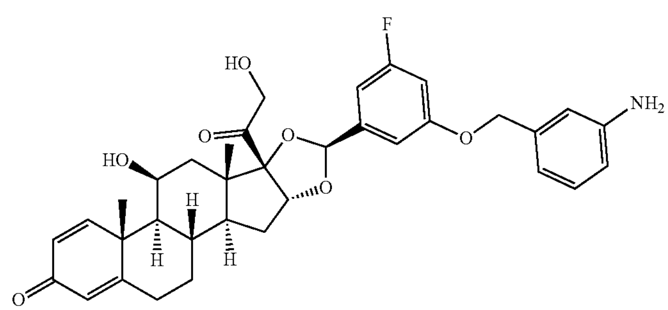 | 604.2 | A |
| 31 | 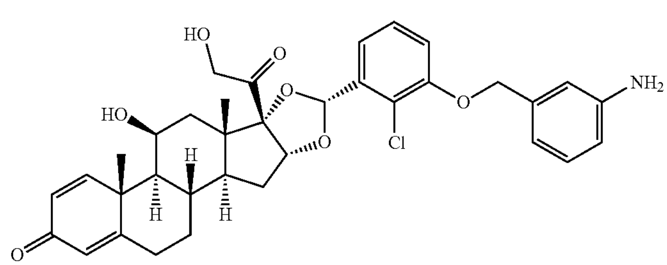 | 620.4 | M |

TABLE 18a-continued
Examples 6-158 (structures)
| Ex No. | Structure | ES/MS (m/z) (M + H) | Purification method* |
|---|---|---|---|
| 32 | 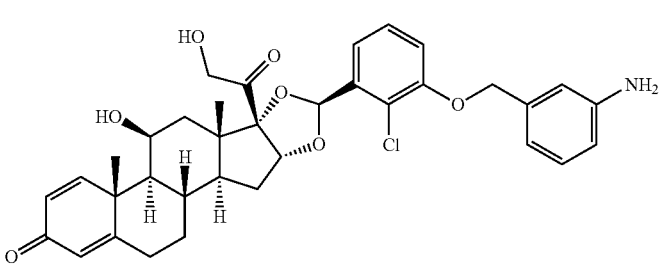 | 620.4 | M |
| 33 | 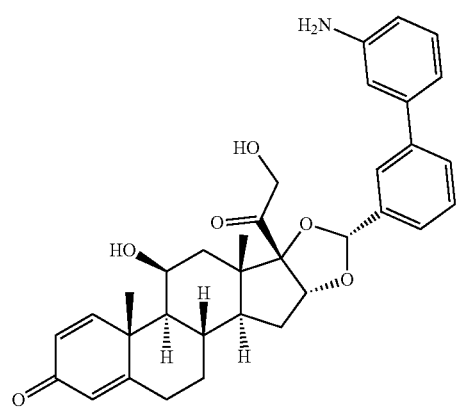 | 556.2 | A |
| 34 | 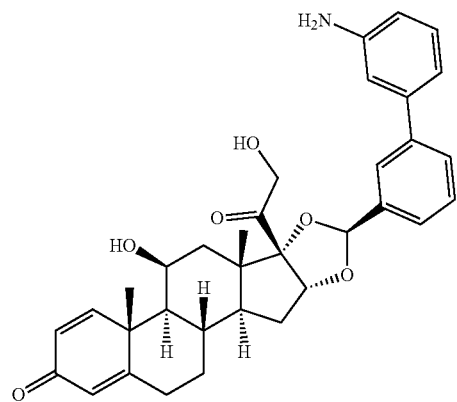 | 556.2 | A |
| 35 | 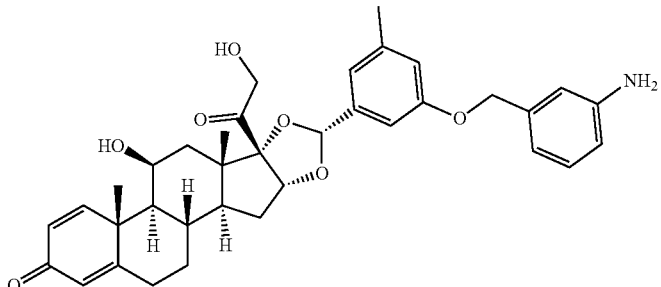 | 600.2 | A |

TABLE 18a-continued

Examples 6-158 (structures)

| Ex No. | Structure | ES/MS (m/z) (M + H) | Purification method* |
|---|---|---|---|
| 36 | 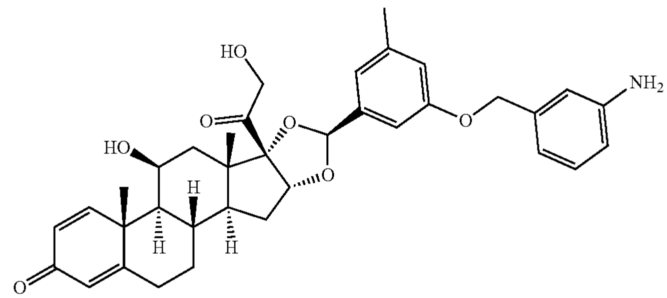 | 600.2 | A |
| 37 | 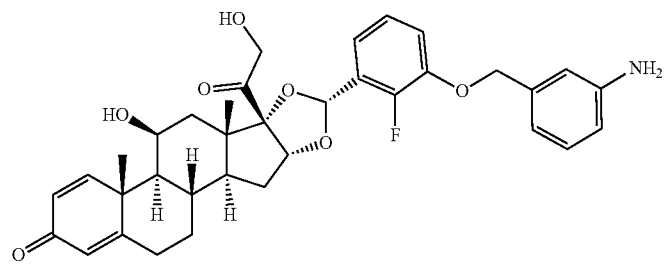 | 604.2 | A |
| 38 | 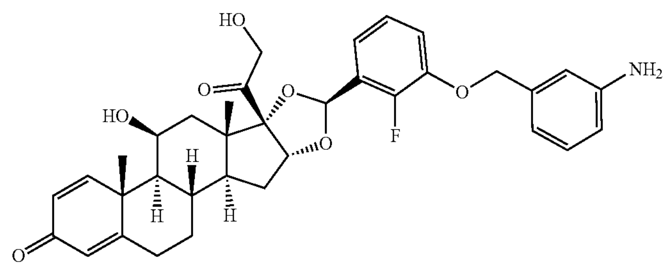 | 604.2 | A |
| 39 | 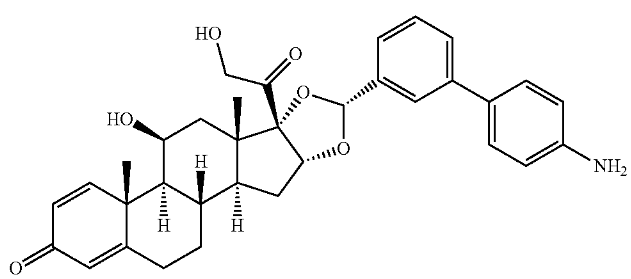 | 556.2 | A |
| 40 | 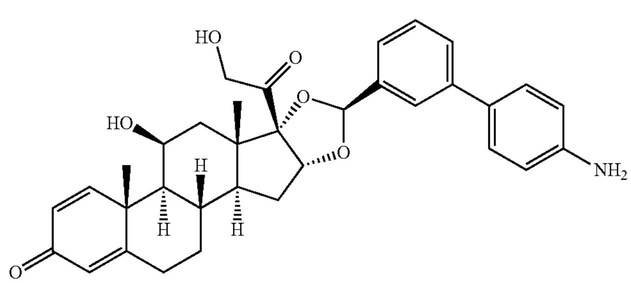 | 556.2 | A |

TABLE 18a-continued

Examples 6-158 (structures)

| Ex No. | Structure | ES/MS (m/z) (M + H) | Purification method* |
|---|---|---|---|
| 41 | 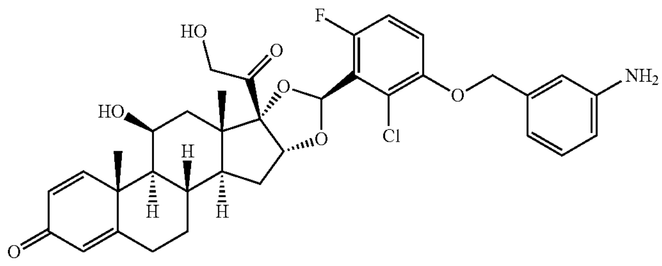 | 638.4 | A, L |
| 42 | 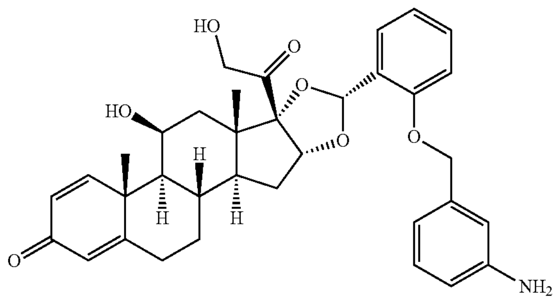 | 586.4 | A, L |
| 43 | 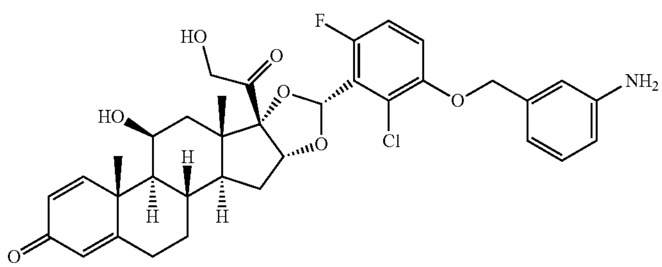 | 638.4 | A, L |
| 44 | 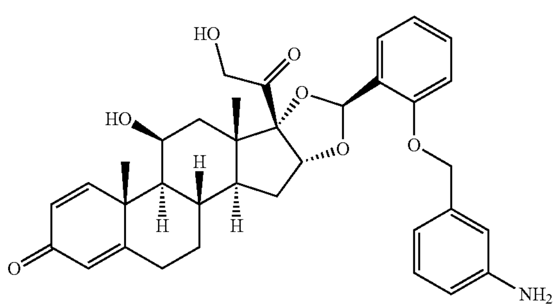 | 586.4 | A, L |
| 45 | 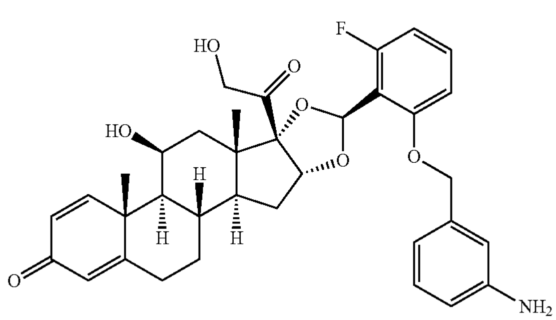 | 604.4 | A, O |

TABLE 18a-continued

Examples 6-158 (structures)

| Ex No. | Structure | ES/MS (m/z) (M + H) | Purification method* |
|---|---|---|---|
| 46 | 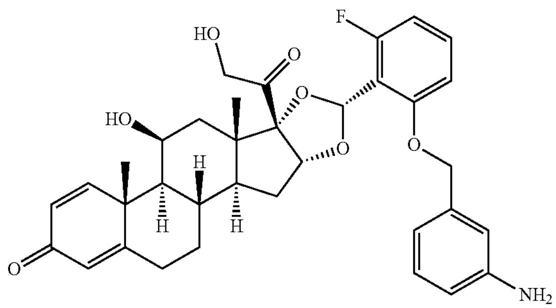 | 604.4 | A, O |
| 47 | 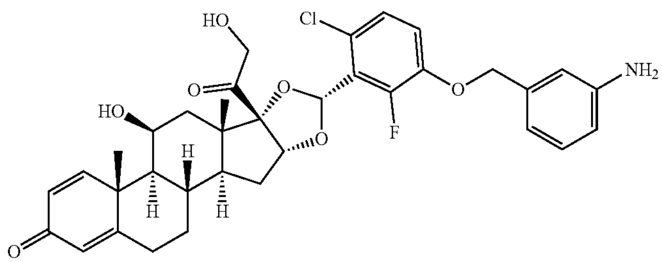 | 638.2 | A |
| 48 | 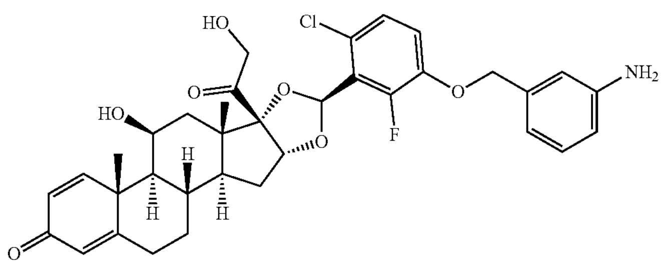 | 638.2 | A |
| 49 | 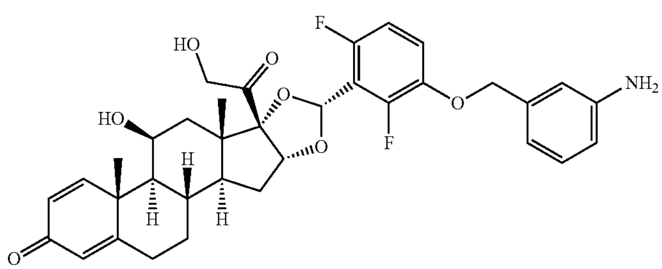 | 622.3 | A |
| 50 | 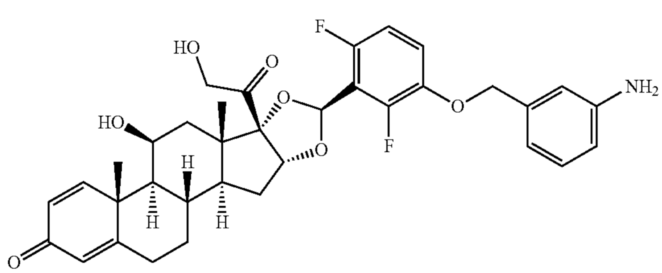 | 622.3 | A |

TABLE 18a-continued

Examples 6-158 (structures)

| Ex No. | Structure | ES/MS (m/z) (M + H) | Purification method* |
|---|---|---|---|
| 51 | 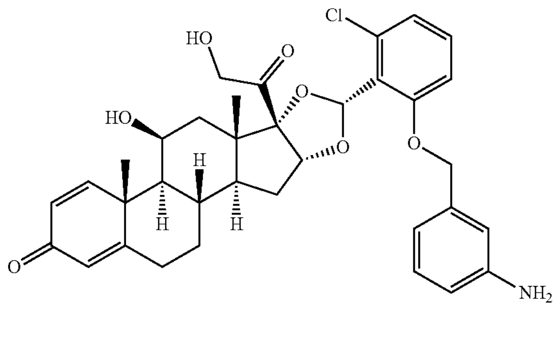 | 620.5 | A, O |
| 52 | 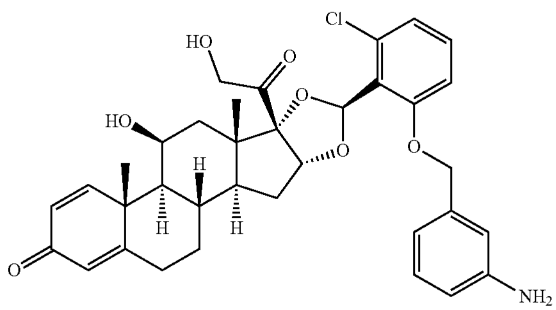 | 620.5 | A, O |
| 53 | 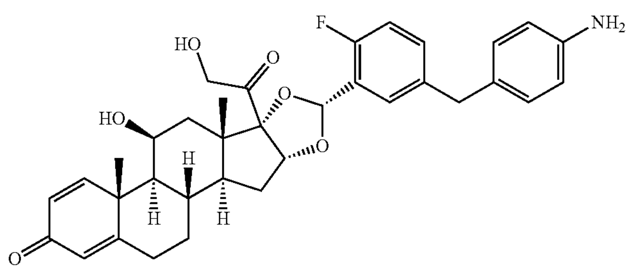 | 588.2 | A |
| 54 | 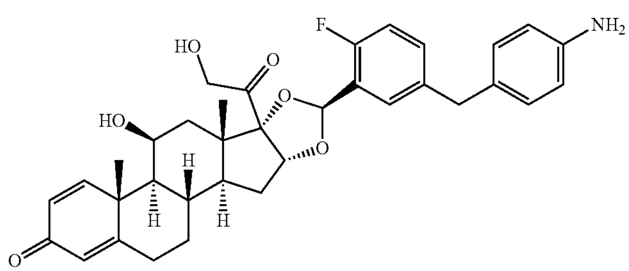 | 588.2 | A |

TABLE 18a-continued

Examples 6-158 (structures)

| Ex No. | Structure | ES/MS (m/z) (M + H) | Purification method* |
|---|---|---|---|
| 55 | 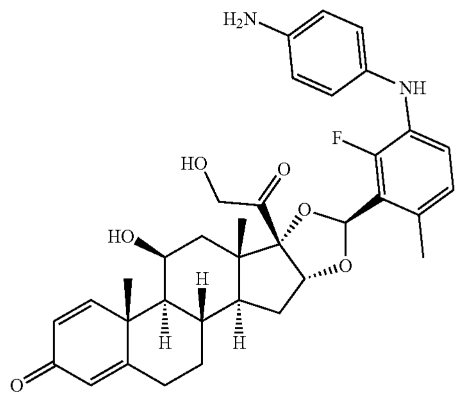 | 617.5 | B, C |
| 56 | 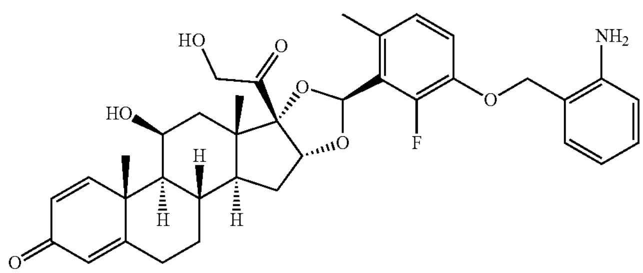 | 618.4 | A |
| 57 | 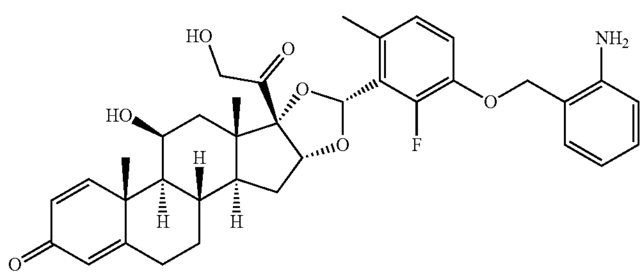 | 618.4 | A |
| 58 | 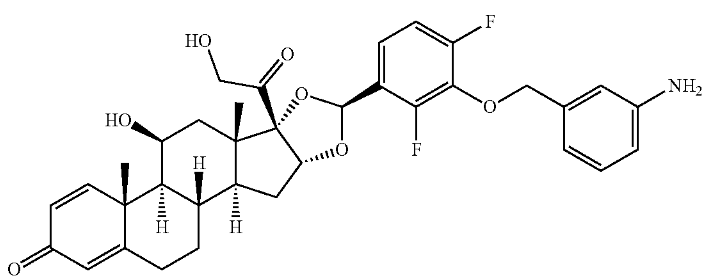 | 622.0 | A |
| 59 | 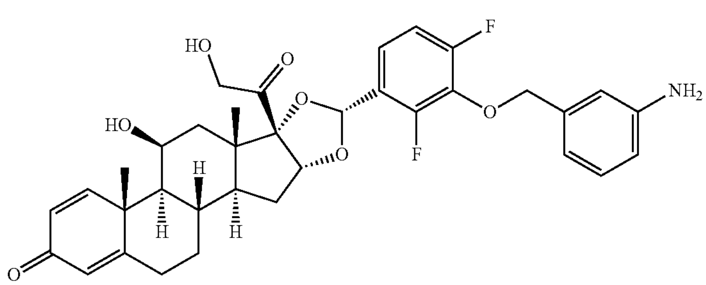 | 622.4 | A |

TABLE 18a-continued

Examples 6-158 (structures)

| Ex No. | Structure | ES/MS (m/z) (M + H) | Purification method* |
|---|---|---|---|
| 60 | 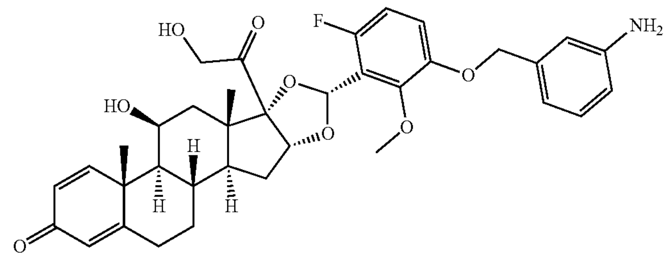 | 634.3 | A |
| 61 | 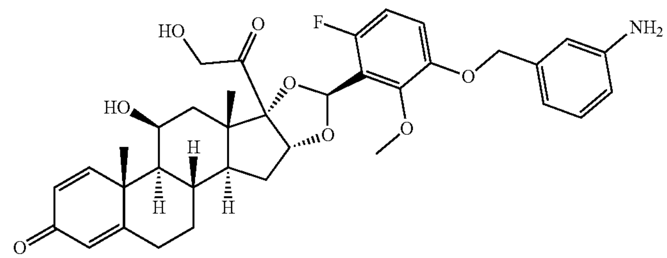 | 634.3 | A |
| 62 | 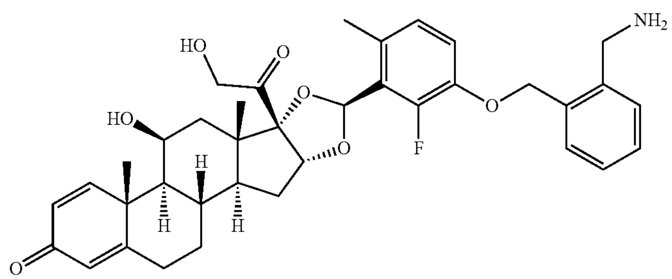 | 632.4 | A |
| 63 | 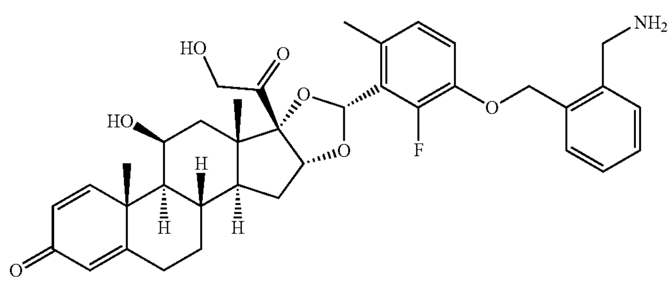 | 632.4 | A |
| 64 | 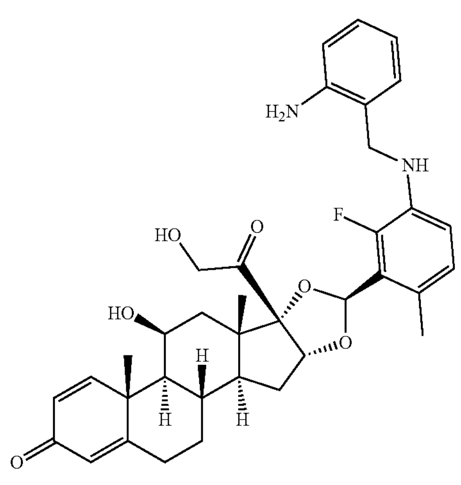 | 617.6 | B, J |

TABLE 18a-continued

Examples 6-158 (structures)

| Ex No. | Structure | ES/MS (m/z) (M + H) | Purification method* |
|---|---|---|---|
| 65 | 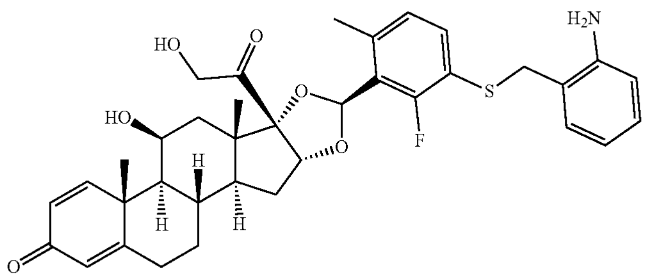 | 634.5 | B |
| 66 | 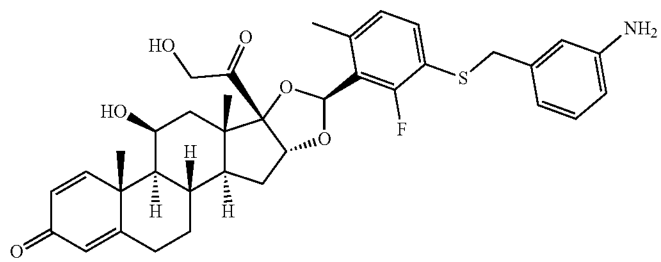 | 634.5 | B |
| 67 | 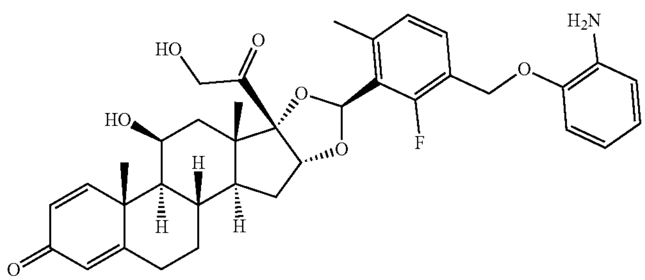 | 618.5 | B, I |
| 68 | 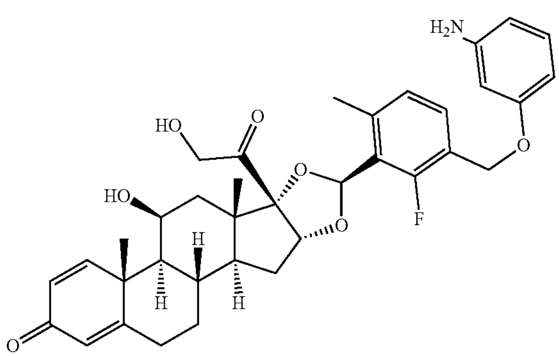 | 618.5 | B |
| 69 | 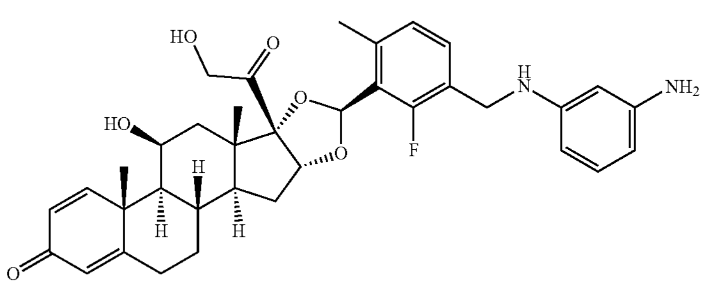 | 617.5 | B |

TABLE 18a-continued

Examples 6-158 (structures)

| Ex No. | Structure | ES/MS (m/z) (M + H) | Purification method* |
|---|---|---|---|
| 70 | 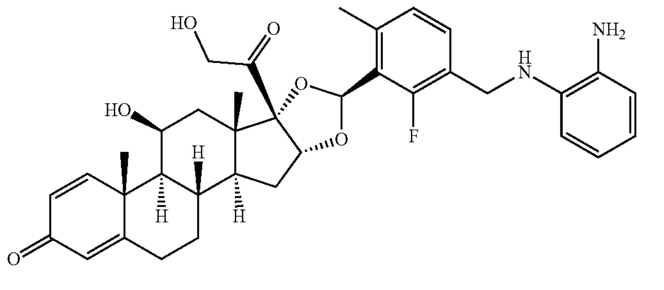 | 617.0 | B, K |
| 71 | 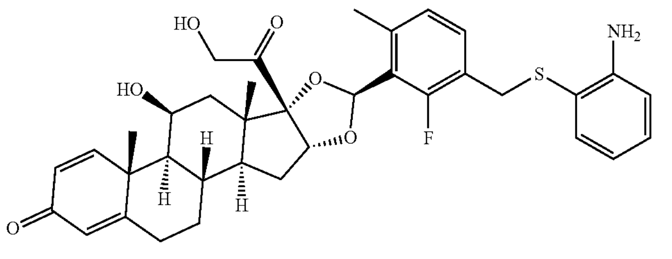 | 634.5 | A, G |
| 72 | 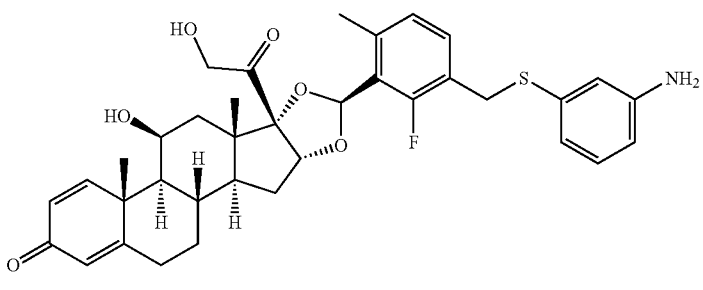 | 634.1 | B, H |
| 73 | 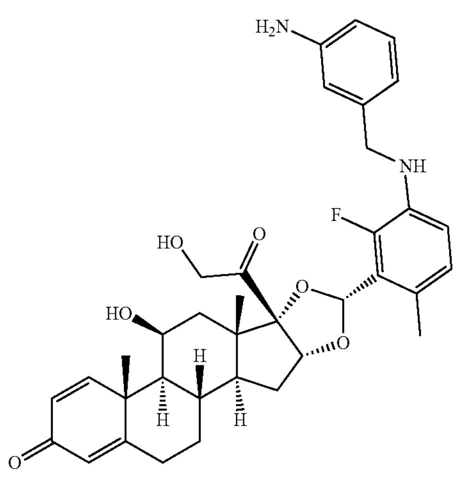 | 617.5 | B, C |

TABLE 18a-continued

Examples 6-158 (structures)

| Ex No. | Structure | ES/MS (m/z) (M + H) | Purification method* |
|---|---|---|---|
| 74 | 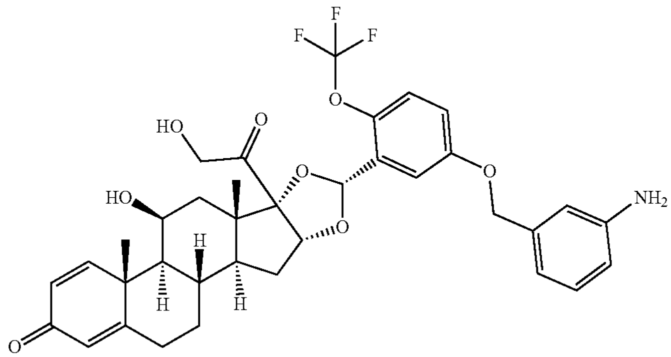 | 670.4 | A |
| 75 | 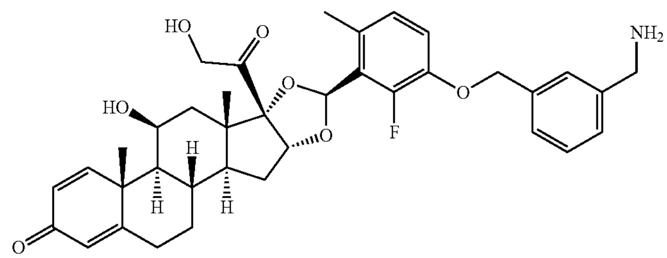 | 632.2 | A |
| 76 | 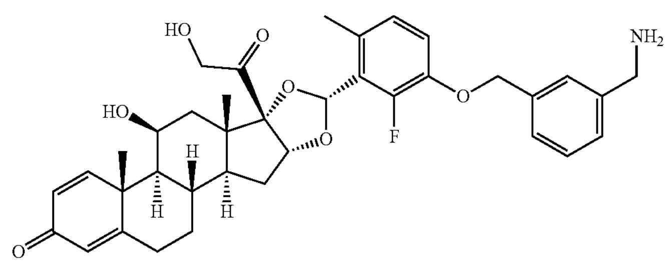 | 632.2 | A |
| 77 | 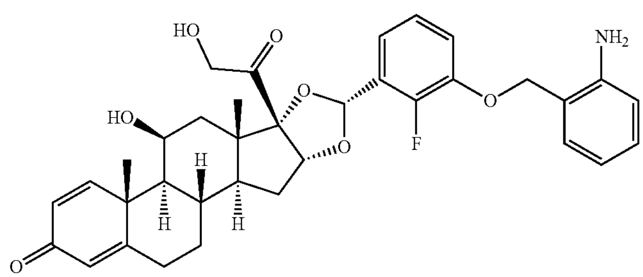 | 604.4 | A |
| 78 | 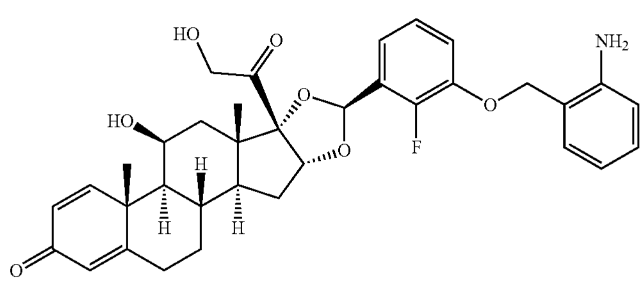 | 604.3 | A |

TABLE 18a-continued

Examples 6-158 (structures)

| Ex No. | Structure | ES/MS (m/z) (M + H) | Purification method* |
|---|---|---|---|
| 79 | 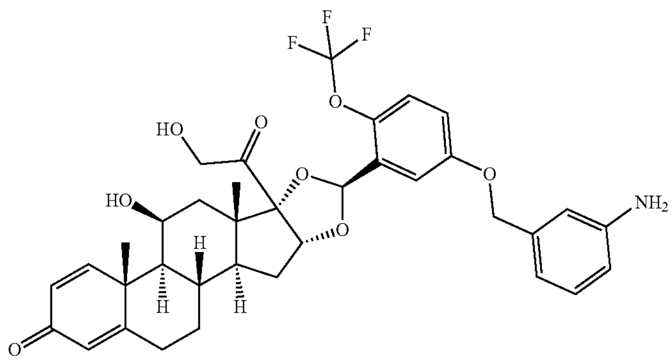 | 670.4 | A |
| 80 | 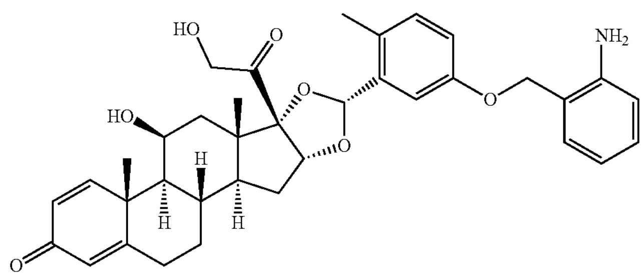 | 600.6 | A |
| 81 | 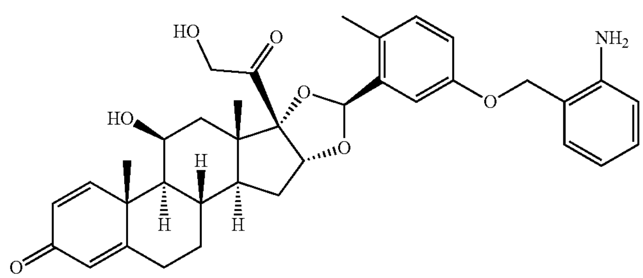 | 600.6 | A |
| 82 | 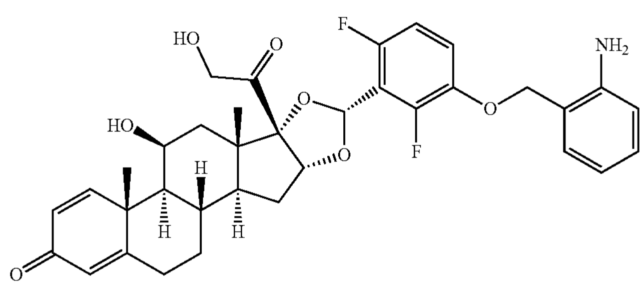 | 622.4 | A |
| 83 | 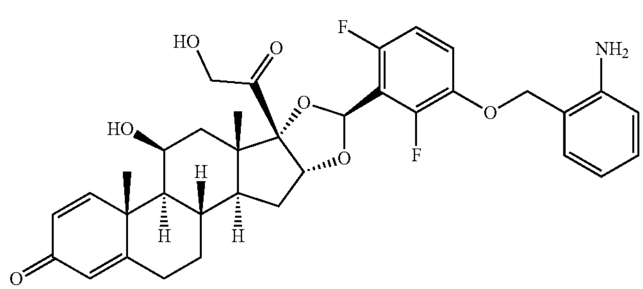 | 622.3 | A |

TABLE 18a-continued

Examples 6-158 (structures)

| Ex No. | Structure | ES/MS (m/z) (M + H) | Purification method* |
|---|---|---|---|
| 84 | | 632.4 | B, H |
| 85 | | 632.4 | A |
| 86 | | 631.5 | B, G |
| 87 | | 616.5 | B |

TABLE 18a-continued

Examples 6-158 (structures)

| Ex No. | Structure | ES/MS (m/z) (M + H) | Purification method* |
|---|---|---|---|
| 88 | 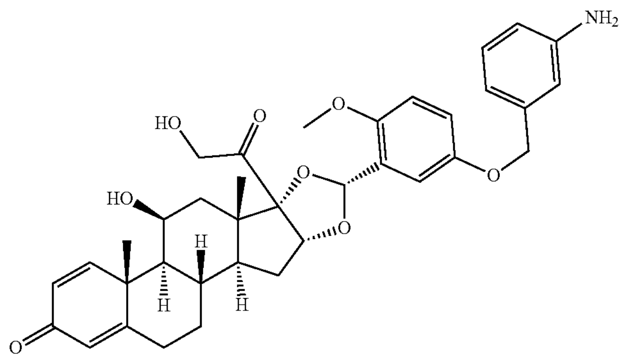 | 616.4 | A |
| 89 | 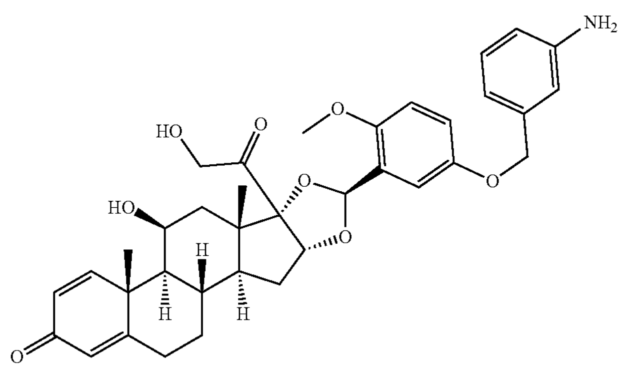 | 616.4 | A |
| 90 | 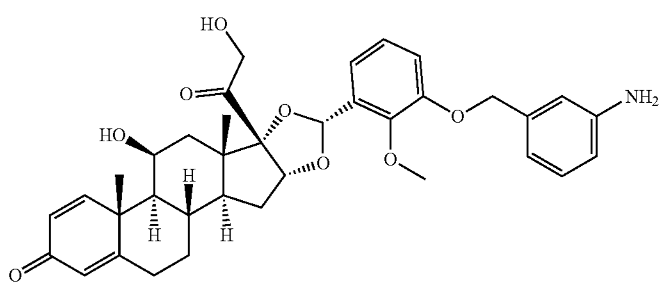 | 616.4 | A |
| 91 | 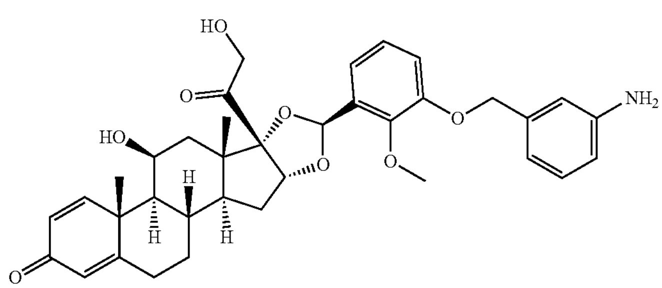 | 616.6 | A |

TABLE 18a-continued

Examples 6-158 (structures)

| Ex No. | Structure | ES/MS (m/z) (M + H) | Purification method* |
|---|---|---|---|
| 92 | 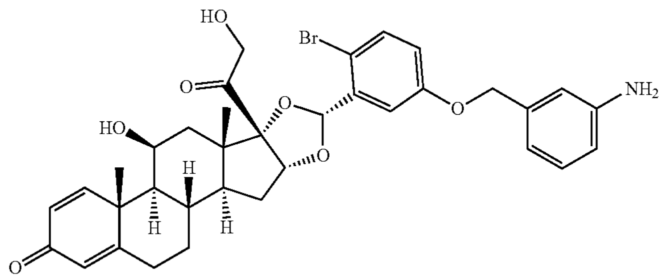 | 664.4 | A |
| 93 | 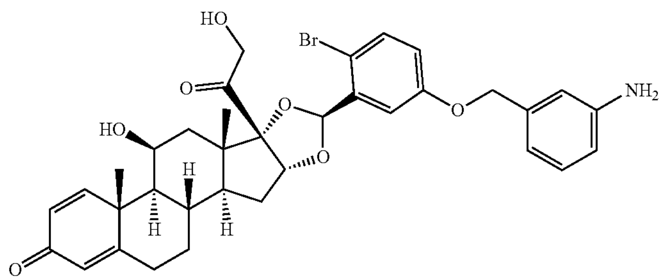 | 664.4 | A |
| 94 | 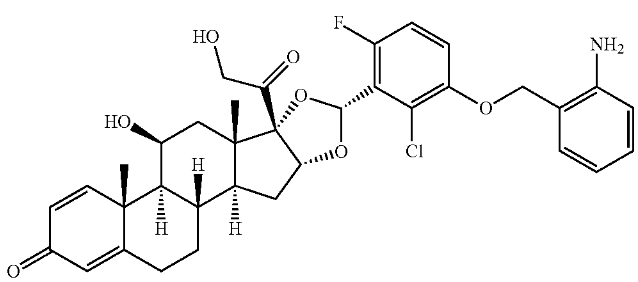 | 638.4 | D |
| 95 | 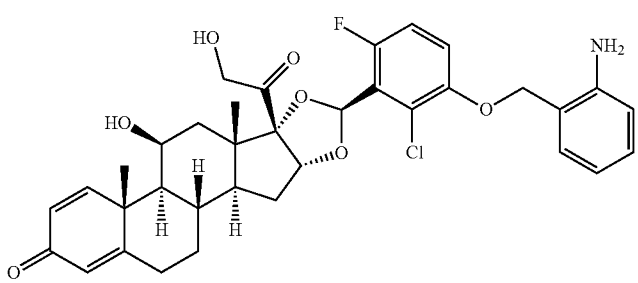 | 638.4 | D |
| 96 | 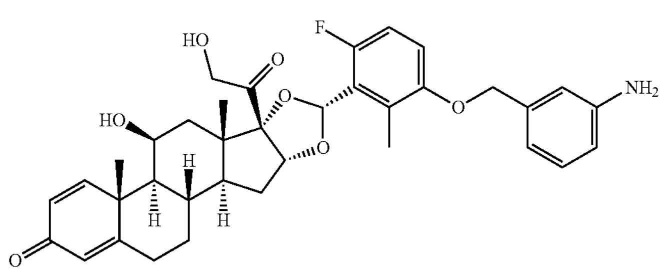 | 618.6 | N |

TABLE 18a-continued

Examples 6-158 (structures)

| Ex No. | Structure | ES/MS (m/z) (M + H) | Purification method* |
|---|---|---|---|
| 97 | 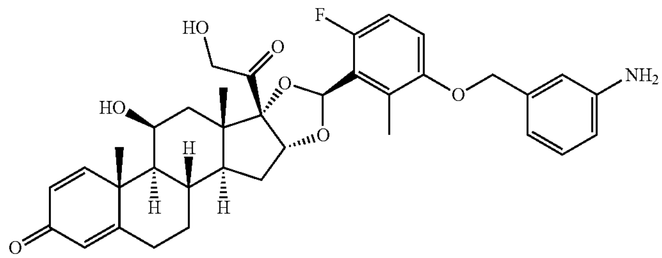 | 618.6 | N |
| 98 | 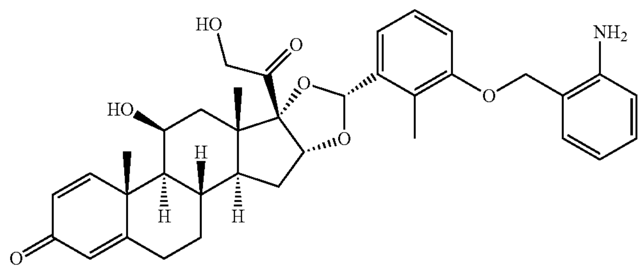 | 600.2 | B |
| 99 | 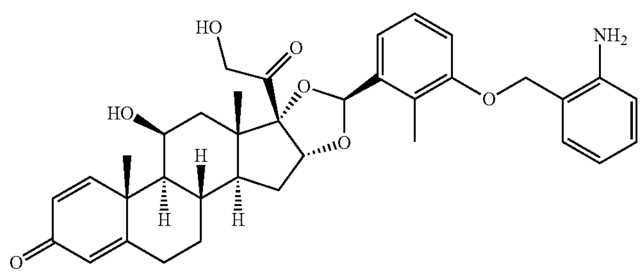 | 600.2 | B |
| 100 | 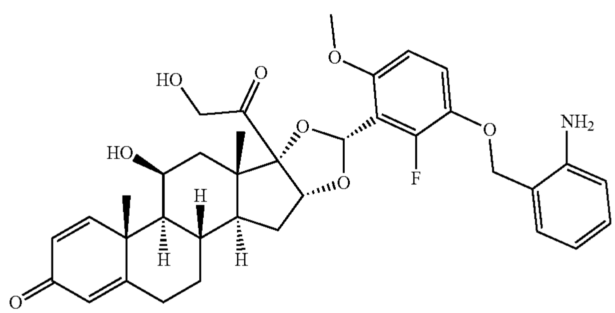 | 634.4 | A |
| 101 | 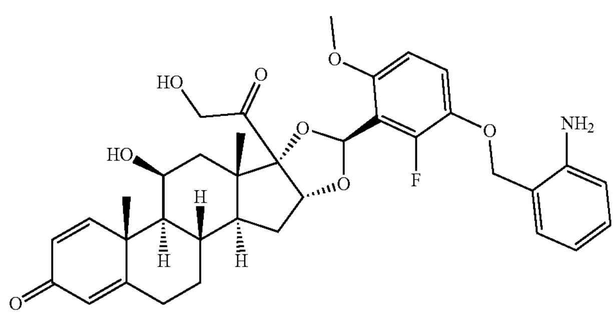 | 634.4 | A |

TABLE 18a-continued

Examples 6-158 (structures)

| Ex No. | Structure | ES/MS (m/z) (M + H) | Purification method* |
|---|---|---|---|
| 102 | 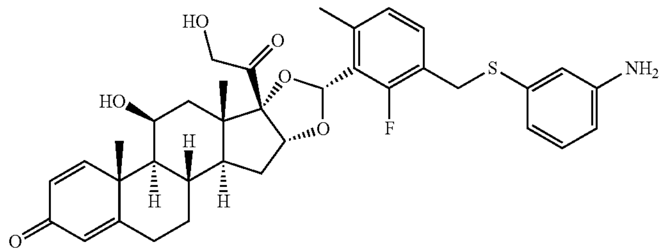 | 634.5 | B, H |
| 103 | 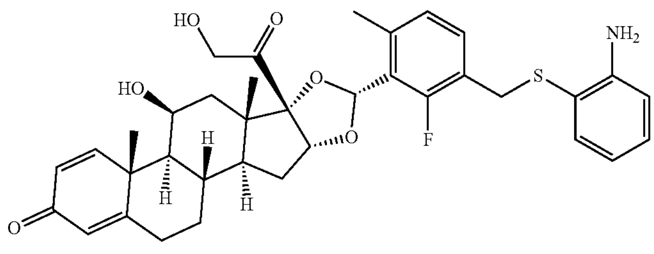 | 634.5 | B, G |
| 104 | 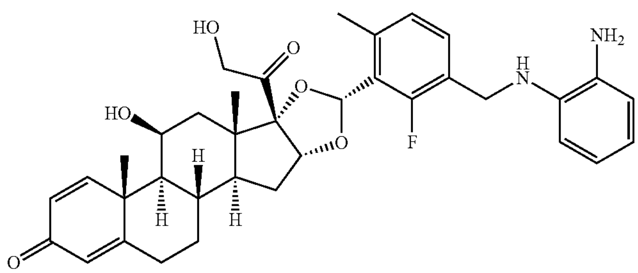 | 617.1 | B, K |
| 105 | 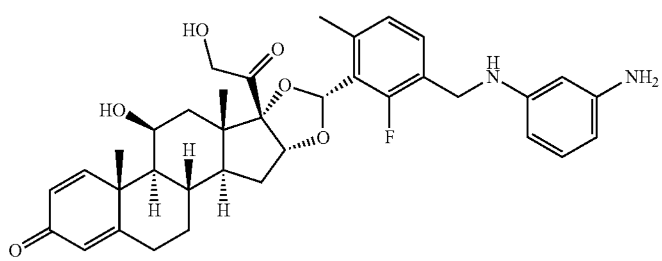 | 617.5 | B |
| 106 | 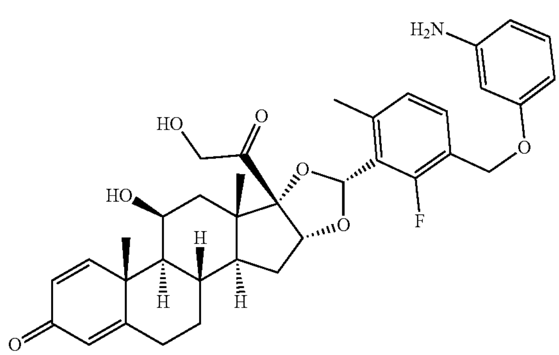 | 618.5 | B |

TABLE 18a-continued

Examples 6-158 (structures)

| Ex No. | Structure | ES/MS (m/z) (M + H) | Purification method* |
|---|---|---|---|
| 107 | 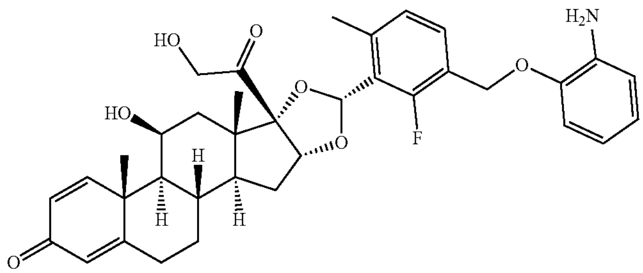 | 618.5 | B, I |
| 108 | 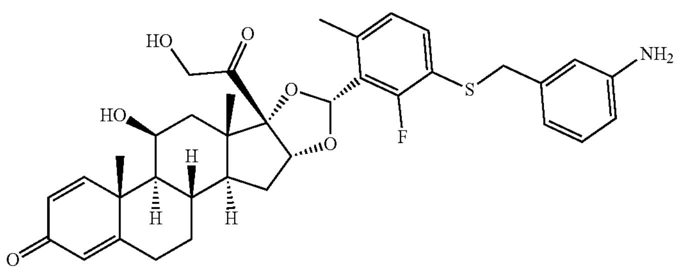 | 634.5 | B |
| 109 | 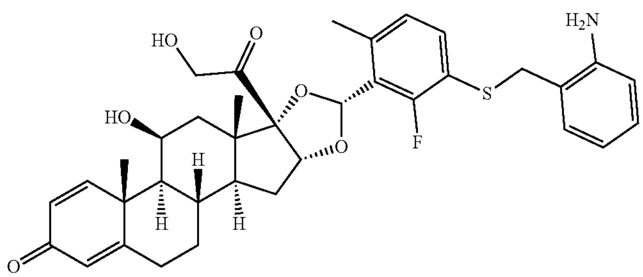 | 634.5 | B |
| 110 | 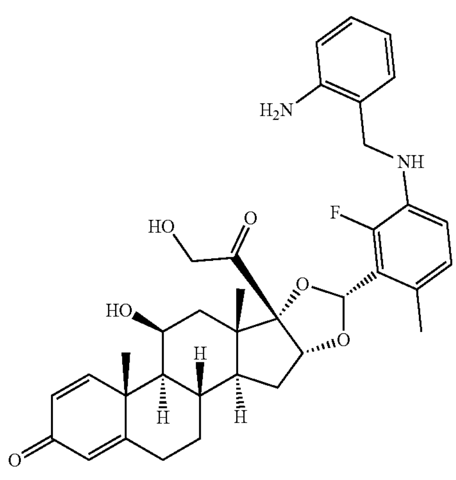 | 617.6 | B, J |
| 111 | 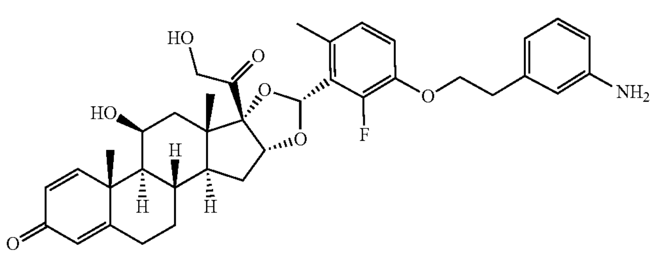 | 632.2 | A |

TABLE 18a-continued

Examples 6-158 (structures)

| Ex No. | Structure | ES/MS (m/z) (M + H) | Purification method* |
|---|---|---|---|
| 112 | 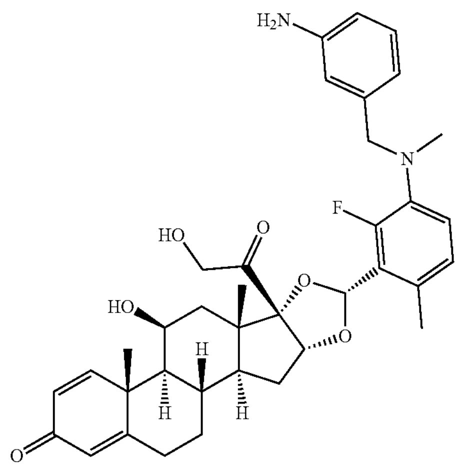 | 631.4 | B, G |
| 113 | 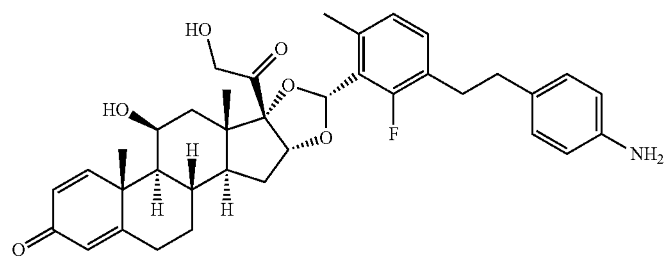 | 616.5 | B |
| 114 | 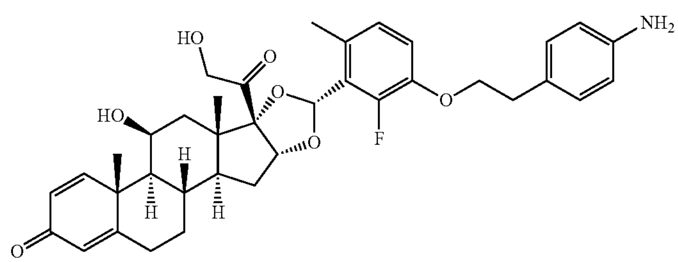 | 632.4 | B, H |
| 115 | 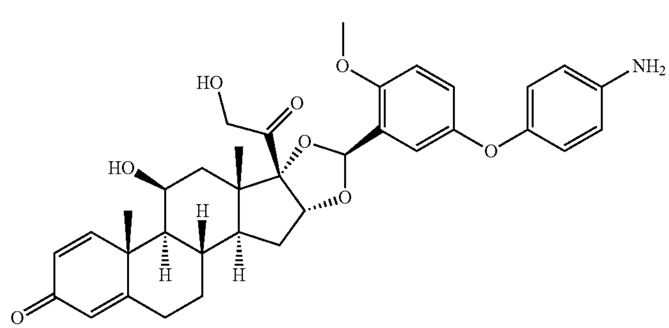 | 602.2 | A |

TABLE 18a-continued

Examples 6-158 (structures)

| Ex No. | Structure | ES/MS (m/z) (M + H) | Purification method* |
|---|---|---|---|
| 116 | 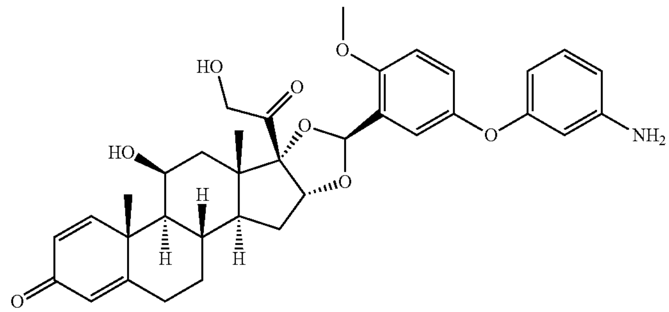 | 602.2 | A |
| 117 | 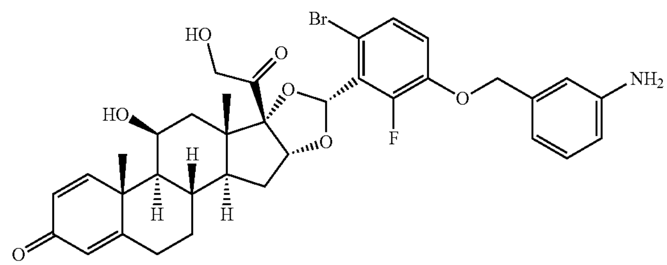 | 682.2 | A |
| 118 | 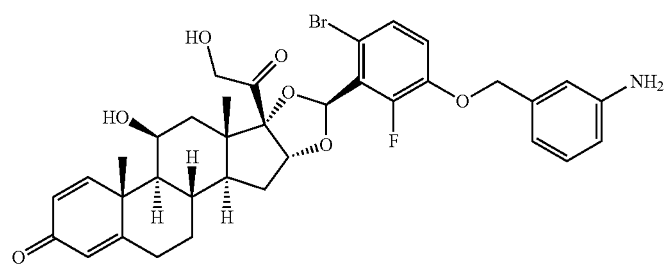 | 682.2 | A |
| 119 | 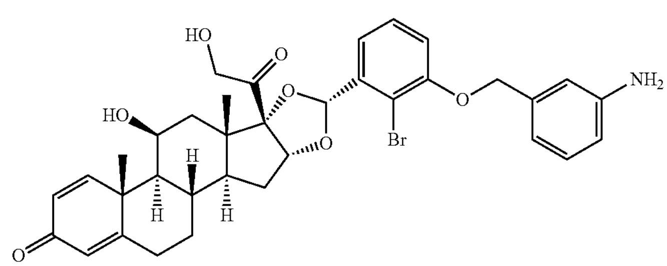 | 666.4 | F |
| 120 | 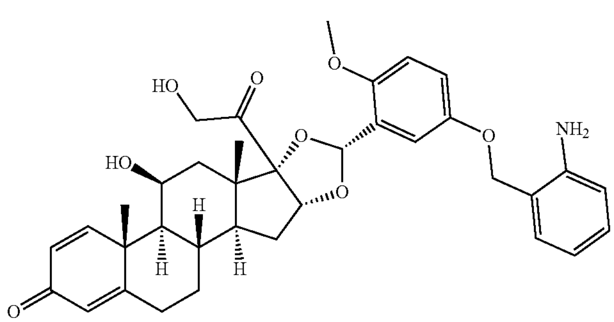 | 616.4 | A |

TABLE 18a-continued

Examples 6-158 (structures)

| Ex No. | Structure | ES/MS (m/z) (M + H) | Purification method* |
|---|---|---|---|
| 121 | 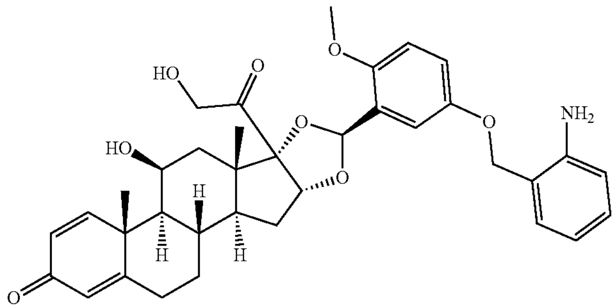 | 616.4 | A |
| 122 | 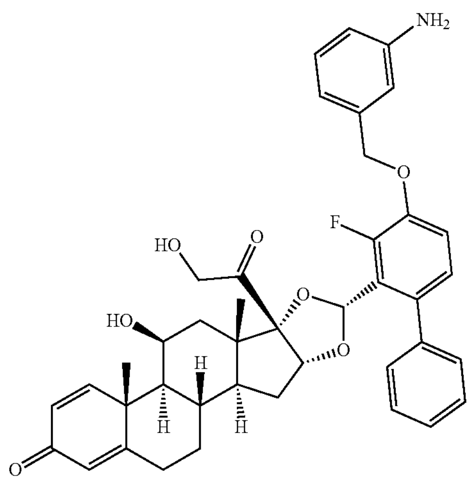 | 680.6 | B |
| 123 | 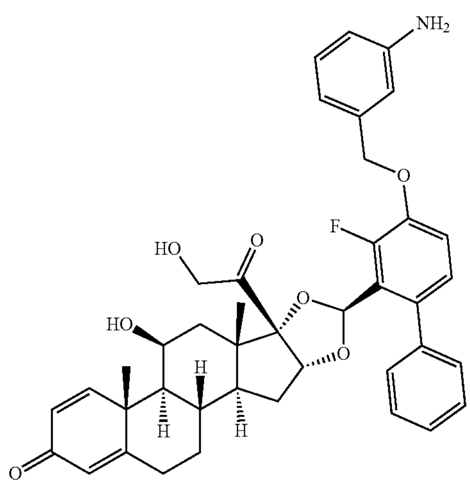 | 679.8 | B |

TABLE 18a-continued

Examples 6-158 (structures)

| Ex No. | Structure | ES/MS (m/z) (M + H) | Purification method* |
|---|---|---|---|
| 124 | 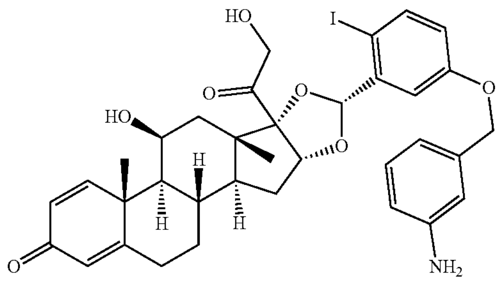 | 711.6 | A |
| 125 | 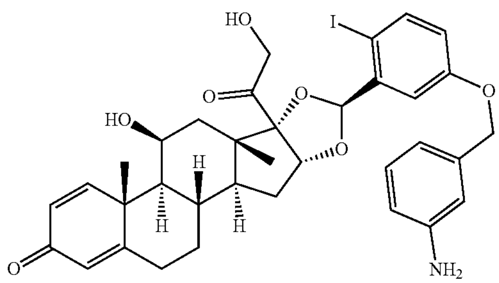 | 712.0 | A |
| 126 | 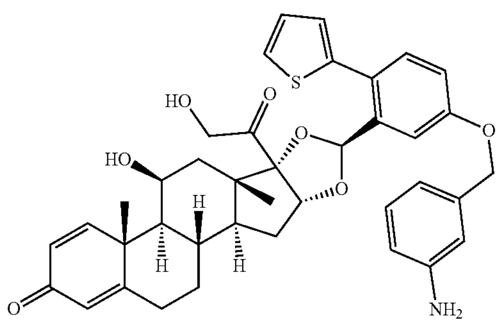 | 667.8 | B |
| 127 | 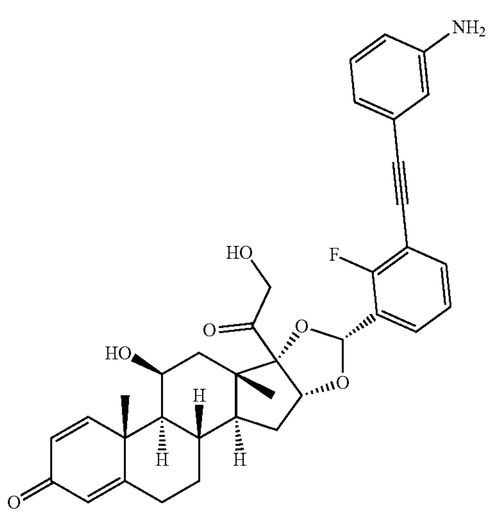 | 597.8 | A |

TABLE 18a-continued

Examples 6-158 (structures)

| Ex No. | Structure | ES/MS (m/z) (M + H) | Purification method* |
|---|---|---|---|
| 128 | 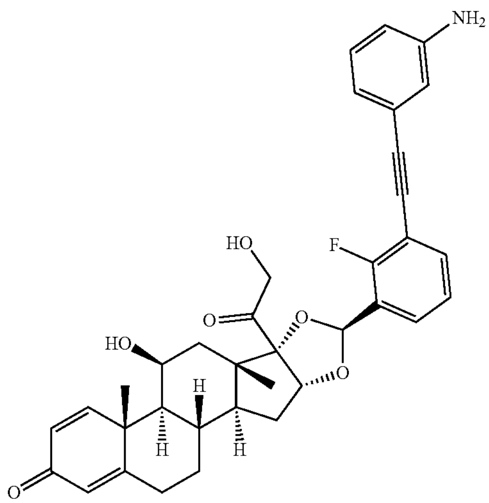 | 597.8 | A |
| 129 | 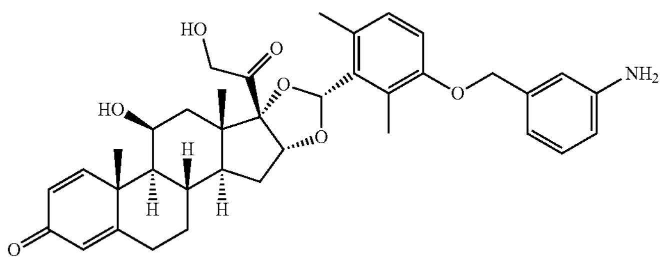 | 614.6 | F |
| 130 | 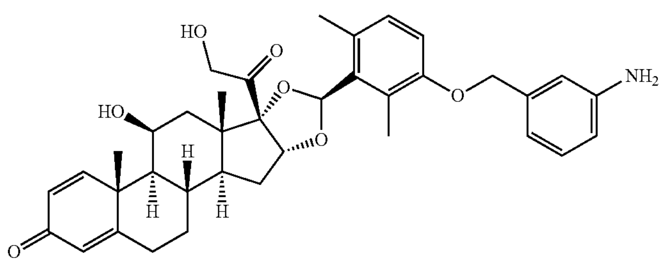 | 614.6 | F |
| 131 | 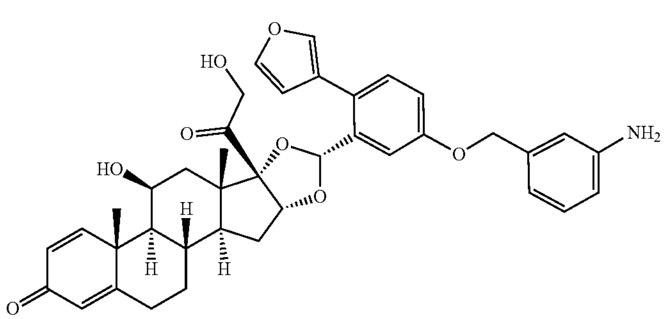 | 651.8 | B |

TABLE 18a-continued

Examples 6-158 (structures)

| Ex No. | Structure | ES/MS (m/z) (M + H) | Purification method* |
|---|---|---|---|
| 132 | 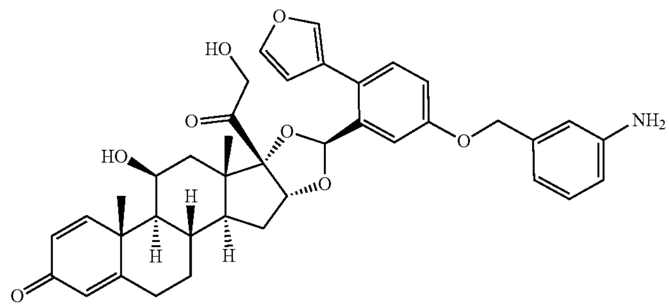 | 651.8 | B |
| 133 | 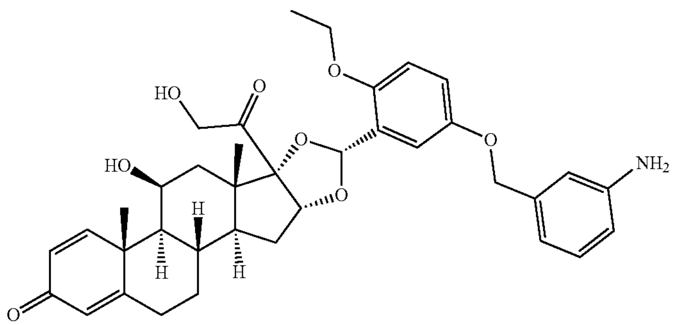 | 630.4 | A |
| 134 | 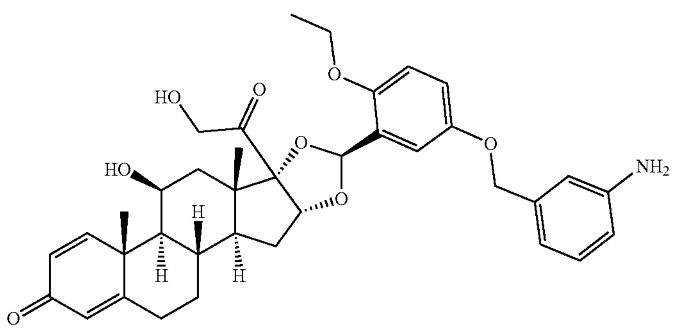 | 630.4 | A |
| 135 | 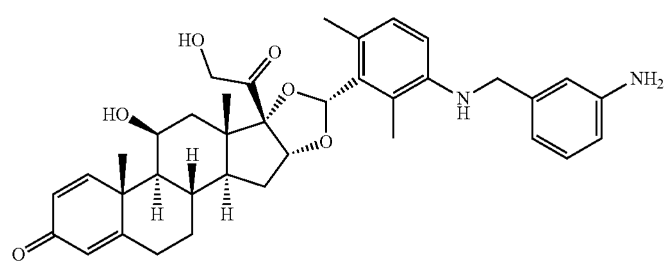 | 613.6 | E |
| 136 | 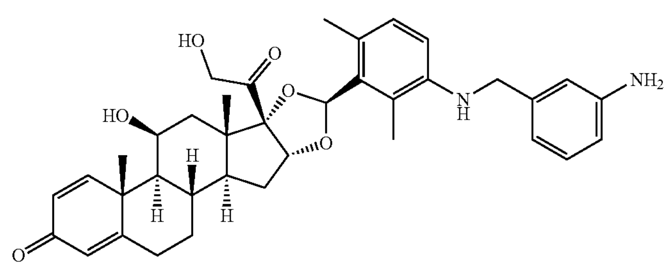 | 613.6 | E |

TABLE 18a-continued

Examples 6-158 (structures)

| Ex No. | Structure | ES/MS (m/z) (M + H) | Purification method* |
|---|---|---|---|
| 137 | 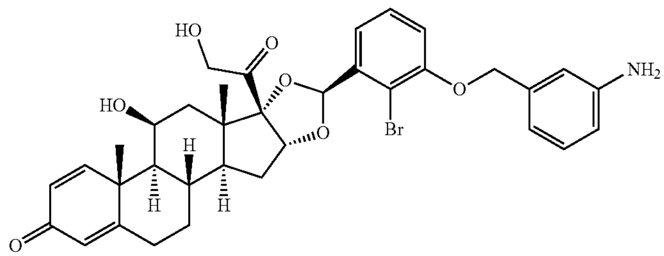 | 666.4 | F |
| 138 | 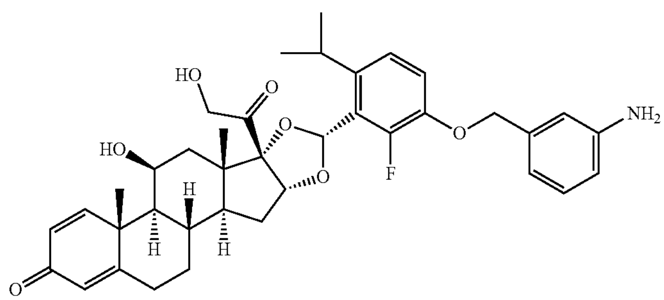 | 646.4 | A |
| 139 | 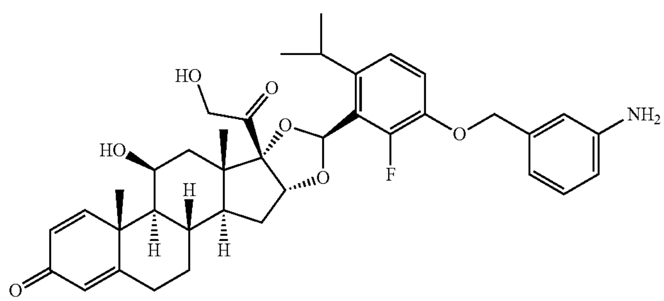 | 646.4 | A |
| 140 | 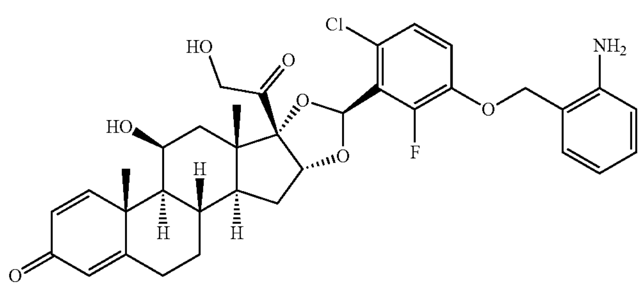 | 638.1 | A |
| 141 | 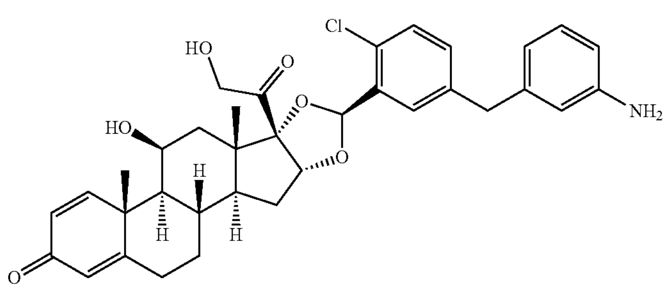 | 604.4 | A |

TABLE 18a-continued

Examples 6-158 (structures)

| Ex No. | Structure | ES/MS (m/z) (M + H) | Purification method* |
|---|---|---|---|
| 142 | 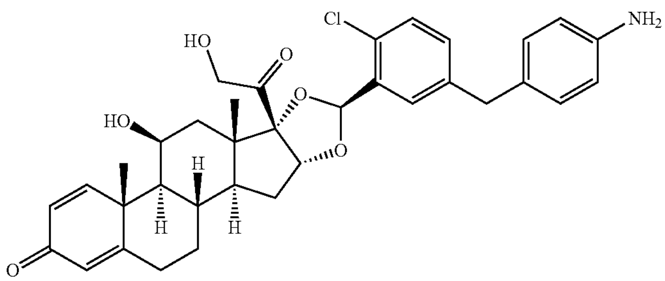 | 604.4 | A |
| 143 | 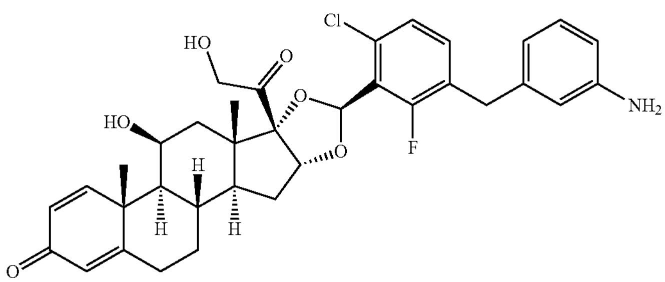 | 622.2 | A |
| 144 | 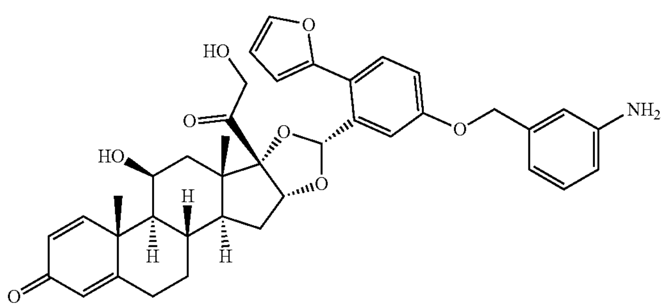 | 651.8 | B |
| 145 | 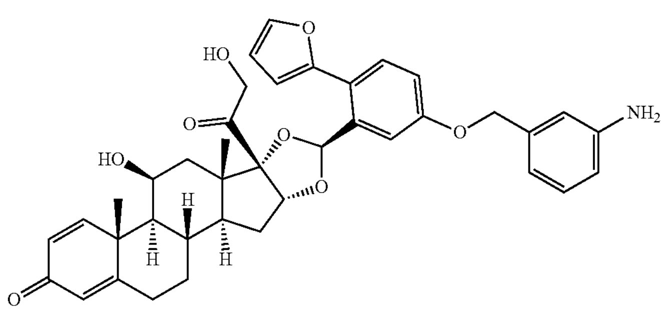 | 651.8 | B |
| 146 | 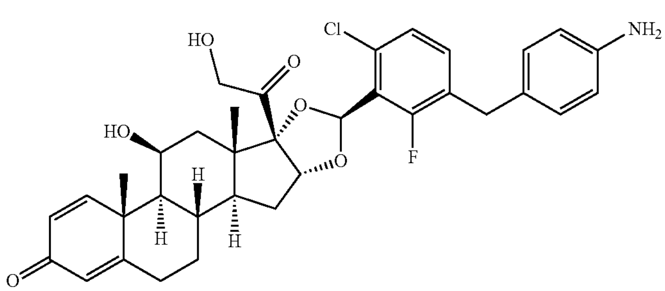 | 622.0 | A |

TABLE 18a-continued

Examples 6-158 (structures)

| Ex No. | Structure | ES/MS (m/z) (M + H) | Purification method* |
|---|---|---|---|
| 147 | 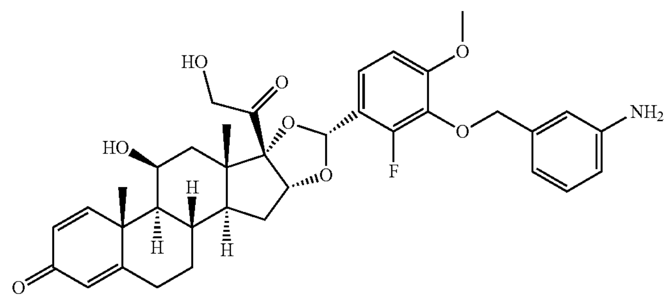 | 634.2 | A |
| 148 | 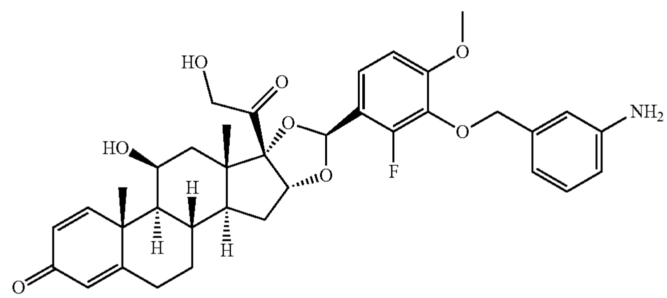 | 634.4 | A |
| 149 | 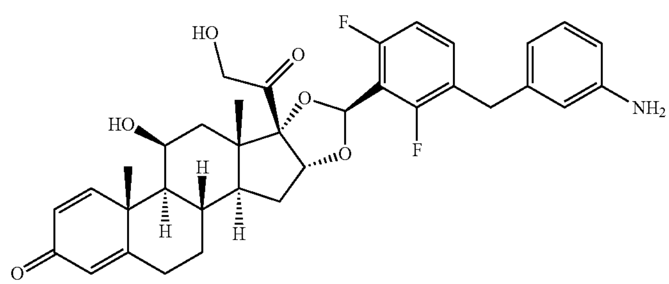 | 606.4 | A |
| 150 | 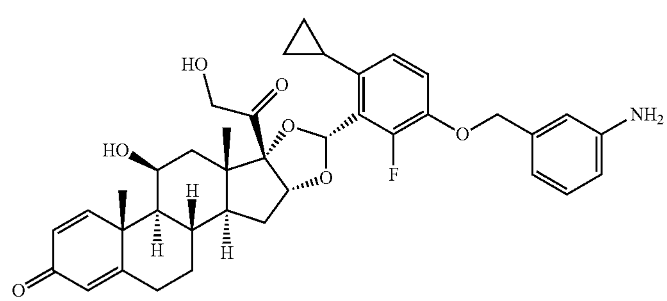 | 644.4 | A |
| 151 | 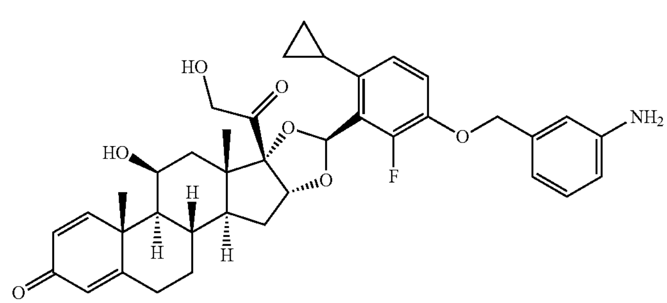 | 644.4 | A |

TABLE 18a-continued

Examples 6-158 (structures)

| Ex No. | Structure | ES/MS (m/z) (M + H) | Purification method* |
|---|---|---|---|
| 152 | 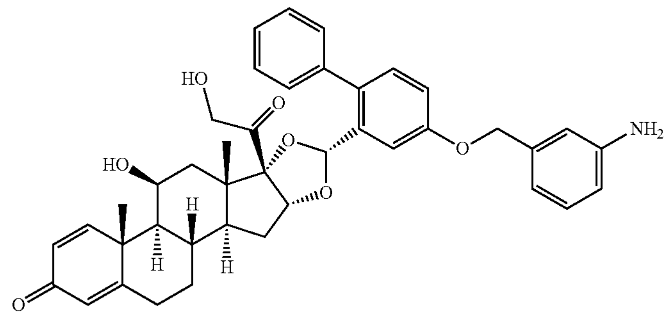 | 662.4 | A |
| 153 | 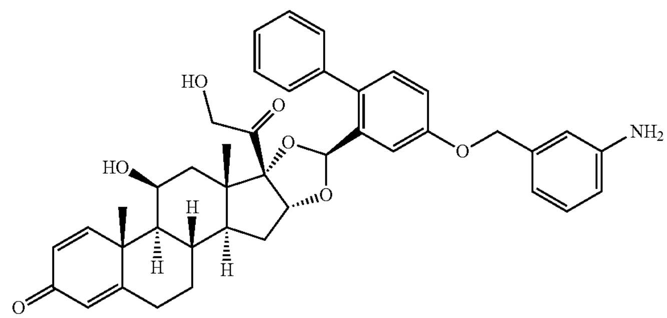 | 662.4 | A |
| 154 | 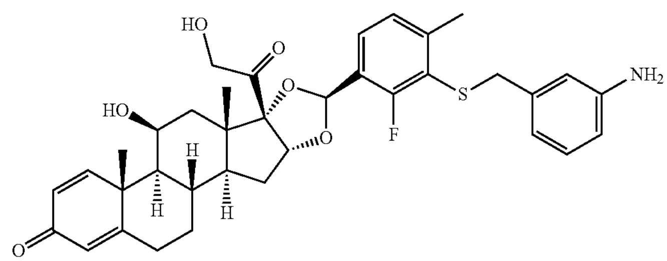 | 634.5 | B |
| 155 | 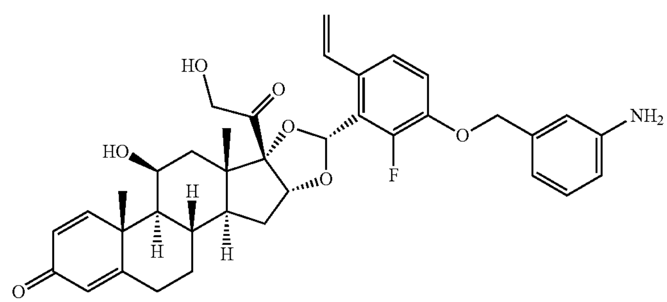 | 630.4 | A |
| 156 | 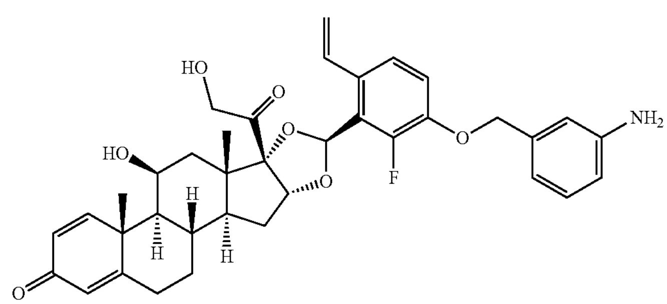 | 630.4 | A |

TABLE 18a-continued

Examples 6-158 (structures)

| Ex No. | Structure | ES/MS (m/z) (M + H) | Purification method* |
|---|---|---|---|
| 157 | [structure] | 606.4 | A |
| 158 | [structure] | 634.5 | B |

TABLE 18b

Examples 6-158 (chemical names)

| Ex No. | Chemical Name |
|---|---|
| 6 | (6aR,6bS,7S,8aS,8bS,10R,11aR,12aS,12bS)-10-(3-(4-aminobenzyl)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 7 | (6aR,6bS,7S,8aS,8bS,10S,11aR,12aS,12bS)-10-(3-(4-aminobenzyl)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 8 | (6aR,6bS,7S,8aS,8bS,10R,11aR,12aS,12bS)-10-(3-(3-aminobenzyl)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 9 | (6aR,6bS,7S,8aS,8bS,10S,11aR,12aS,12bS)-10-(3-(3-aminobenzyl)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 10 | (6aR,6bS,7S,8aS,8bS,10R,11aR,12aS,12bS)-10-(3-(2-aminobenzyl)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 11 | (6aR,6bS,7S,8aS,8bS,10S,11aR,12aS,12bS)-10-(3-(2-aminobenzyl)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 12 | (6aR,6bS,7S,8aS,8bS,10R,11aR,12aS,12bS)-10-(3-(4-aminophenoxy)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 13 | (6aR,6bS,7S,8aS,8bS,10S,11aR,12aS,12bS)-10-(3-(4-aminophenoxy)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 14 | (6aR,6bS,7S,8aS,8bS,10R,11aR,12aS,12bS)-10-(3-(3-aminophenoxy)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 15 | (6aR,6bS,7S,8aS,8bS,10S,11aR,12aS,12bS)-10-(3-(3-aminophenoxy)phenyl)-7-hydroxy-8b-(2-hydroxyacetyl)-6a,8a-dimethyl- |

TABLE 18b-continued

Examples 6-158 (chemical names)

| Ex No. | Chemical Name |
|---|---|
| | 1,2,6a,6b,7,8,8a,8b,11a,12,12a,12b-dodecahydro-4H-naphtho[2',1':4,5]indeno[1,2-d][1,3]dioxol-4-one |
| 16 | (6aR,6bS,7S,8aS,8bS,10R,11aR,12aS,12bS)-10-(3-((3-aminobenzyl)oxy)-2-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 17 | (6aR,6bS,7S,8aS,8bS,10R,11aR,12aS,12bS)-10-(5-((3-aminobenzyl)oxy)-2-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 18 | (6aR,6bS,7S,8aS,8bS,10S,11aR,12aS,12bS)-10-(5-((3-aminobenzyl)oxy)-2-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 19 | (6aR,6bS,7S,8aS,8bS,10R,11aR,12aS,12bS)-10-(3-((3-aminobenzyl)oxy)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 20 | (6aR,6bS,7S,8aS,8bS,10S,11aR,12aS,12bS)-10-(3-((3-aminobenzyl)oxy)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 21 | (6aR,6bS,7S,8aS,8bS,10RS,11aR,12aS,12bS)-10-(5-((3-aminobenzyl)oxy)-2-fluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 22 | (6aR,6bS,7S,8aS,8bS,10S,11aR,12aS,12bS)-10-(5-((3-aminobenzyl)oxy)-2-fluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 23 | (6aR,6bS,7S,8aS,8bS,10R,11aR,12aS,12bS)-10-(3-((3-aminobenzyl)oxy)-4-chlorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 24 | (6aR,6bS,7S,8aS,8bS,10S,11aR,12aS,12bS)-10-(3-((3-aminobenzyl)oxy)-4-chlorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 25 | (6aR,6bS,7S,8aS,8bS,10R,11aR,12aS,12bS)-10-(3-((3-aminobenzyl)oxy)-5-chlorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 26 | (6aR,6bS,7S,8aS,8bS,10S,11aR,12aS,12bS)-10-(3-((3-aminobenzyl)oxy)-5-chlorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 27 | (6aR,6bS,7S,8aS,8bS,10R,11aR,12aS,12bS)-10-(5-((3-aminobenzyl)oxy)-2-chlorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 28 | (6aR,6bS,7S,8aS,8bS,10S,11aR,12aS,12bS)-10-(5-((3-aminobenzyl)oxy)-2-chlorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 29 | (6aR,6bS,7S,8aS,8bS,10R,11aR,12aS,12bS)-10-(3-((3-aminobenzyl)oxy)-5-fluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 30 | (6aR,6bS,7S,8aS,8bS,10S,11aR,12aS,12bS)-10-(3-((3-aminobenzyl)oxy)-5-fluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 31 | (6aR,6bS,7S,8aS,8bS,10R,11aR,12aS,12bS)-10-(3-((3-aminobenzyl)oxy)-2-chlorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 32 | (6aR,6bS,7S,8aS,8bS,10S,11aR,12aS,12bS)-10-(3-((3-aminobenzyl)oxy)-2-chlorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 33 | (6aR,6bS,7S,8aS,8bS,10R,11aR,12aS,12bS)-10-(3'-amino-[1,1'-biphenyl]-3-yl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 34 | (6aR,6bS,7S,8aS,8bS,10S,11aR,12aS,12bS)-10-(3'-amino-[1,1'-biphenyl]-3-yl)-7-hydroxy-8b-(2-hydroxyacetyl)-6a,8a-dimethyl- |

TABLE 18b-continued

Examples 6-158 (chemical names)

| Ex No. | Chemical Name |
|---|---|
| | 1,2,6a,6b,7,8,8a,8b,11a,12,12a,12b-dodecahydro-4H-naphtho[2',1':4,5]indeno[1,2-d][1,3]dioxol-4-one |
| 35 | (6aR,6bS,7S,8aS,8bS,10R,11aR,12aS,12bS)-10-(3-((3-aminobenzyl)oxy)-5-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 36 | (6aR,6bS,7S,8aS,8bS,10S,11aR,12aS,12bS)-10-(3-((3-aminobenzyl)oxy)-5-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 37 | (6aR,6bS,7S,8aS,8bS,10R,11aR,12aS,12bS)-10-(3-((3-aminobenzyl)oxy)-2-fluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 38 | (6aR,6bS,7S,8aS,8bS,10S,11aR,12aS,12bS)-10-(3-((3-aminobenzyl)oxy)-2-fluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 39 | (6aR,6bS,7S,8aS,8bS,10R,11aR,12aS,12bS)-10-(4'-amino-[1,1'-biphenyl]-3-yl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 40 | (6aR,6bS,7S,8aS,8bS,10S,11aR,12aS,12bS)-10-(4'-amino-[1,1'-biphenyl]-3-yl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 41 | (6aR,6bS,7S,8aS,8bS,10S,11aR,12aS,12bS)-10-(3-((3-aminobenzyl)oxy)-2-chloro-6-fluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 42 | (6aR,6bS,7S,8aS,8bS,10R,11aR,12aS,12bS)-10-(2-((3-aminobenzyl)oxy)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 43 | (6aR,6bS,7S,8aS,8bS,10R,11aR,12aS,12bS)-10-(3-((3-aminobenzyl)oxy)-2-chloro-6-fluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 44 | (6aR,6bS,7S,8aS,8bS,10S,11aR,12aS,12bS)-10-(2-((3-aminobenzyl)oxy)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 45 | (6aR,6bS,7S,8aS,8bS,10S,11aR,12aS,12bS)-10-(2-((3-aminobenzyl)oxy)-6-fluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 46 | (6aR,6bS,7S,8aS,8bS,10R,11aR,12aS,12bS)-10-(2-((3-aminobenzyl)oxy)-6-fluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 47 | (6aR,6bS,7S,8aS,8bS,10R,11aR,12aS,12bS)-10-(3-((3-aminobenzyl)oxy)-6-chloro-2-fluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 48 | (6aR,6bS,7S,8aS,8bS,10S,11aR,12aS,12bS)-10-(3-((3-aminobenzyl)oxy)-6-chloro-2-fluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 49 | (6aR,6bS,7S,8aS,8bS,10R,11aR,12aS,12bS)-10-(3-((3-aminobenzyl)oxy)-2,6-difluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 50 | (6aR,6bS,7S,8aS,8bS,10S,11aR,12aS,12bS)-10-(3-((3-aminobenzyl)oxy)-2,6-difluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 51 | (6aR,6bS,7S,8aS,8bS,10R,11aR,12aS,12bS)-10-(2-((3-aminobenzyl)oxy)-6-chlorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 52 | (6aR,6bS,7S,8aS,8bS,10S,11aR,12aS,12bS)-10-(2-((3-aminobenzyl)oxy)-6-chlorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 53 | (6aR,6bS,7S,8aS,8bS,10R,11aR,12aS,12bS)-10-(5-(4-aminobenzyl)-2-fluorophenyl)-7-hydroxy-8b-(2-hydroxyacetyl)-6a,8a-dimethyl- |

TABLE 18b-continued

Examples 6-158 (chemical names)

| Ex No. | Chemical Name |
|---|---|
|  | 1,2,6a,6b,7,8,8a,8b,11a,12,12a,12b-dodecahydro-4H-naphtho[2',1':4,5]indeno[1,2-d][1,3]dioxol-4-one |
| 54 | (6aR,6bS,7S,8aS,8bS,10S,11aR,12aS,12bS)-10-(5-(4-aminobenzyl)-2-fluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 55 | (6aR,6bS,7S,8aS,8bS,10S,11aR,12aS,12bS)-10-(3-((3-aminobenzyl)amino)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 56 | (6aR,6bS,7S,8aS,8bS,10S,11aR,12aS,12bS)-10-(3-((2-aminobenzyl)oxy)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 57 | (6aR,6bS,7S,8aS,8bS,10R,11aR,12aS,12bS)-10-(3-((2-aminobenzyl)oxy)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 58 | (6aR,6bS,7S,8aS,8bS,10S,11aR,12aS,12bS)-10-(3-((3-aminobenzyl)oxy)-2,4-difluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 59 | (6aR,6bS,7S,8aS,8bS,10R,11aR,12aS,12bS)-10-(3-((3-aminobenzyl)oxy)-2,4-difluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 60 | (6aR,6bS,7S,8aS,8bS,10R,11aR,12aS,12bS)-10-(3-((3-aminobenzyl)oxy)-6-fluoro-2-methoxyphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 61 | (6aR,6bS,7S,8aS,8bS,10S,11aR,12aS,12bS)-10-(3-((3-aminobenzyl)oxy)-6-fluoro-2-methoxyphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 62 | (6aR,6bS,7S,8aS,8bS,10S,11aR,12aS,12bS)-10-(3-((2-(aminomethyl)benzyl)oxy)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 63 | (6aR,6bS,7S,8aS,8bS,10R,11aR,12aS,12bS)-10-(3-((2-(aminomethyl)benzyl)oxy)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 64 | (6aR,6bS,7S,8aS,8bS,10S,11aR,12aS,12bS)-10-(3-((2-aminobenzyl)amino)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 65 | (6aR,6bS,7S,8aS,8bS,10S,11aR,12aS,12bS)-10-(3-((2-aminobenzyl)thio)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 66 | (6aR,6bS,7S,8aS,8bS,10S,11aR,12aS,12bS)-10-(3-((3-aminobenzyl)thio)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 67 | (6aR,6bS,7S,8aS,8bS,10S,11aR,12aS,12bS)-10-(3-((2-aminophenoxy)methyl)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 68 | (6aR,6bS,7S,8aS,8bS,10S,11aR,12aS,12bS)-10-(3-((3-aminophenoxy)methyl)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 69 | (6aR,6bS,7S,8aS,8bS,10S,11aR,12aS,12bS)-10-(3-(((3-aminophenyl)amino)methyl)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 70 | (6aR,6bS,7S,8aS,8bS,10S,11aR,12aS,12bS)-10-(3-(((2-aminophenyl)amino)methyl)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 71 | (6aR,6bS,7S,8aS,8bS,10S,11aR,12aS,12bS)-10-(3-(((2-aminophenyl)thio)methyl)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 72 | (6aR,6bS,7S,8aS,8bS,10S,11aR,12aS,12bS)-10-(3-(((3-aminophenyl)thio)methyl)-2-fluoro-6-methylphenyl)-7-hydroxy-8b-(2- |

TABLE 18b-continued

Examples 6-158 (chemical names)

| Ex No. | Chemical Name |
|---|---|
| | hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 73 | (6aR,6bS,7S,8aS,8bS,10R,11aR,12aS,12bS)-10-(3-((3-aminobenzyl)amino)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 74 | (6aR,6bS,7S,8aS,8bS,10R,11aR,12aS,12bS)-10-(5-((3-aminobenzyl)oxy)-2-(trifluoromethoxy)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 75 | (6aR,6bS,7S,8aS,8bS,10S,11aR,12aS,12bS)-10-(3-((3-(aminomethyl)benzyl)oxy)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 76 | (6aR,6bS,7S,8aS,8bS,10R,11aR,12aS,12bS)-10-(3-((3-(aminomethyl)benzyl)oxy)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 77 | (6aR,6bS,7S,8aS,8bS,10R,11aR,12aS,12bS)-10-(3-((2-aminobenzyl)oxy)-2-fluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 78 | (6aR,6bS,7S,8aS,8bS,10S,11aR,12aS,12bS)-10-(3-((2-aminobenzyl)oxy)-2-fluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 79 | (6aR,6bS,7S,8aS,8bS,10S,11aR,12aS,12bS)-10-(5-((3-aminobenzyl)oxy)-2-(trifluoromethoxy)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 80 | (6aR,6bS,7S,8aS,8bS,10R,11aR,12aS,12bS)-10-(5-((2-aminobenzyl)oxy)-2-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 81 | (6aR,6bS,7S,8aS,8bS,10S,11aR,12aS,12bS)-10-(5-((2-aminobenzyl)oxy)-2-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 82 | (6aR,6bS,7S,8aS,8bS,10R,11aR,12aS,12bS)-10-(3-((2-aminobenzyl)oxy)-2,6-difluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 83 | (6aR,6bS,7S,8aS,8bS,10S,11aR,12aS,12bS)-10-(3-((2-aminobenzyl)oxy)-2,6-difluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 84 | (6aR,6bS,7S,8aS,8bS,10S,11aR,12aS,12bS)-10-(3-(4-aminophenethoxy)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 85 | (6aR,6bS,7S,8aS,8bS,10S,11aR,12aS,12bS)-10-(3-(3-aminophenethoxy)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 86 | (6aR,6bS,7S,8aS,8bS,10S,11aR,12aS,12bS)-10-(3-((3-aminobenzyl)(methyl)amino)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 87 | (6aR,6bS,7S,8aS,8bS,10S,11aR,12aS,12bS)-10-(3-(4-aminophenethyl)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 88 | (6aR,6bS,7S,8aS,8bS,10R,11aR,12aS,12bS)-10-(5-((3-aminobenzyl)oxy)-2-methoxyphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 89 | (6aR,6bS,7S,8aS,8bS,10S,11aR,12aS,12bS)-10-(5-((3-aminobenzyl)oxy)-2-methoxyphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 90 | (6aR,6bS,7S,8aS,8bS,10R,11aR,12aS,12bS)-10-(3-((3-aminobenzyl)oxy)-2-methoxyphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 91 | (6aR,6bS,7S,8aS,8bS,10S,11aR,12aS,12bS)-10-(3-((3-aminobenzyl)oxy)-2-methoxyphenyl)-7-hydroxy-8b-(2-hydroxyacetyl)-6a,8a-dimethyl- |

TABLE 18b-continued

Examples 6-158 (chemical names)

| Ex No. | Chemical Name |
|---|---|
|  | 1,2,6a,6b,7,8,8a,8b,11a,12,12a,12b-dodecahydro-4H-naphtho[2',1':4,5]indeno[1,2-d][1,3]dioxol-4-one |
| 92 | (6aR,6bS,7S,8aS,8bS,10R,11aR,12aS,12bS)-10-(5-((3-aminobenzyl)oxy)-2-bromophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 93 | (6aR,6bS,7S,8aS,8bS,10S,11aR,12aS,12bS)-10-(5-((3-aminobenzyl)oxy)-2-bromophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 94 | (6aR,6bS,7S,8aS,8bS,10R,11aR,12aS,12bS)-10-(3-((2-aminobenzyl)oxy)-2-chloro-6-fluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 95 | (6aR,6bS,7S,8aS,8bS,10S,11aR,12aS,12bS)-10-(3-((2-aminobenzyl)oxy)-2-chloro-6-fluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 96 | (6aR,6bS,7S,8aS,8bS,10R,11aR,12aS,12bS)-10-(3-((3-aminobenzyl)oxy)-6-fluoro-2-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 97 | (6aR,6bS,7S,8aS,8bS,10S,11aR,12aS,12bS)-10-(3-((3-aminobenzyl)oxy)-6-fluoro-2-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 98 | (6aR,6bS,7S,8aS,8bS,10R,11aR,12aS,12bS)-10-(3-((2-aminobenzyl)oxy)-2-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 99 | (6aR,6bS,7S,8aS,8bS,10S,11aR,12aS,12bS)-10-(3-((2-aminobenzyl)oxy)-2-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 100 | (6aR,6bS,7S,8aS,8bS,10R,11aR,12aS,12bS)-10-(3-((2-aminobenzyl)oxy)-2-fluoro-6-methoxyphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 101 | (6aR,6bS,7S,8aS,8bS,10S,11aR,12aS,12bS)-10-(3-((2-aminobenzyl)oxy)-2-fluoro-6-methoxyphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 102 | (6aR,6bS,7S,8aS,8bS,10R,11aR,12aS,12bS)-10-(3-(((3-aminophenyl)thio)methyl)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 103 | (6aR,6bS,7S,8aS,8bS,10R,11aR,12aS,12bS)-10-(3-(((2-aminophenyl)thio)methyl)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 104 | (6aR,6bS,7S,8aS,8bS,10R,11aR,12aS,12bS)-10-(3-(((2-aminophenyl)amino)methyl)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 105 | (6aR,6bS,7S,8aS,8bS,10R,11aR,12aS,12bS)-10-(3-(((3-aminophenyl)amino)methyl)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 106 | (6aR,6bS,7S,8aS,8bS,10R,11aR,12aS,12bS)-10-(3-((3-aminophenoxy)methyl)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 107 | (6aR,6bS,7S,8aS,8bS,10R,11aR,12aS,12bS)-10-(3-((2-aminophenoxy)methyl)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 108 | (6aR,6bS,7S,8aS,8bS,10R,11aR,12aS,12bS)-10-(3-((3-aminobenzyl)thio)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 109 | (6aR,6bS,7S,8aS,8bS,10R,11aR,12aS,12bS)-10-(3-((2-aminobenzyl)thio)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 110 | (6aR,6bS,7S,8aS,8bS,10R,11aR,12aS,12bS)-10-(3-((2-aminobenzyl)amino)-2-fluoro-6-methylphenyl)-7-hydroxy-8b-(2- |

TABLE 18b-continued

Examples 6-158 (chemical names)

| Ex No. | Chemical Name |
|---|---|
| | hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 111 | (6aR,6bS,7S,8aS,8bS,10R,11aR,12aS,12bS)-10-(3-(3-aminophenethoxy)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 112 | (6aR,6bS,7S,8aS,8bS,10R,11aR,12aS,12bS)-10-(3-((3-aminobenzyl)(methyl)amino)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 113 | (6aR,6bS,7S,8aS,8bS,10R,11aR,12aS,12bS)-10-(3-(4-aminophenethyl)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 114 | (6aR,6bS,7S,8aS,8bS,10R,11aR,12aS,12bS)-10-(3-(4-aminophenethoxy)-2-fluoro-6-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 115 | (6aR,6bS,7S,8aS,8bS,10S,11aR,12aS,12bS)-10-(5-(4-aminophenoxy)-2-methoxyphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 116 | (6aR,6bS,7S,8aS,8bS,10S,11aR,12aS,12bS)-10-(5-(3-aminophenoxy)-2-methoxyphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 117 | (6aR,6bS,7S,8aS,8bS,10R,11aR,12aS,12bS)-10-(3-((3-aminobenzyl)oxy)-6-bromo-2-fluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 118 | (6aR,6bS,7S,8aS,8bS,10S,11aR,12aS,12bS)-10-(3-((3-aminobenzyl)oxy)-6-bromo-2-fluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 119 | (6aR,6bS,7S,8aS,8bS,10R,11aR,12aS,12bS)-10-(3-((3-aminobenzyl)oxy)-2-bromophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 120 | (6aR,6bS,7S,8aS,8bS,10R,11aR,12aS,12bS)-10-(5-((2-aminobenzyl)oxy)-2-methoxyphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 121 | (6aR,6bS,7S,8aS,8bS,10S,11aR,12aS,12bS)-10-(5-((2-aminobenzyl)oxy)-2-methoxyphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 122 | (6aR,6bS,7S,8aS,8bS,10R,11aR,12aS,12bS)-10-(4-((3-aminobenzyl)oxy)-3-fluoro-[1,1'-biphenyl]-2-yl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 123 | (6aR,6bS,7S,8aS,8bS,10S,11aR,12aS,12bS)-10-(4-((3-aminobenzyl)oxy)-3-fluoro-[1,1'-biphenyl]-2-yl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 124 | (6aR,6bS,7S,8aS,8bS,10R,11aR,12aS,12bS)-10-(5-((3-aminobenzyl)oxy)-2-iodophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 125 | (6aR,6bS,7S,8aS,8bS,10S,11aR,12aS,12bS)-10-(5-((3-aminobenzyl)oxy)-2-iodophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 126 | (6aR,6bS,7S,8aS,8bS,10S,11aR,12aS,12bS)-10-(5-((3-aminobenzyl)oxy)-2-(thiophen-2-yl)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 127 | (6aR,6bS,7S,8aS,8bS,10R,11aR,12aS,12bS)-10-(3-((3-aminophenyl)ethynyl)-2-fluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 128 | (6aR,6bS,7S,8aS,8bS,10S,11aR,12aS,12bS)-10-(3-((3-aminophenyl)ethynyl)-2-fluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 129 | (6aR,6bS,7S,8aS,8bS,10R,11aR,12aS,12bS)-10-(3-((3-aminobenzyl)oxy)-2,6-dimethylphenyl)-7-hydroxy-8b-(2-hydroxyacetyl)-6a,8a-dimethyl- |

TABLE 18b-continued

Examples 6-158 (chemical names)

| Ex No. | Chemical Name |
|---|---|
|  | 1,2,6a,6b,7,8,8a,8b,11a,12,12a,12b-dodecahydro-4H-naphtho[2',1':4,5]indeno[1,2-d][1,3]dioxol-4-one |
| 130 | (6aR,6bS,7S,8aS,8bS,10S,11aR,12aS,12bS)-10-(3-((3-aminobenzyl)oxy)-2,6-dimethylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 131 | (6aR,6bS,7S,8aS,8bS,10R,11aR,12aS,12bS)-10-(5-((3-aminobenzyl)oxy)-2-(furan-3-yl)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 132 | (6aR,6bS,7S,8aS,8bS,10S,11aR,12aS,12bS)-10-(5-((3-aminobenzyl)oxy)-2-(furan-3-yl)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 133 | (6aR,6bS,7S,8aS,8bS,10R,11aR,12aS,12bS)-10-(5-((3-aminobenzyl)oxy)-2-ethoxyphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 134 | (6aR,6bS,7S,8aS,8bS,10S,11aR,12aS,12bS)-10-(5-((3-aminobenzyl)oxy)-2-ethoxyphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 135 | (6aR,6bS,7S,8aS,8bS,10R,11aR,12aS,12bS)-10-(3-((3-aminobenzyl)amino)-2,6-dimethylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 136 | (6aR,6bS,7S,8aS,8bS,10S,11aR,12aS,12bS)-10-(3-((3-aminobenzyl)amino)-2,6-dimethylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 137 | (6aR,6bS,7S,8aS,8bS,10S,11aR,12aS,12bS)-10-(3-((3-aminobenzyl)oxy)-2-bromophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 138 | (6aR,6bS,7S,8aS,8bS,10R,11aR,12aS,12bS)-10-(3-((3-aminobenzyl)oxy)-2-fluoro-6-isopropylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 139 | (6aR,6bS,7S,8aS,8bS,10S,11aR,12aS,12bS)-10-(3-((3-aminobenzyl)oxy)-2-fluoro-6-isopropylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 140 | (6aR,6bS,7S,8aS,8bS,10S,11aR,12aS,12bS)-10-(3-((2-aminobenzyl)oxy)-6-chloro-2-fluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 141 | (6aR,6bS,7S,8aS,8bS,10S,11aR,12aS,12bS)-10-(5-(3-aminobenzyl)-2-chlorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 142 | (6aR,6bS,7S,8aS,8bS,10S,11aR,12aS,12bS)-10-(5-(4-aminobenzyl)-2-chlorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 143 | (6aR,6bS,7S,8aS,8bS,10S,11aR,12aS,12bS)-10-(3-(3-aminobenzyl)-6-chloro-2-fluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 144 | (6aR,6bS,7S,8aS,8bS,10R,11aR,12aS,12bS)-10-(5-((3-aminobenzyl)oxy)-2-(furan-2-yl)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 145 | (6aR,6bS,7S,8aS,8bS,10S,11aR,12aS,12bS)-10-(5-((3-aminobenzyl)oxy)-2-(furan-2-yl)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 146 | (6aR,6bS,7S,8aS,8bS,10S,11aR,12aS,12bS)-10-(3-(4-aminobenzyl)-6-chloro-2-fluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 147 | (6aR,6bS,7S,8aS,8bS,10R,11aR,12aS,12bS)-10-(3-((3-aminobenzyl)oxy)-2-fluoro-4-methoxyphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 148 | (6aR,6bS,7S,8aS,8bS,10S,11aR,12aS,12bS)-10-(3-((3-aminobenzyl)oxy)-2-fluoro-4-methoxyphenyl)-7-hydroxy-8b-(2-hydroxyacetyl)-6a,8a- |

TABLE 18b-continued

Examples 6-158 (chemical names)

| Ex No. | Chemical Name |
|---|---|
| | dimethyl-1,2,6a,6b,7,8,8a,8b,11a,12,12a,12b-dodecahydro-4H-naphtho[2',1':4,5]indeno[1,2-d][1,3]dioxol-4-one |
| 149 | (6aR,6bS,7S,8aS,8bS,10S,11aR,12aS,12bS)-10-(3-(3-aminobenzyl)-2,6-difluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 150 | (6aR,6bS,7S,8aS,8bS,10R,11aR,12aS,12bS)-10-(3-((3-aminobenzyl)oxy)-6-cyclopropyl-2-fluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 151 | (6aR,6bS,7S,8aS,8bS,10S,11aR,12aS,12bS)-10-(3-((3-aminobenzyl)oxy)-6-cyclopropyl-2-fluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 152 | (6aR,6bS,7S,8aS,8bS,10R,11aR,12aS,12bS)-10-(4-((3-aminobenzyl)oxy)-[1,1'-biphenyl]-2-yl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 153 | (6aR,6bS,7S,8aS,8bS,10S,11aR,12aS,12bS)-10-(4-((3-aminobenzyl)oxy)-[1,1'-biphenyl]-2-yl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 154 | (6aR,6bS,7S,8aS,8bS,10S,11aR,12aS,12bS)-10-(3-((3-aminobenzyl)thio)-2-fluoro-4-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 155 | (6aR,6bS,7S,8aS,8bS,10R,11aR,12aS,12bS)-10-(3-((3-aminobenzyl)oxy)-2-fluoro-6-vinylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 156 | (6aR,6bS,7S,8aS,8bS,10S,11aR,12aS,12bS)-10-(3-((3-aminobenzyl)oxy)-2-fluoro-6-vinylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 157 | (6aR,6bS,7S,8aS,8bS,10R,11aR,12aS,12bS)-10-(3-(3-aminobenzyl)-2,6-difluorophenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |
| 158 | (6aR,6bS,7S,8aS,8bS,10R,11aR,12aS,12bS)-10-(3-((3-aminobenzyl)thio)-2-fluoro-4-methylphenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one |

EXAMPLE 159

4-((3-Aminobenzyl)oxy)-3-fluoro-2-((6aR,6bS,7S,8aS,8bS,10S,11aR,12aS,12bS)-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzonitrile

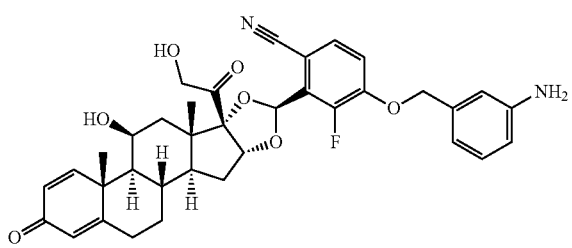

Trifluoromethanesulfonic acid (920 µL, 10 mmol) was added dropwise to a suspension of 16alpha-hydroxyprednisolone (140 mg, 0.36 mmol) and tert-butyl (3-((4-cyano-3-(1,3-dioxolan-2-yl)-2-fluorophenoxy)methyl)phenyl)carbamate (140 mg, 0.34 mmol) in ACN (5 mL, 95 mmol) at 0° C. The reaction was quenched with satd aq NaHCO$_3$ and extracted with 10% IPA in DCM. The combined organic layers were dried with MgSO$_4$, filtered, and concentrated to a crude residue. The crude residue was purified by reverse phase purification, eluting with 1:1 10 mM NH$_4$HCO$_3$ in water+5% MeOH:ACN to give the title compound (12 mg, 6% yield). MS m/z 630.0 (M+H). $^1$H NMR (400.13 MHz, d$_6$-DMSO) δ 7.70-7.67 (m, 1H), 7.45-7.41 (m, 1H), 7.33 (d, J=10.1 Hz, 1H), 7.04-7.00 (m, 1H), 6.61-6.51 (m, 3H), 6.45 (s, 1H), 6.20-6.17 (m, 1H), 5.95 (s, 1H), 5.37-5.35 (m, 1H), 5.15 (s, 4H), 4.86-4.84 (m, 1H), 4.32-4.31 (m, 2H), 4.07-4.01 (m, 1H), 2.14-2.12 (m, 2H), 1.92-1.88 (m, 4H), 1.67-1.66 (m, 1H), 1.40-1.39 (m, 3H), 1.25-1.20 (m, 2H), 0.89-0.88 (m, 3H).

hGR CoActivator Recruitment Assay

The activity of glucocorticoid compounds was measured using the LanthaScreen TR-Fret GR Coactivator Assay from Life Technologies (A15899). The compounds were acoustically transferred to an assay plate in a 3-fold 10-point serial dilution with a top concentration of 200 nM. Ten microliters of a 2× solution of GR-LBD was added to the compound plate and incubated for 10 min. Then ten microliters of a 2× solution of Fluoresein-SRC1-4 and Tb labelled anti-GST antibody were added to the plate. The plate was incubated in the dark for two hours and then read on an Envision plate reader, with excitation at 340 nm and emission at 520 nm (Fluorescein) and 490 nm (Terbium). The emission ratio of 520/490 was analyzed in Genedata. To obtain percent activity, the data was compared to a negative control of DMSO and positive control of 4 uM dexamethasone. The following exemplified compounds were tested following the procedure as essentially described above and exhibited the following activity as listed in Table 19.

TABLE 19

In vitro potency of compounds of Examples 1, 2, 4, and 5 in the hGR CoActivator Recruitment Assay

| Example No. | IC$_{50}$ (nM) |
|---|---|
| 1 | 2.12 |
| 2 | 1.44 |
| 4 | 2.47 |
| 5 | 1.40 |

The compounds of Examples 6-44, 46-51, 53-79, and 81-158 provided a relative IC$_{50}$ of less than 200 nM. The compounds of Examples 45, 52, and 80 provided a relative IC$_{50}$ of greater than 200 nM.

What is claimed is:

1. A compound, wherein the compound is:

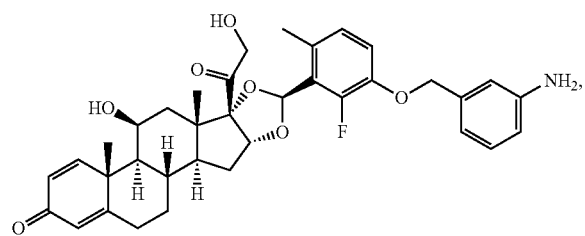

or a pharmaceutically acceptable salt thereof.

2. The compound according to claim 1 which is:

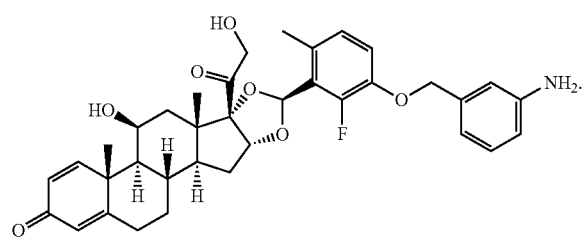

3. A compound, wherein the compound is:

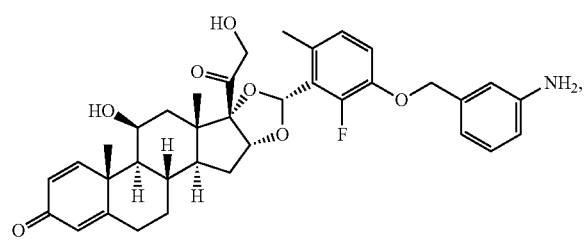

or a pharmaceutically acceptable salt thereof.

4. The compound according to claim 3 which is:

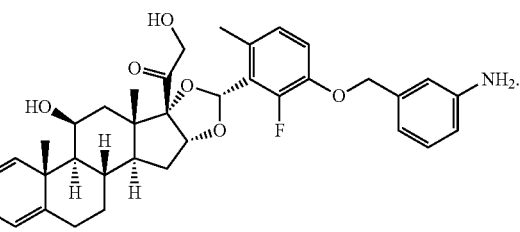

5. A compound, wherein the compound is:

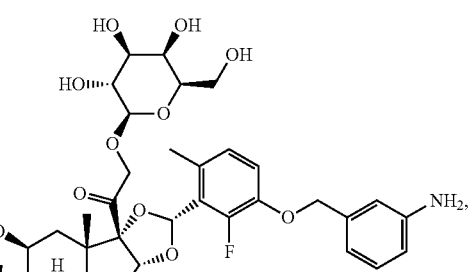

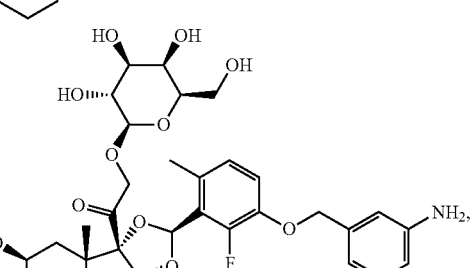

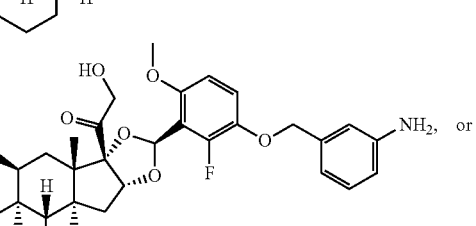

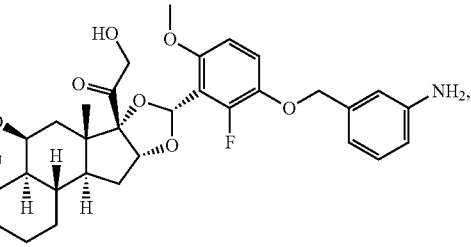

or a pharmaceutically acceptable salt thereof.

6. A pharmaceutical composition comprising the compound, or a pharmaceutically acceptable salt thereof, according to claim 1 and one or more pharmaceutically acceptable carrier, diluent, or excipient.

7. A pharmaceutical composition comprising the compound, or a pharmaceutically acceptable salt thereof, according to claim 3 and one or more pharmaceutically acceptable carrier, diluent, or excipient.

* * * * *